US009313968B2

(12) United States Patent
Cook et al.

(10) Patent No.: US 9,313,968 B2
(45) Date of Patent: *Apr. 19, 2016

(54) PEPPER PLANTS PRODUCING FRUITS WITH EXTREME DARK GREEN COLOR

(71) Applicant: Syngenta Participations AG, Basel (CH)

(72) Inventors: Kevin Cook, Naples, FL (US); Laurie Boyden, Stanton, MN (US); Steve Czaplewski, Naples, FL (US); Henricus Johannes Van Wijk, Nibbixwoud (NL)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/645,376

(22) Filed: Mar. 11, 2015

(65) Prior Publication Data

US 2015/0257352 A1      Sep. 17, 2015

Related U.S. Application Data

(60) Provisional application No. 61/951,697, filed on Mar. 12, 2014.

(51) Int. Cl.
*A01H 5/08* (2006.01)

(52) U.S. Cl.
CPC ........................................ *A01H 5/08* (2013.01)

(58) Field of Classification Search
None
See application file for complete search history.

(56) References Cited

U.S. PATENT DOCUMENTS

2011/0258744 A1* 10/2011 Todd et al. .................. 800/317.1
2012/0110687 A1*  5/2012 Just et al. ....................... 800/260
2014/0230102 A1   8/2014 Boyden et al.

OTHER PUBLICATIONS

Trade Winds Fruit online seed catalog, "Ancho San Luis Pepper".*
Siegers Seed Co. online catalog, "Hunter" and "Tomcat" hybrid pepper varieties.*
Lee et al., "Flavonoids and antioxidant activity of fresh pepper (*Capsicum annuum*) cultivars", Journal of Food Science, 60, Jan. 1, 1995, pp. 473-476.
Camara et al., "Free and esterified carotenoids in green and red fruits of Capsicum annuum", phytochemistry, Pergmon Press, GB, 17(1), Jan. 1, 1978, pp. 91-93.
Minguez-Mosquera et al., "Formation and transformation of pigments duing the furit rpening of Capsicum annuum cv. Bola and Agridulce," Jouornal of Agricultural and Food Chemistry, American Chemical Society, US, 42(1), Jan. 1, 1994, pp. 38-44.
Chaim et al., "QLT mapping of fruit-related traits ain pepper (*Capsicum annuum*)," Theoretical and Applied Genetics, vol. 102, Jan. 1, 2001, pp. 1016-1028.
Brand et al., "pc8.1, a major QTL for pigment content in pepper furit is associated with variation in plastid compartment size,", Oct. 11, 2011 Planta (online publication).
Hornero-Mendez et al., "Carotenoid biosynthesis changes in five red pepper (*Capsicum annuum* L.) cultivars during rpening. Cultivar selection for breeding," Journal of Agricultural and Food Chemistry, American Chemical Society, US, 48(9), Sep. 1, 2000, pp. 3857-3864.
Lightbourn et al., "Effects of Anthocyanin and Carotenoid combinations on foliage and and immature fruit color Capisicum annuum L.," Journal of Heredity, 99(2), Jan. 24, 2008, pp. 105-111.
Ji-Sun Kim et al., "Phytochemicals and antioxidant activity of fruits and leaves of paprika (*Capsicum Annuum* L, var. special) Cultivated in Kore," Journal of Food Science, 76(2), Jan. 21, 2011, pp. C193-C198.
Borovsky et al., "Chlorophyll breakdown during pepper furit ripening in the chlorophyll retainer mutation is impaired at the homolog of the senescence-inducible stay-green gene," Theoretical and Applied Genetics, Interntional Journal of Plant Breeding Research, Springer, Berlin, DE, 117(2), Apr. 22, 2008, pp. 235-240.
International Search Report dated Nov. 20, 2012 for International Patent Application No. PCT/EP2012/067585.
International Preliminary Report on Patentability dated Mar. 12, 2014 for International Patent Application No. PCT/EP2012/067585.

* cited by examiner

*Primary Examiner* — David T Fox
(74) *Attorney, Agent, or Firm* — Karen A. Magri

(57) ABSTRACT

The present invention concerns *Capsicum annuum* plants producing pepper fruits exhibiting new physicochemical characteristics of the pepper fruit in relation to pigments such as chlorophyll A, chlorophyll B, α-carotene, β-carotene, lutein and/or violaxanthin. The pepper fruits of the plants according to the present invention also exhibit a characteristic extreme dark green color at immature stage. The present invention also relates to QTL alleles directing the expression of the pigment content of those pepper fruits as well as molecular markers associated with these QTL alleles. The invention further provides novel pepper cultivars RPP 25822, RPP 26098, RPP 26105, 16452A, 16452B 16452C and 8728C, and plant parts, seed, and tissue culture therefrom. The invention additionally provides methods for producing a pepper plant by crossing the pepper plants of the invention with themselves or another pepper plant. The invention also provides pepper plants produced from such a crossing as well as plant parts, seed, and tissue culture therefrom.

24 Claims, 15 Drawing Sheets

PEPPER PLANTS PRODUCING FRUITS WITH EXTREME DARK GREEN COLOR

RELATED APPLICATION INFORMATION

This application claims the benefit of U.S. Provisional Application Ser. No. 61/951,697, filed 12 Mar. 2014, the disclosure of which is incorporated by reference herein in its entirety.

FIELD OF THE INVENTION

This invention is in the field of pepper plants, in particular, the invention relates to novel pepper plants producing fruits having an extreme dark green color.

BACKGROUND OF THE INVENTION

Fruits of plants of the genus *Capsicum*, like sweet peppers and hot peppers, hereafter both types being referred to as peppers, are available in a wide variety of different colors like red, yellow, brown, and orange generally for fully matured fruits and green, white, lilac, and purple for non-mature "unripe" fruits.

Chlorophyll is the molecule that is called a photoreceptor. It is found in the chloroplasts of green pepper plants, and is what makes pepper fruits green. The basic structure of a chlorophyll molecule is a porphyrin ring, coordinated to a central atom. This is very similar in structure to the heme group found in hemoglobin, except that in heme the central atom is iron, whereas in chlorophyll it is magnesium.

It is usually easy to tell when a food has significant amounts of chlorophyll, because chlorophyll provides the green color that is found in the green parts of the plants and in many of the fruits and vegetables that are consumed. These plants and foods would not be green without their chlorophyll, since chlorophyll pigments reflect sunlight at exact appropriate wavelengths for our eyes to detect them as green. The chlorophyll a molecule actually reflects light in a blue-green range (about 685 nanometer wavelengths), while chlorophyll b reflects light in a more yellow-green color (about 735 nanometer wavelengths). The overall effect, however, is a color that one would simply call "green."

All green plants contain chlorophyll a, and most vegetables that are eaten contain both chlorophyll a and chlorophyll b, while in many of them, there is slightly more chlorophyll a than chlorophyll b and this slight edge in favor of chlorophyll a tends to decrease as the plant ages. Some vegetables contain particularly high amounts of total chlorophyll. Best studied of all the vegetables is spinach containing about 300-600 milligrams per ounce.

Among vegetables consumed around the world—asparagus, green bell peppers, broccoli, Brussels sprouts, green cabbage, celery, collard greens, green beans, green peas, kale, leeks, green olives, parsley, romaine lettuce, sea vegetables, spinach, Swiss chard, and turnip greens are concentrated sources of chlorophyll.

Research on the health benefits of chlorophyll has focused on the area of cancer. This research got underway when damage to genes by carcinogenic substances called aflatoxins, was found to be prevented by chlorophyllin, a derivative of chlorophyll. Research studies in humans (Egner et al. 2001 and 2003, Jubert et al. 2009) have found that damage to DNA by aflatoxin can be decreased as much as 55% through supplementation with chlorophyllin at 100 milligrams, three times a day, for four months. This amount of chlorophyllin, 300 milligrams per day, is the same amount of chlorophyll found in one weighted ounce of spinach (a little over ½ cup of chopped raw spinach). Although research is still in the early stage, prevention and treatment of liver cancer, skin cancer, and colon cancer are all being investigated in relationship to intake of chlorophyll-containing vegetables and supplementation with chlorophyllin.

Another study by Chernomorsky and his colleagues (Chernomorsky et al. 1999) addressed the preventive effect of chlorophyll and derivatives. The growing body of epidemiological and experimental evidence associating diets rich in fruits and vegetables with prevention of chronic diseases such as cancer has stimulated interest in plant food phytochemicals as physiologically active dietary components. Chlorophyll and its various derivatives are believed to be among the family of phytochemical compounds that are potentially responsible for such associations. Dietary chlorophyll is predominantly composed of lipophilic derivatives including chlorophyll a and b (fresh fruits and vegetables), metal-free pheophytins and pyropheophytins (thermally processed fruits and vegetables), as well as Zn-pheophytins and Zn-pyropheophytins (thermally processed green vegetables). Although the use of chlorophyll derivatives in traditional medical applications is well documented, it is perhaps the potential of chlorophyll as a cancer preventative agent that has drawn significant attention recently. Biological activities attributed to chlorophyll derivatives consistent with cancer prevention include antioxidant and antimutagenic activity, mutagen trapping, modulation of xenobiotic metabolism, and induction of apoptosis. Recent research efforts have also included investigation of the impact of digestive factors on chlorophyll structure and bioaccessibility as a means to better understand the extent to which these pigments may be bioavailable in humans and therefore may have more systemic impact in the prevention of cancer (Ferruzzi and Blakeslee, 2007).

It has been recognized that the perception of food products, particularly fresh vegetables, is highly impacted by the color of the said product. In vegetable products like pepper or tomato, intensity of red color can be perceived as a sign of intense flavor while the green color as seen for salad, broccoli and green pepper is perceived as a sign of freshness and healthiness of the product. Indeed, the greener is the product, the fresher and healthier it is perceived.

The plant pigments lutein and zeaxanthin are antioxidants. Good sources of lutein and zeaxanthin include a variety of vegetables as well as other foods. Fresh, raw foods are best when it comes to getting the most nutrition per serving.

A study conducted by the Journal of the American College of Nutrition in 2004 concluded that "There is a continuously growing body of evidence that suggests that lutein and zeaxanthin may contribute to the protection against several age-related diseases, including cataract and age-related macular degeneration as well as other diseases including dementia." Vegetables are by far the greatest source of lutein and zeaxanthin. Leafy greens such as romaine, spinach, Swiss chard, turnip greens, kale, collard greens, watercress and parsley top the content list. Fresh red and orange peppers also offer suitable source of lutein. According to the American Optometric Association, both lutein and zeaxanthin are of great benefit to eye health. Along with helping to prevent age-related macular degeneration (AMD), they can also improve vision in those already afflicted with this disease; they decrease the risk of contracting cataracts too, since both of these carotenoids protect and maintain healthy cells in the eye. Other health benefits are protection of your heart and brain, and they assist the body in combating arthritis as well.

Violaxanthin maybe a metabolite or precursor of zeaxanthin depending of sun light exposure and the amount of the first one may be a good indicator of the amount of the second one.

Peppers represent a valuable source of vitamins and nutrients associated with their pigments and fruit color, including various antioxidants, carotenoids as well as chlorophyll. In the present trend of consumers looking for fresh and healthy vegetables, pepper fruits constitute a product of choice.

Peppers fruits are generally green when immature and turn generally red, orange, or yellow once mature. The color of the pepper fruits is a result of a mixture of different color components in the fruit. The color component green is provided by the presence of chloroplasts containing an abundant amount of chlorophyll. The color components red and yellow are provided by chromoplasts filled with red and yellow carotenoids, respectively. Examples of such carotenoids are capsanthin and capsorubin, lutein, beta carotene, violaxanthin and zeaxanthin. The different possible colors of the immature and mature fruits are usually a combination of different ratios between the different chlorophyll and carotenoids pigments.

In some of the markets, peppers are usually harvested green, i.e. at a non mature stage. Immature pepper fruits generally exhibit a less sweet taste as compared to red-mature-fruits.

Immature green peppers fruits can exhibit various green color variations from very pale green to dark green. Higher intensity of the green pepper color is considered as a sign of freshness and quality by consumers as well as perceived as a health attribute. It is then a continuous and vigorous trend from consumers to get green pepper fruits exhibiting a deep and intense green color.

It is therefore a need to provide pepper plants that produce pepper fruits with enhanced deep and intense green color, associated with enhanced nutritional value thanks to enhanced antioxidants, carotenoids and other healthy compounds content as well as a green color appearance that would render them attractive to the consumer, with enhanced perception of freshness and quality.

SUMMARY OF THE INVENTION

The present invention includes and provides pepper plants having extreme dark green colored pepper fruits at immature harvestable stage that also exhibit high content in pigments.

Indeed, it has been surprisingly found by the inventors of the present invention that the increase of the quantity of selected pigments such as chlorophyll A, chlorophyll B, lutein, α-carotene, β-carotene and/or violaxanthin is also accompanied by a modification of the external color perception of the pepper fruit at immature harvestable stage. The fruits of the pepper plant of the present invention thus exhibit an extreme dark green color that could be called extreme dark green or extreme green and that can be measured, for example, by colorimeter parameters, image analysis using computer vision, or by eye-measurement.

In representative embodiments, the pepper fruits of the invention are blocky type pepper fruits.

In embodiments, the pepper fruits of the invention are commercially acceptable with respect to size, shape, color, yield, and the like.

In embodiments, the pepper plants of the invention are cultivated.

According to the invention, there are also provided novel pepper cultivars designated RPP 25822, RPP 26098, RPP 26105, 8728C, 16452A, 16452B and 16452C. Thus, the invention encompasses the seeds of pepper cultivars RPP 25822, RPP 26098, RPP 26105, 8728C, 16452A, 16452B and 16452C, the plants of pepper cultivars RPP 25822, RPP 26098, RPP 26105, 8728C, 16452A, 16452B and 16452C, plant parts of the pepper cultivars RPP 25822, RPP 26098, RPP 26105, 8728C, 16452A, 16452B and 16452C (including fruits, seeds, gametes), methods of producing seed from pepper cultivars RPP 25822, RPP 26098, RPP 26105, 8728C, 16452A, 16452B or 16452C, methods for producing a pepper plant containing in its genetic material one or more transgenes, and the transgenic pepper plants produced by that method. The invention also relates to methods for producing other pepper plants derived from pepper cultivars RPP 25822, RPP 26098, RPP 26105, 8728C, 16452A, 16452B or 16452C and to pepper plants, parts thereof and seed derived by the use of those methods. The present invention further relates to pepper seeds and plants (and parts thereof including fruits) produced by crossing pepper cultivars RPP 25822, RPP 26098, or RPP 26105, 8728C, 16452A, 16452B or 16452C with itself or with another pepper plant (e.g., an F1 hybrid seed or plant).

In another aspect, the present invention provides regenerable cells for use in tissue culture of pepper cultivars RPP 25822, RPP 26098, RPP 26105, 8728C, 16452A, 16452B and 16452C. In embodiments, the tissue culture is capable of regenerating plants having all or essentially all of the physiological and morphological characteristics of the foregoing pepper plant and/or of regenerating plants having the same or substantially the same genotype as the foregoing pepper plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules, fruits and/or seeds as well as callus and/or protoplasts derived from any of the foregoing. Still further, the present invention provides pepper plants regenerated from the tissue cultures of the invention.

As a further aspect, the invention provides a method of producing pepper seed, the method comprising crossing a plant of pepper cultivar RPP 25822, RPP 26098, RPP 26105, 8728C, 16452A, 16452B or 16452C with itself or a second pepper plant. Pepper cultivars RPP 25822, RPP 26098, RPP 26105, 8728C, 16452A, 16452B and/or 16452C can be the female and/or male parent. In embodiments, the male parent is pepper cultivar 8728C. In embodiments, the female parent is pepper cultivar 16452A, 16452B or 16452C. Optionally, the method further comprises collecting the seed, which encompasses harvesting a fruit containing the seed.

The invention further provides a method of producing a progeny pepper plant, the method comprising crossing a plant of pepper cultivar RPP 25822, RPP 26098, RPP 26105, 8728C, 16452A, 16452B or 16452C with itself or a second pepper plant to produce at least a first progeny plant, which may optionally be a selfed plant or an F1 hybrid. Pepper cultivar RPP 25822, RPP 26098, RPP 26105, 8728C, 16452A, 16452B and/or 16452C can be the female and/or male parent. In embodiments, the method further comprises (a) crossing the at least first progeny plant with itself or a second plant to produce a seed of a progeny plant of a subsequent generation; (b) growing a progeny plant of a subsequent generation from said seed and crossing the progeny plant of a subsequent generation with itself or a second plant to produce a progeny plant of a further subsequent generation; and (c) optionally repeating steps (a) and (b) one or more time to produce a pepper plant further derived from pepper variety RPP 25822, RPP 26098, RPP 26105, 8728C, 16452A, 16452B or 16452C, wherein the progeny plant of a further subsequent generation of step (b) is used in place of the first progeny plant in step (a).

Another aspect of the invention provides methods for producing hybrids and other pepper plants derived from pepper cultivars RPP 25822, RPP 26098, RPP 26105, 8728C, 16452A, 16452B and 16452C. Pepper plants derived by the use of those methods are also part of the invention as well as plant parts, seed, gametes and tissue culture from such hybrid or derived pepper plants.

In representative embodiments, a pepper plant derived from pepper cultivar RPP 25822, RPP 26098, RPP 26105, 8728C, 16452A, 16452B or 16452C comprises cells comprising at least one set of chromosomes derived from pepper cultivar RPP 25822, RPP 26098, RPP 26105, 8728C, 16452A, 16452B or 16452C. In embodiments, a pepper plant or population of pepper plants derived from pepper cultivar RPP 25822, RPP 26098, RPP 26105, 8728C, 16452A, 16452B or 16452C comprises, on average, at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from pepper cultivar RPP 25822, RPP 26098, RPP 26105, 8728C, 16452A, 16452B or 16452C, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar RPP 25822, RPP 26098, RPP 26105, 8728C, 16452A, 16452B or 16452C. In embodiments, the pepper plant derived from pepper cultivar RPP 25822, RPP 26098, RPP 26105, 8728C, 16452A, 16452B or 16452C is one, two, three, four, five or more breeding crosses removed from pepper cultivar RPP 25822, RPP 26098, RPP 26105, 8728C, 16452A, 16452B or 16452C.

In embodiments, a hybrid or derived plant from pepper cultivar RPP 25822, RPP 26098, RPP 26105, 8728C, 16452A, 16452B or 16452C comprises a desired added trait(s). In representative embodiments, a pepper plant derived from pepper cultivar RPP 25822, RPP 26098, RPP 26105, 8728C, 16452A, 16452B or 16452C comprises some or all of the morphological and physiological characteristics of pepper cultivar RPP 25822, RPP 26098, RPP 26105, 8728C, 16452A, 16452B or 16452C (e.g., as described herein, in particular, in any one or more of Tables 1-9 or FIGS. 1-30). In embodiments, the pepper plant derived from pepper cultivar RPP 25822, RPP 26098, RPP 26105, 8728C, 16452A, 16452B or 16452C comprises essentially all of the morphological and physiological characteristics of pepper cultivar RPP 25822, RPP 26098, RPP 26105, 8728C, 16452A, 16452B or 16452C (e.g., as described herein, in particular, in any one or more of Tables 1-9 or FIGS. 1-30), with the addition of a desired added trait(s).

The invention also relates to methods for producing a pepper plant comprising in its genetic material one or more transgenes and to the transgenic pepper plant produced by those methods (and progeny pepper plants comprising the transgene). Also provided are plant parts, seed and tissue culture from such transgenic pepper plants, optionally wherein one or more cells in the plant part, seed, or tissue culture comprises the transgene. The transgene can be introduced via plant transformation and/or breeding techniques.

In another aspect, the present invention provides for single gene converted plants of pepper cultivar RPP 25822, RPP 26098, RPP 26105, 8728C, 16452A, 16452B or 16452C. Plant parts, seed, and tissue culture from such single gene converted plants are also contemplated by the present invention. The single transferred gene may be a dominant or recessive allele. In representative embodiments, the single transferred gene confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease including resistance to *Xanthomonas campestris* pv. *Vesicatoria* [e.g., race 6]), male fertility, enhanced nutritional quality, improved appearance (e.g., color), improved salt tolerance, industrial usage, or any combination thereof. The single gene may be a naturally occurring pepper gene or a transgene introduced into pepper through genetic engineering techniques.

The invention further provides methods for developing pepper plants in a pepper plant breeding program using plant breeding techniques including, for example, recurrent selection, backcrossing, pedigree breeding, doubled haploid techniques, restriction fragment length polymorphism enhanced selection, genetic marker enhanced selection and/or transformation. Seeds, pepper plants, and parts thereof, produced by such breeding methods are also part of the invention.

The invention also provides methods of multiplication or propagation of pepper plants of the invention, which can be accomplished using any method known in the art, for example, via vegetative propagation and/or seed.

The invention further provides a method of producing food or feed comprising (a) obtaining a pepper plant of the invention, optionally wherein the plant has been cultivated to maturity, and (b) collecting at least one pepper plant or part thereof (e.g., fruits, seeds) from the plant. In embodiments, obtaining a pepper plant comprises growing the plant.

Additional aspects of the invention include harvested products and processed products from the pepper plants of the invention. A harvested product can be a whole plant or any plant part, as described herein. Thus, in some embodiments, a non-limiting example of a harvested product includes a seed or a fruit.

In representative embodiments, a processed product includes, but is not limited to: dehydrated, cut, sliced, chopped, diced, ground, pureed, dried, canned, jarred, washed, brined, packaged, refrigerated, frozen, blanched and/or heated fruits and/or seeds of the pepper plants of the invention, or any other part thereof. In embodiments, a processed product includes a sugar or other carbohydrate, fiber, protein, pigment (e.g., a carotenoid) and/or aromatic compound that is extracted, purified or isolated from a pepper plant of the invention. In embodiments, the processed product includes washed and packaged fruits (or parts thereof) of the invention, for example, cut, sliced or diced and in a frozen form.

Thus, the invention also provides a method of producing a processed product from a plant of the invention, the method comprising (a) obtaining a fruit of a plant of the invention; and (b) processing the fruit to produce a processed product. In embodiments, processing comprises slicing, cutting, dicing, dehydrating, pureeing, blanching and/or freezing.

In representative embodiments, the invention provides a seed of a pepper plant of the invention. In embodiments, the invention is directed to seed that produces the pepper plants of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

As a further aspect, the invention provides a plant of pepper cultivar RPP 25822, RPP 26098, RPP 26105, 8728C, 16452A, 16452B or 16452C.

As an additional aspect, the invention provides a pepper plant, or a part thereof, having all or essentially all of the physiological and morphological characteristics of a plant of pepper cultivar RPP 25822, RPP 26098, RPP 26105, 8728C, 16452A, 16452B or 16452C.

As another aspect, the invention provides fruits and/or seed of the pepper plants of the invention and a processed product from the fruits and/or seed of the inventive pepper plants.

As still another aspect, the invention provides a method of producing pepper seed, the method comprising crossing a pepper plant of the invention with itself or a second pepper plant. The invention also provides seed produced by this method and plants produced by growing the seed.

As yet a further aspect, the invention provides a method for producing a seed of a pepper plant derived from pepper cultivar RPP 25822, RPP 26098, RPP 26105, 8728C, 16452A, 16452B or 16452C, the method comprising: (a) crossing a pepper plant of pepper cultivar RPP 25822, RPP 26098, RPP 26105, 8728C, 16452A, 16452B or 16452C with a second pepper plant; and (b) allowing seed of a pepper plant derived from pepper cultivar RPP 25822, RPP 26098, RPP 26105, 8728C, 16452A, 16452B or 16452C to form. In embodiments, the method further comprises: (c) growing a plant from the seed derived from pepper cultivar RPP 25822, RPP 26098, RPP 26105, 8728C, 16452A, 16452B or 16452C of step (b); (d) selfing the plant grown from the pepper seed derived from pepper cultivar RPP 25822, RPP 26098, RPP 26105, 8728C, 16452A, 16452B or 16452C or crossing it to a second pepper plant to form additional pepper seed derived from pepper cultivar RPP 25822, RPP 26098, RPP 26105, 8728C, 16452A, 16452B or 16452C and (e) optionally repeating steps (c) and (d) one or more times to generate further derived pepper seed from pepper cultivar RPP 25822, RPP 26098, RPP 26105, 8728C, 16452A, 16452B or 16452C, wherein a plant grown from the additional pepper seed of step (d) is used in place of the plant grown from the seed derived from pepper cultivar RPP 25822, RPP 26098, RPP 26105, 8728C, 16452A, 16452B or 16452C of step (b). Optionally, the method comprises: (e) repeating steps (c) and (d) one or more times (e.g., one to three, one to five, one to six, one to seven, one to ten, three to five, three to six, three to seven, three to eight or three to ten times) to generate further derived pepper plants and seed. As another option, the method can comprise collecting the seed, which includes collecting a fruit comprising the seed. The invention also provides seed produced by these methods and plants produced by growing the seed.

As another aspect, the invention is also directed to a method of producing a pepper fruit comprising obtaining a plant according to the instant invention and harvesting a fruit from the plant. In embodiments, obtaining a plant of the invention comprises growing the plant to produce a fruit.

Still further, as another aspect, the invention provides a method of vegetatively propagating a plant of pepper cultivar RPP 25822, RPP 26098, RPP 26105, 8728C, 16452A, 16452B or 16452C. In a non-limiting example, the method comprises: (a) collecting tissue capable of being propagated from a plant of pepper cultivar RPP 25822, RPP 26098, RPP 26105, 8728C, 16452A, 16452B or 16452C; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into pepper cultivar RPP 25822, RPP 26098, RPP 26105, 8728C, 16452A, 16452B or 16452C, the method comprising: (a) crossing a first plant of pepper cultivar RPP 25822, RPP 26098, RPP 26105, 8728C, 16452A, 16452B or 16452C with a second pepper plant that comprises a desired trait to produce F1 progeny; (b) selecting an F1 progeny that comprises the desired trait; (c) crossing the selected F1 progeny with pepper cultivar RPP 25822, RPP 26098, RPP 26105, 8728C, 16452A, 16452B or 16452C to produce backcross progeny; and (d) selecting backcross progeny comprising the desired trait to produce a plant derived from pepper cultivar RPP 25822, RPP 26098, RPP 26105, 8728C, 16452A, 16452B or 16452C comprising a desired trait. In embodiments, the selected progeny has one or more of the characteristics of RPP 25822, RPP 26098, RPP 26105, 8728C, 16452A, 16452B or 16452C (e.g., as described herein, in particular, in any one or more of Tables 1-9 or FIGS. 1-30). In embodiments, the selected progeny comprises all or essentially all the morphological and physiological characteristics of the first plant of pepper cultivar RPP 25822, RPP 26098, RPP 26105, 8728C, 16452A, 16452B or 16452C. Optionally, the method further comprises: (e) repeating steps (c) and (d) one or more times to produce a plant derived from pepper cultivar RPP 25822, RPP 26098, RPP 26105, 8728C, 16452A, 16452B or 16452C comprising a desired added trait and essentially all of the physiological and morphological characteristics of the pepper cultivar RPP 25822, RPP 26098, RPP 26105, 8728C, 16452A, 16452B or 16452C, wherein the selected backcross progeny produced in step (d) is used in place of the selected F1 progeny in step (c).

In representative embodiments, the invention also provides a method of producing a plant of pepper cultivar RPP 25822, RPP 26098, RPP 26105, 8728C, 16452A, 16452B or 16452C comprising a desired added trait, the method comprising introducing a transgene or locus conferring the desired trait into a plant of pepper cultivar RPP 25822, RPP 26098, RPP 26105, 8728C, 16452A, 16452B or 16452C. The transgene can be introduced by transformation methods (e.g., genetic engineering) or breeding techniques. In embodiments, the plant comprising the transgene or locus has one or more of the morphological and physiological characteristics of RPP 25822, RPP 26098, RPP 26105, 8728C, 16452A, 16452B or 16452C (e.g., as described herein, in particular, in any one or more of Tables 1-9 or FIGS. 1-30). In embodiments, the plant comprising the transgene or locus comprises all or essentially all of the morphological and physiological characteristics of pepper cultivar RPP 25822, RPP 26098, RPP 26105, 8728C, 16452A, 16452B or 16452C.

The invention also provides pepper plants produced by the methods of the invention or a selfed progeny thereof, wherein the pepper plant has the desired added trait as well as seed from such pepper plants.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease including resistance to *Xanthomonas campestris* pv. *Vesicatoria* [e.g., race 6]), enhanced nutritional quality, increased sweetness, increased flavor, reduced cracking, improved ripening control, improved salt tolerance, industrial usage, or any combination thereof.

In representative embodiments, a transgene or locus conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene or locus conferring pest resistance (e.g., insect and/or nematode resistance) encodes a *Bacillus thuringiensis* endotoxin.

In representative embodiments, transgenic plants (e.g., using genetic engineering techniques), single gene converted plants, hybrid plants and pepper plants derived from pepper cultivar RPP 25822, RPP 26098, RPP 26105, 8728C, 16452A, 16452B or 16452C have at least 1, 2, 3, 4, 5, 6, 7, 8, 9, 10 or more of the morphological and physiological characteristics of pepper cultivar RPP 25822, RPP 26098, RPP 26105, 8728C, 16452A, 16452B or 16452C (e.g., as described herein, in particular, in any one or more of Tables 1-9 or FIGS. 1-30), or even all of the morphological and physiological characteristics of pepper cultivar RPP 25822, RPP 26098, RPP 26105, 8728C, 16452A, 16452B or 16452C, so that said plants are not significantly different for said traits than pepper cultivar RPP 25822, RPP 26098, RPP 26105, 8728C, 16452A, 16452B or 16452C as determined at the 5% significance level when grown in the same environmental conditions; optionally, with the presence of one or more desired additional traits (e.g., male sterility, disease resistance, pest or insect resistance, herbicide resistance, and the like).

The invention also encompasses plant parts, plant material, pollen, ovules, leaves, fruits and seed from the pepper plants of the invention. Also provided is a tissue culture of regenerable cells from the pepper plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith, fruits and/or capsules; or (b) callus or protoplasts derived from the cells of (a). Further provided are pepper plants regenerated from a tissue culture of the invention.

The invention also contemplates methods of determining the genotype of a plant of the invention, the method comprising obtaining nucleic acids from the plant and detecting a plurality of polymorphisms in the nucleic acids. Optionally, the results are stored on a computer readable medium.

In representative embodiments is provided a cultivated *Capsicum annuum* plant producing pepper fruits, particularly a blocky type pepper plant producing blocky type pepper fruits exhibiting extreme dark green color at immature harvestable stage as described and characterized herein.

The present invention also includes and provides methods of introgressing one or more (e.g., two), extreme dark green pepper fruit QTL allele(s) into a pepper plant comprising:
a) crossing a plant from a first pepper plant as a first parent having one or more extreme dark green pepper fruit allele(s) with a second pepper plant as a second parent aiming to form a population segregating for dark green immature fruit color,
b) phenotyping the population aiming to select plants with darker immature fruit color having one or more extreme dark green fruit QTL allele(s),
c) screening the segregating population for a member having one or more extreme dark green pepper fruit QTL allele using (a) nucleic acid molecule(s) capable of identifying (an) extreme dark green allele(s),
and
d) selecting a pepper plant that contains the one or more extreme dark green allele(s) at (a) QTL for further crossing.

In representative embodiments, the present invention further includes and provides methods of producing a pepper plant bearing extreme dark green pepper fruits comprising:
a) providing a pepper plant as a first parent;
b) crossing the first parent with a second pepper plant according to the present invention;
c) growing pepper plant seed produced by the cross to yield a progeny pepper plant bearing fruits;
d) determining the L* value of the surface and/or flesh, chlorophyll a content, chlorophyll b content, lutein content, violaxanthin content, or any combination of the foregoing, for the pepper fruits of progeny pepper plants of c;
e) selecting the progeny pepper plant(s) that has extreme dark green pepper fruits as indicated by one or more of the parameters in (d) at the immature harvestable stage as described herein.

Still further, in representative embodiments, the invention provides a method of providing a pepper plant producing pepper fruits exhibiting an increased content of chlorophyll a, chlorophyll b, lutein and/or violaxanthin, comprising the steps of:
a) providing a pepper population segregating for dark green immature fruit color,
b) screening the segregating population for a member having an extreme dark green pepper fruit trait, wherein said trait can be identified by the presence of one or more of the following molecular markers in the genome: SP436, SP626, SP693 and SP694; and
c) selecting at least one member of the segregating population, wherein said at least one member is bearing an extreme dark green pepper fruit trait.

The present invention also includes and provides a pepper plant bearing extreme dark green color fruit at immature harvestable stage, said plant comprising one or more (e.g., two) genetic determinants directing or controlling expression of said extreme dark green color in the pepper fruit of the pepper plant, wherein said genetic determinant(s) are obtainable from a pepper plant source, particularly from *Capsicum annuum*, particularly from *Capsicum annuum* 8728C, RPP 25822, RPP 26098, RPP 26105, 8728C, 16452A, 16452B or 16452C. In embodiments, the pepper plant is homozygous for the genetic determinant(s).

In representative embodiments, the genetic determinant(s) that controls the expression of the extreme dark green color in the pepper fruits also controls the color and pigment/nutritional characteristics associated with the extreme dark green color trait as described herein.

In representative embodiments, the present invention further includes and provides methods of identifying a pepper plant bearing extreme dark green color pepper fruits at immature harvestable stage, the method comprising:
a) providing a population segregating for extreme dark green immature fruit color,
b) screening the segregating population for a member having an extreme dark green pepper fruit trait, wherein said trait can be identified by the presence of one or more of the following molecular markers in the genome: SP436, SP626, SP693 and/or SP694,
c) selecting at least one member of the segregating population, wherein said at least one member is bearing one extreme dark green pepper fruit trait and comprises the molecular marker(s) of b).

As still another aspect, the invention provides methods of producing a pepper plant bearing extreme dark green color fruit at immature harvestable stage, comprising the step of transferring at least one genetic determinant directing or controlling expression of said extreme dark green color in the pepper fruit of the pepper plant from a donor pepper plant bearing extreme dark green color fruit at immature harvestable stage to a recipient pepper plant that does not bear extreme dark green fruit at immature harvestable stage, optionally wherein said transfer of said genetic determinant is performed by transformation, by crossing, by protoplast fusion, by a doubled haploid technique or by embryo rescue, and wherein said at least one genetic determinant is represented by at least one QTL or a functional part thereof that directs or controls expression of said dark green immature fruit color in the pepper fruit of the pepper plant, wherein the at least one QTL or a functional part thereof is genetically or physically linked to a marker locus that co-segregates with the extreme dark green color and is selected from one or more of: SP436, SP626, SP693 and/or SP694.

In embodiments, the method further comprises the steps of: detecting the at least one genetic determinant; and selecting a pepper plant that bears extreme dark green color fruit at immature harvestable stage and comprises said at least one genetic determinant.

In embodiments, the transfer of said genetic determinant comprises: crossing said donor pepper plant with said recipient pepper plant to produce progeny plants; and selecting from among the offspring a plant that comprises the at least one genetic determinant in its genome.

In addition to the exemplary aspects and embodiments described above, the invention is described in more detail in the description of the invention set forth below.

| Genotype | Pepper Entry | Variety |
|---|---|---|
| Non-OVG Hybrids | 1 | Crusader |
| | 2 | Encore |
| | 3 | 8302 |
| | 4 | 7141 |
| | 5 | 1819 |
| | 6 | Declaration |
| | 7 | Aristotle |
| | 8 | Karisma |
| Heterozygous OVG Hybrids | 9 | Hunter |
| | 10 | Tomcat |
| Homozygous OVG Hybrids | 11 | RPP 26098 |
| | 12 | RPP 26105 |
| OVG Inbreds | 13 | 8728C, OVG male inbred parent |
| | 14 | 16452A, OVG female inbred parent of RPP 25822 |
| | 15 | 16452A, OVG female inbred parent of RPP 26098 |
| | 16 | 16452C, OVG female inbred parent of RPP 26105 |
| Non-OVG Inbreds | 17 | Non-OVG inbred, female parent of Hunter |
| | 18 | Non-OVG inbred, female parent of Tomcat |
| | 19 | Non-OVG inbred, male parent of Encore |

Figure 1:
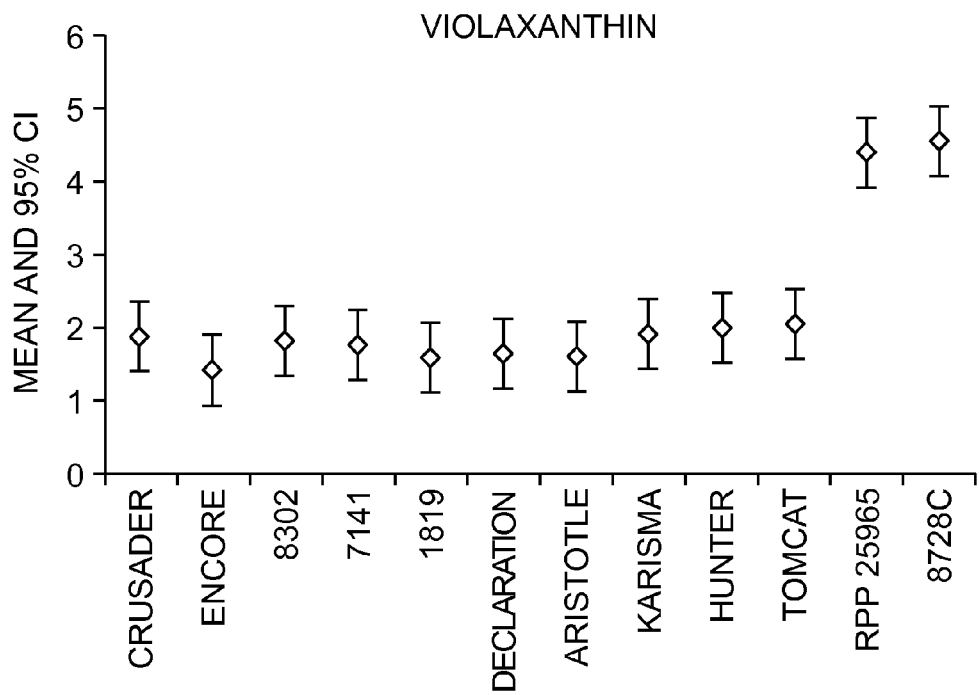
FIG. 1 shows the content in violaxanthin in μg/g of fresh (average value with 95% CI) weight for different entries that were grown in Gilroy, Calif. in summer 2010.
Figure 2:
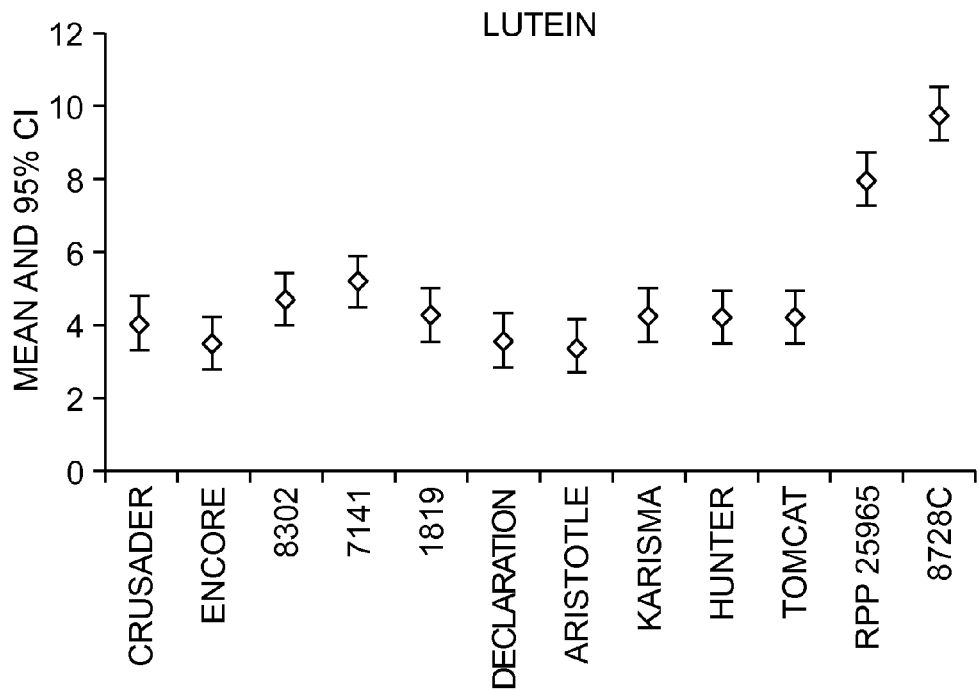
FIG. 2 shows the content in lutein in μg/g of fresh (average value with 95% CI) weight for different entries that were grown in Gilroy, Calif.
Figure 3:
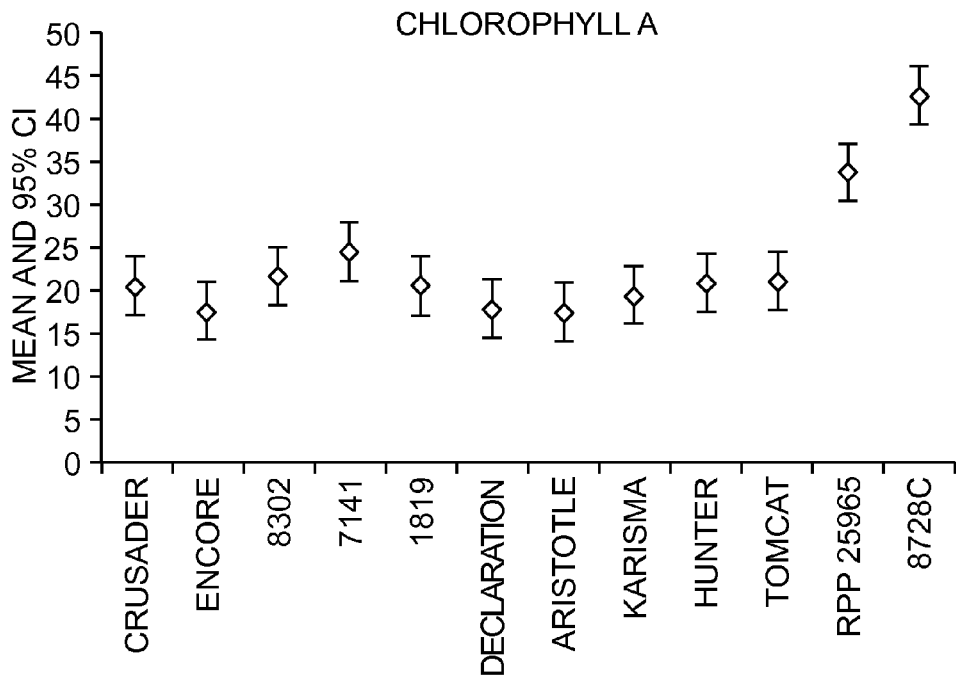
FIG. 3 shows the content in chlorophyll A in μg/g of fresh (average value with 95% CI) weight for different entries that were grown in Gilroy, Calif.
Figure 4:
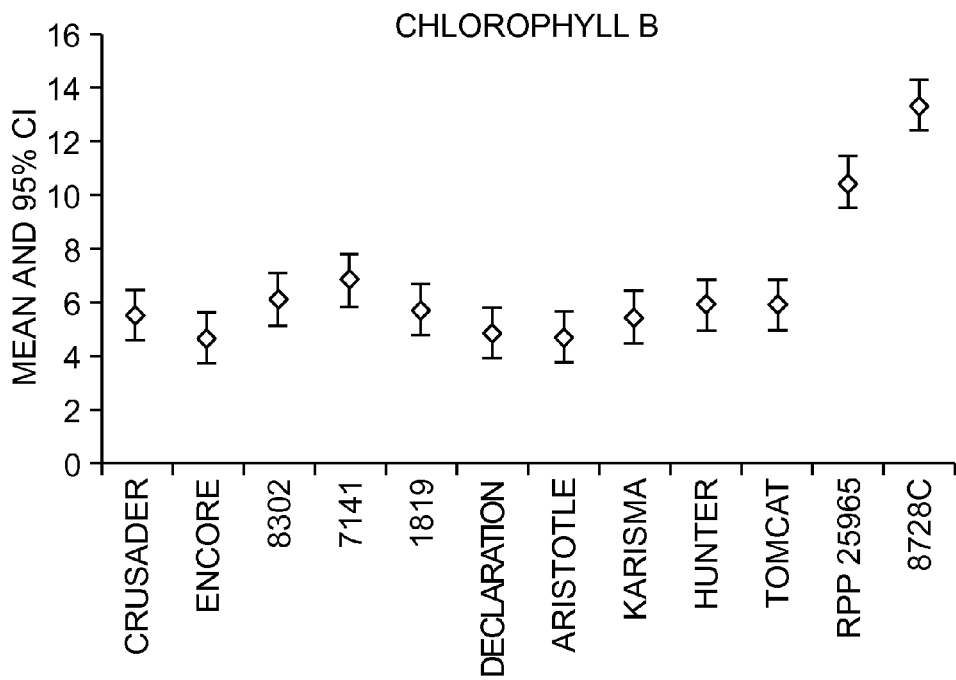
FIG. 4 shows the content in chlorophyll B in μg/g of fresh (average value with 95% CI) weight for different entries that were grown in Gilroy, Calif.
Figure 5:
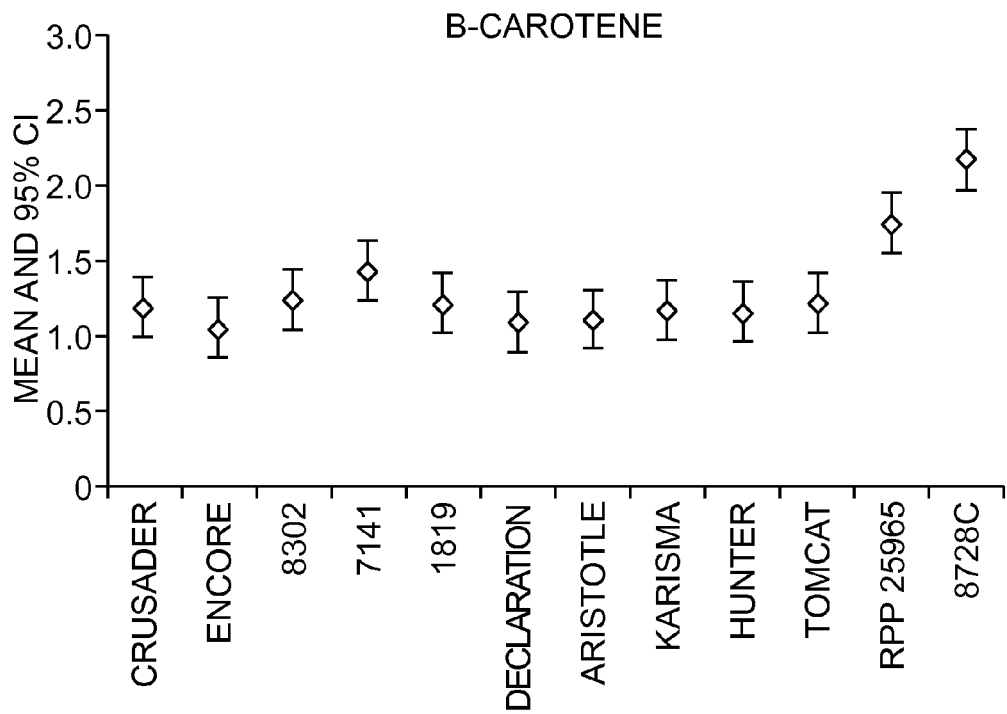
FIG. 5 shows the content in beta-carotene in μg/g of fresh (average value with 95% CI) weight for different entries that were grown in Gilroy, Calif.
Figure 6:
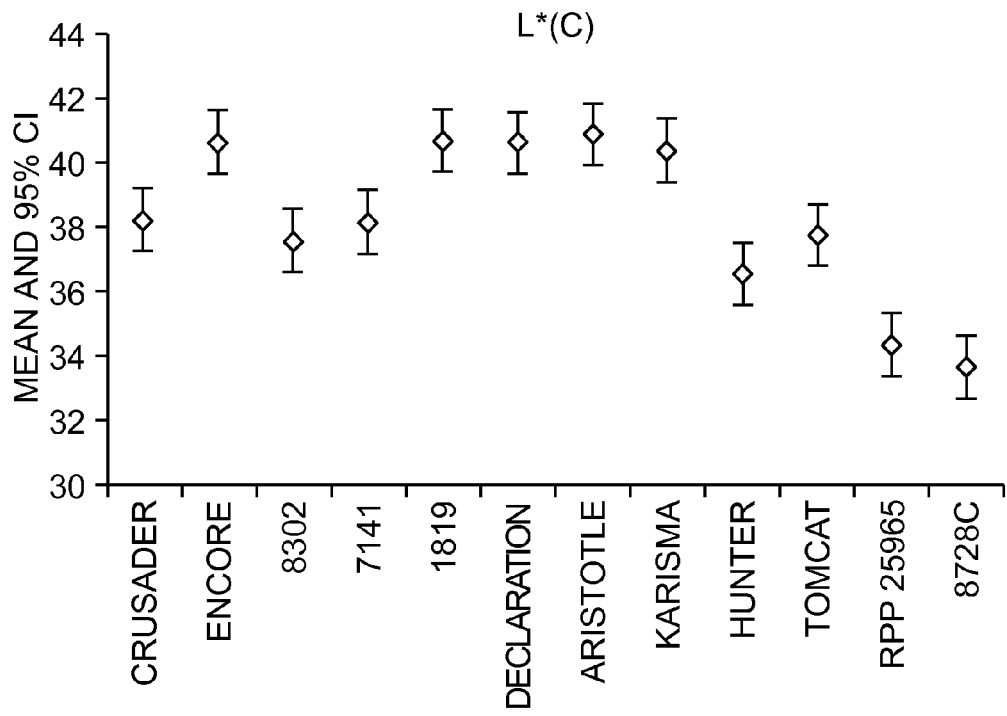
FIG. 6 shows the L* value measured by colorimeter for different entries that were grown in Gilroy, Calif.
Figure 7:
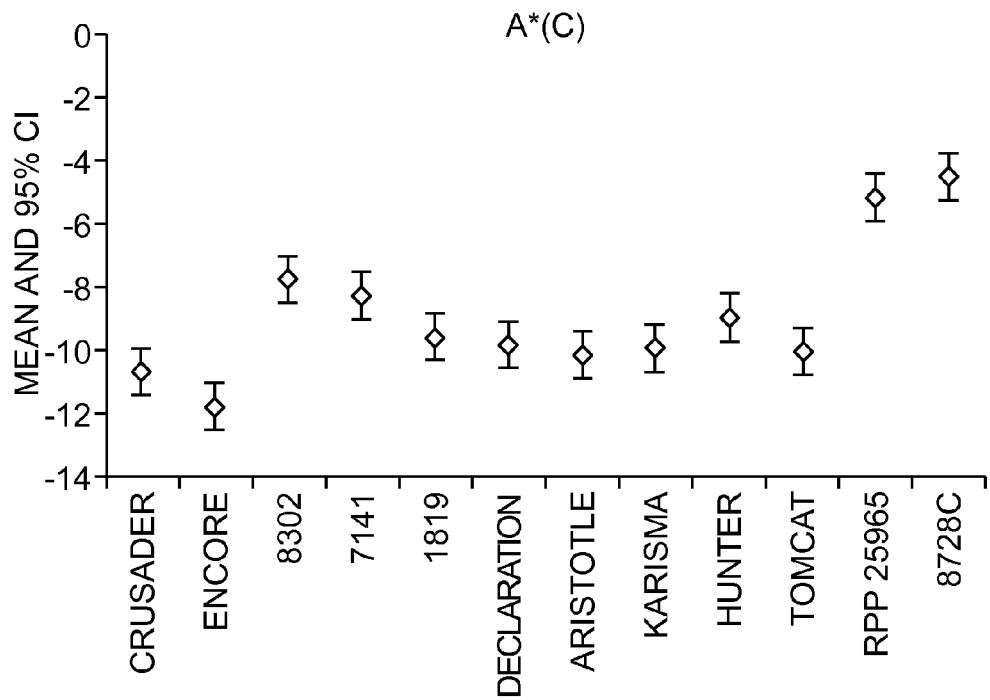
FIG. 7 shows the a* value for different entries that were grown in Gilroy, Calif.
Figure 8:
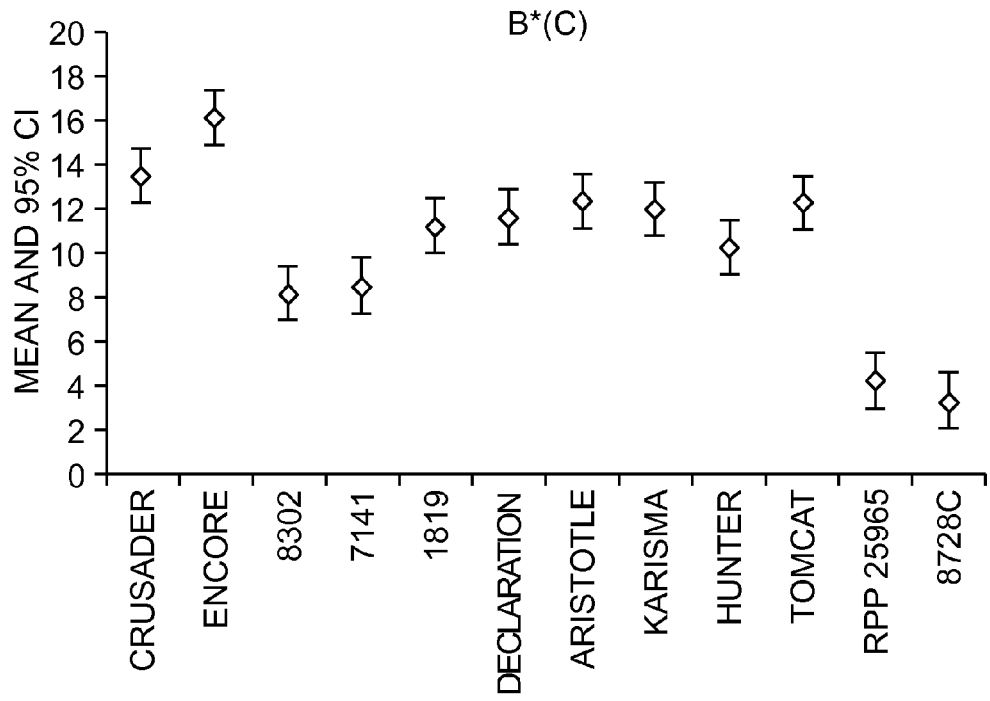
FIG. 8 shows the b* value for different entries that were grown in Gilroy, Calif.
Figure 9:
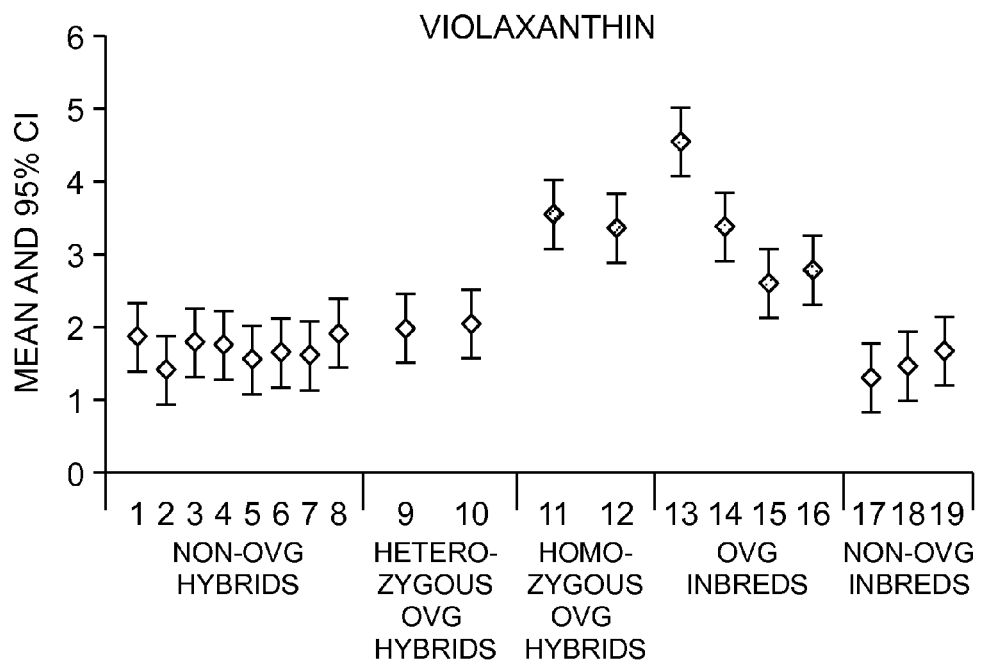
FIG. 9 shows the content in violaxanthin in μg/g of fresh weight (average value with 95% CI) for non-overgreen (OVG) hybrids, heterozygous OVG hybrids, homozygous OVG hybrids, OVG inbreds and non-OVG inbreds that were grown under standard field conditions in Gilroy, Calif. in Summer 2010 (fruit measured in August/September 2010). The different entries indicated in the figure are shown in the chart below.
Figure 10:
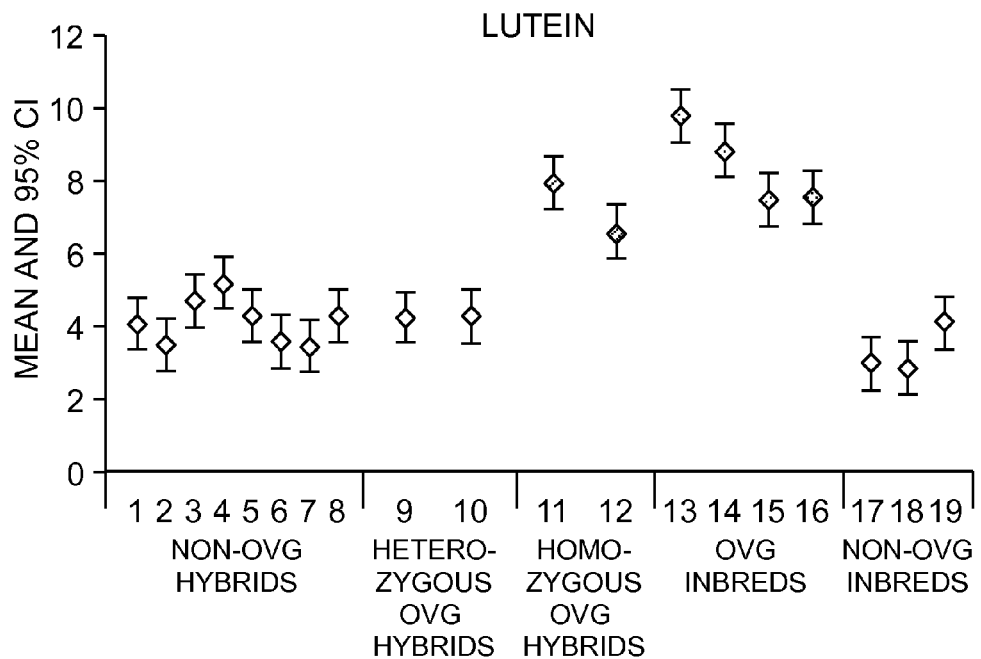

FIG. 10 shows the content in lutein in μg/g of fresh weigh (average value with 95% CI) weight for the different entries shown in FIG. 9, which were all grown under standard field conditions in Gilroy, Calif.

Figure 11:
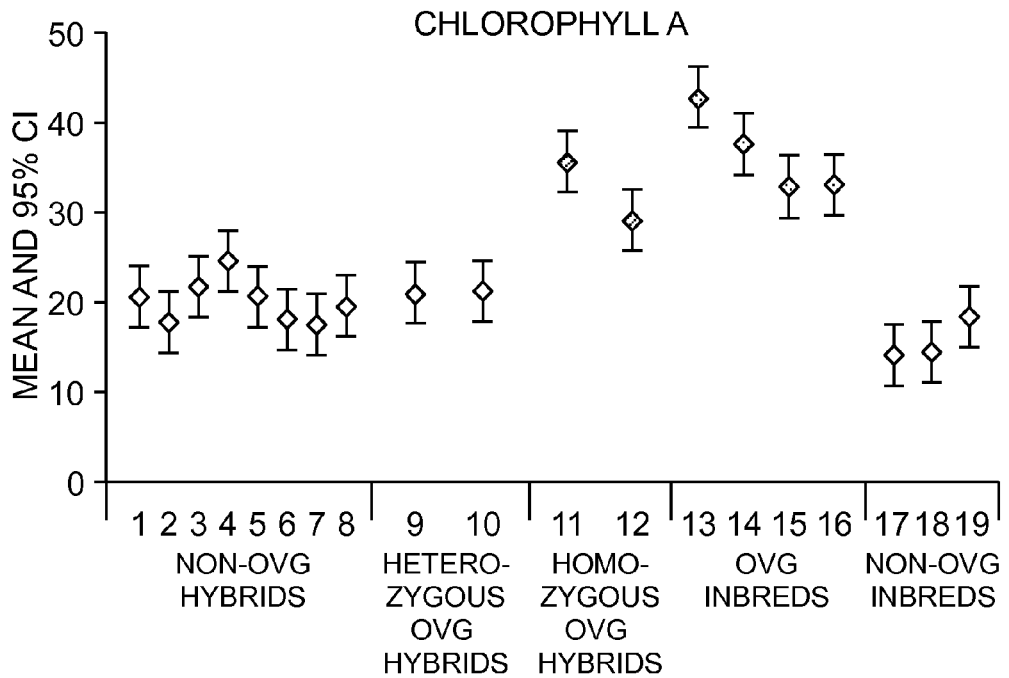

FIG. 11 shows the content in chlorophyll A in μg/g of fresh weight (average value with 95% CI) for the different entries shown in FIG. 9, which were all grown under standard field conditions in Gilroy, Calif.

Figure 12:
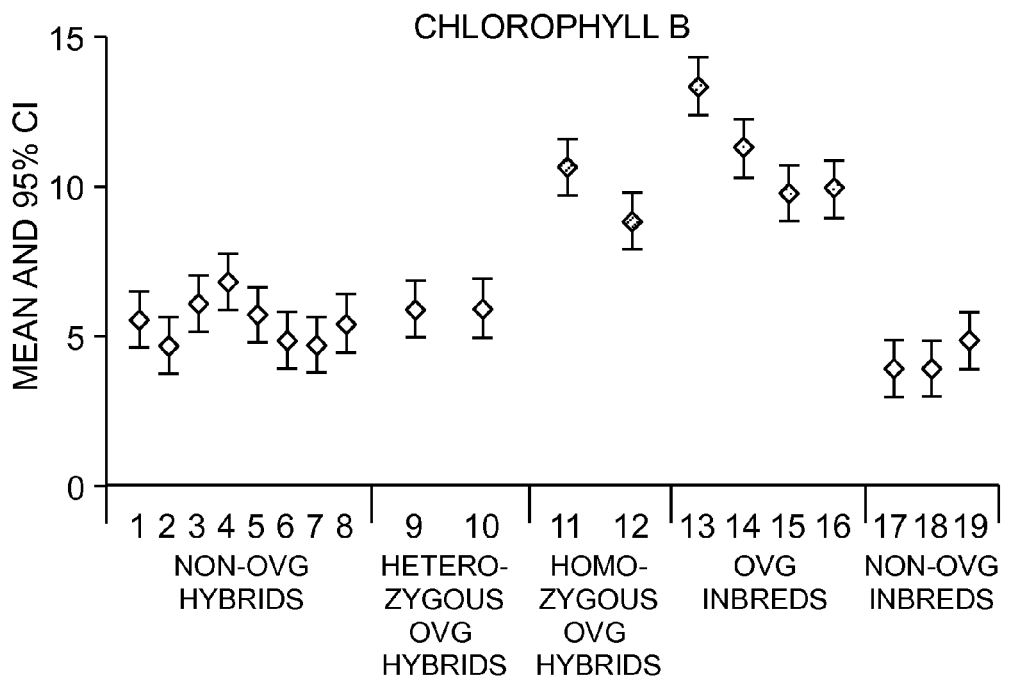

FIG. 12 shows the content in chlorophyll B in μg/g of fresh weight (average value with 95% CI) for the different entries shown in FIG. 9, which were all grown under standard field conditions in Gilroy, Calif.

Figure 13:
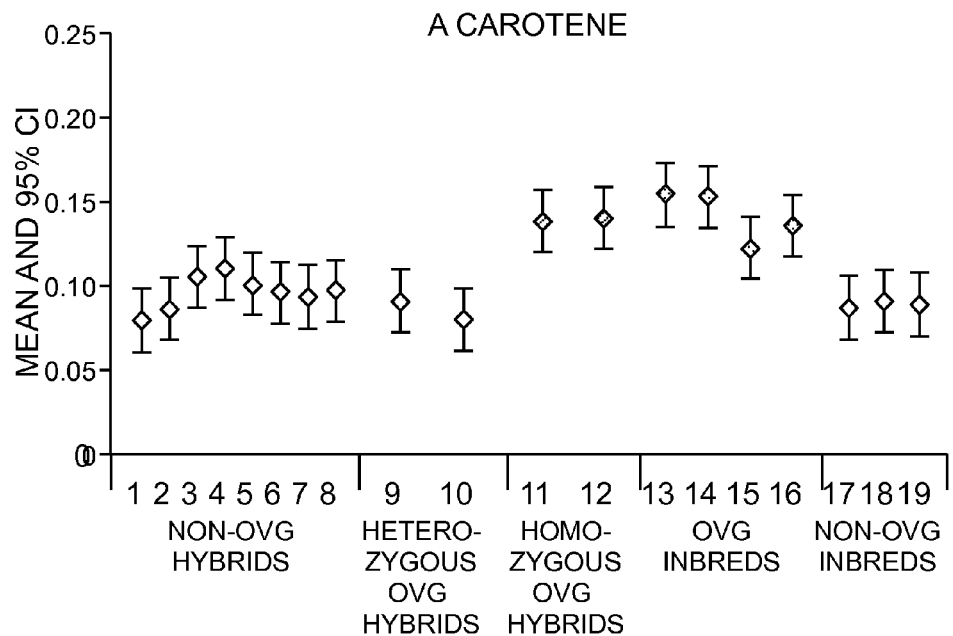

FIG. 13 shows the content in alpha-carotene in μg/g of fresh weight (average value with 95% CI) for the different entries shown in FIG. 9, which were all grown under standard field conditions in Gilroy, Calif.

Figure 14:
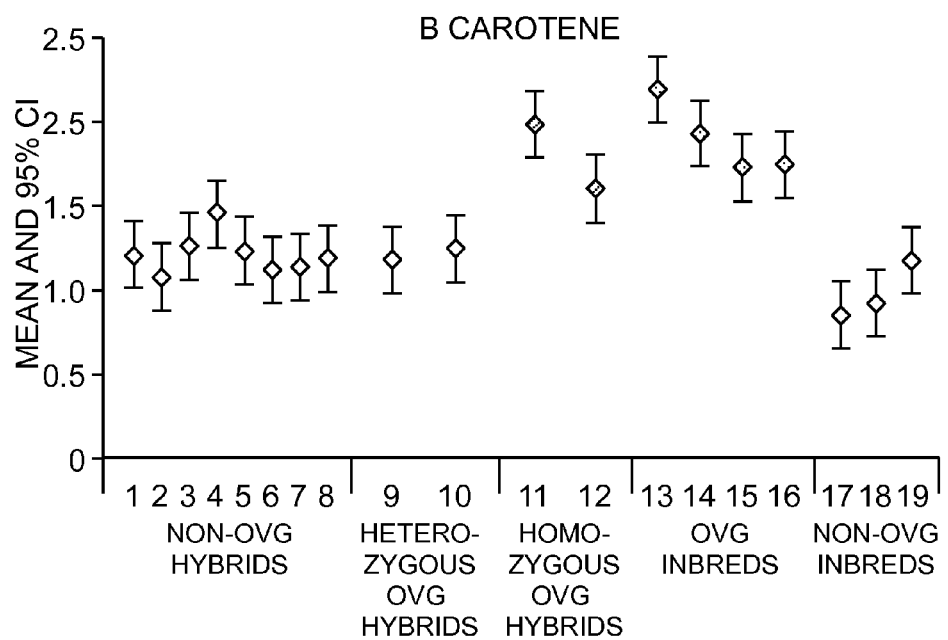

FIG. 14 shows the content in beta-carotene in μg/g of fresh (average value with 95% CI) weight for the different entries shown in FIG. 9, which were all grown under standard field conditions in Gilroy, Calif.

Figure 15:
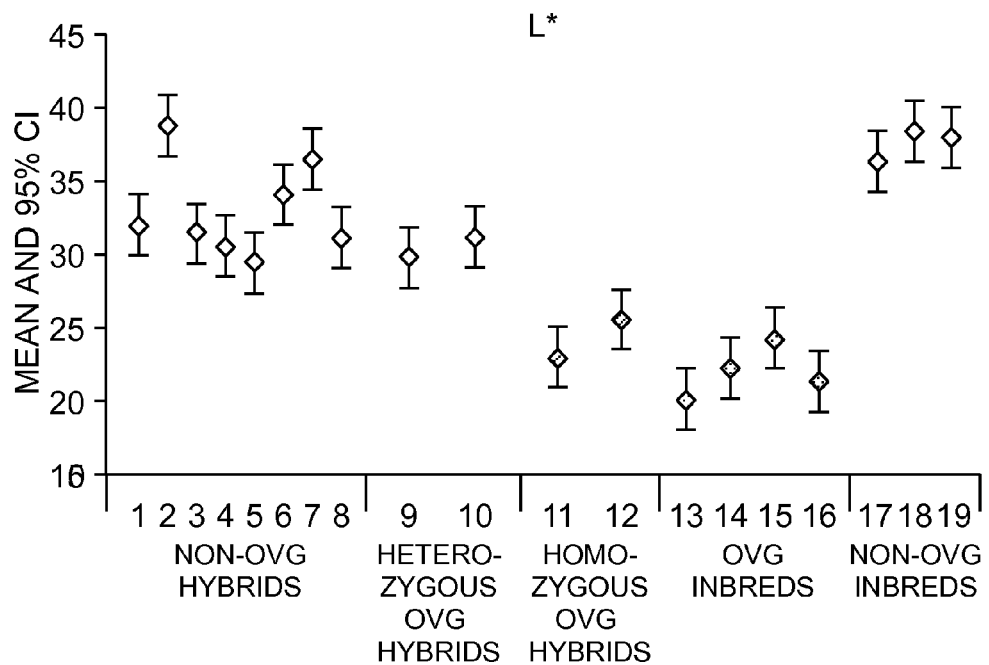

FIG. 15 shows the L* value measured by image analysis for the different entries shown in FIG. 9, which were all grown under standard field conditions in Gilroy, Calif.

Figure 16:
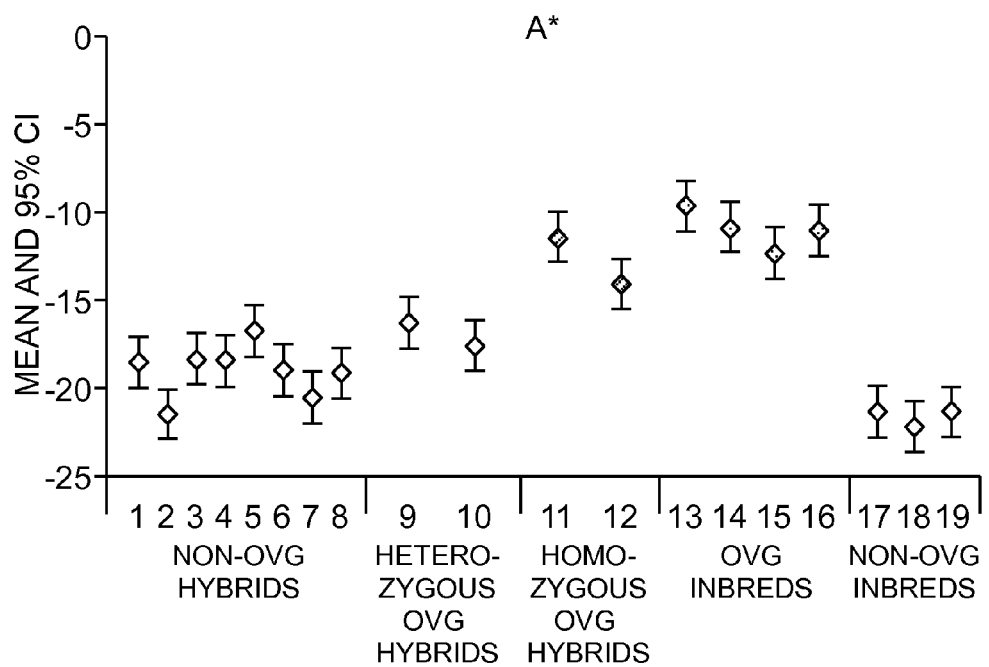

FIG. 16 shows the a* value for the different entries shown in FIG. 9, which were all grown under standard field conditions in Gilroy, Calif.

Figure 17:
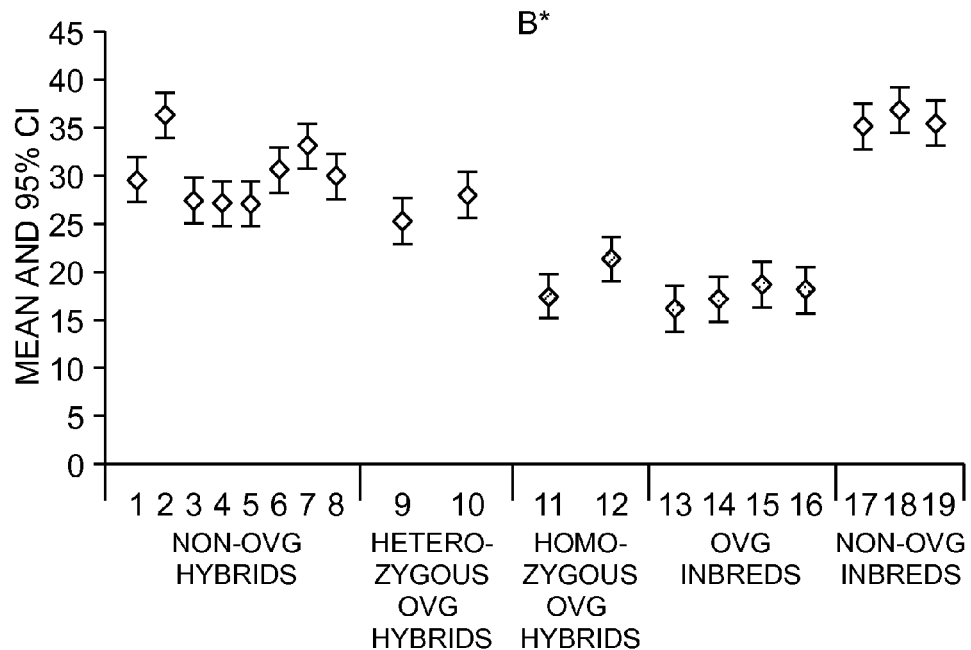

FIG. 17 shows the b* value for the different entries shown in FIG. 9, which were all grown under standard field conditions in Gilroy, Calif.

Figure 18:
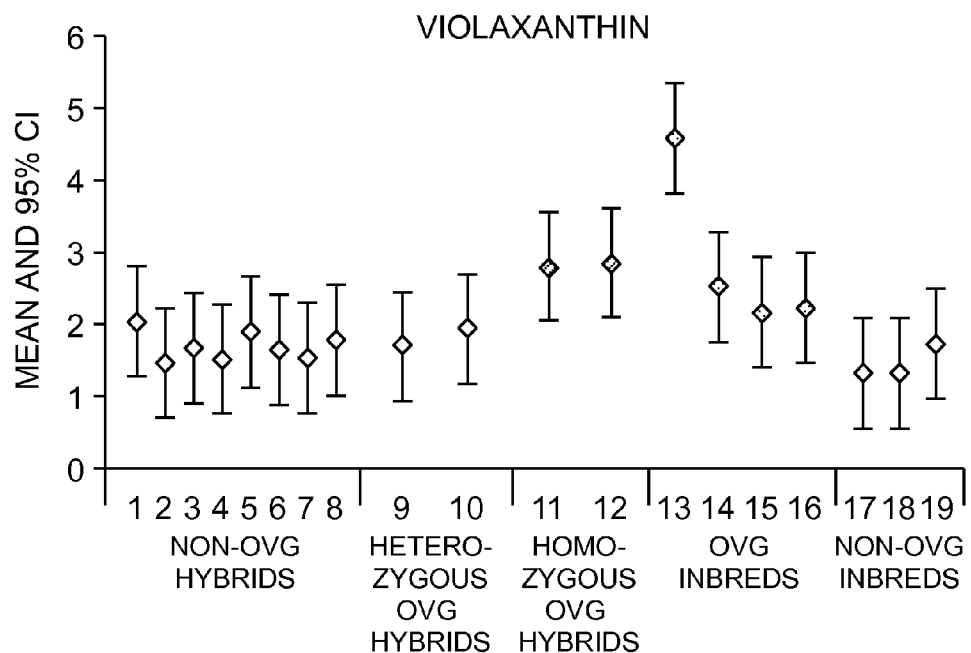

FIG. 18 shows the content in violaxanthin in μg/g of fresh weight (average value with 95% CI) for non-overgreen (OVG) hybrids, heterozygous OVG hybrids, homozygous OVG hybrids, OVG inbreds and non-OVG inbreds that were grown under standard passive greenhouse conditions in El Ejido, Spain in Winter 2010-2011 (fruits measured in January-February 2011). The pepper entries are the same as in FIG. 9.

Figure 19:
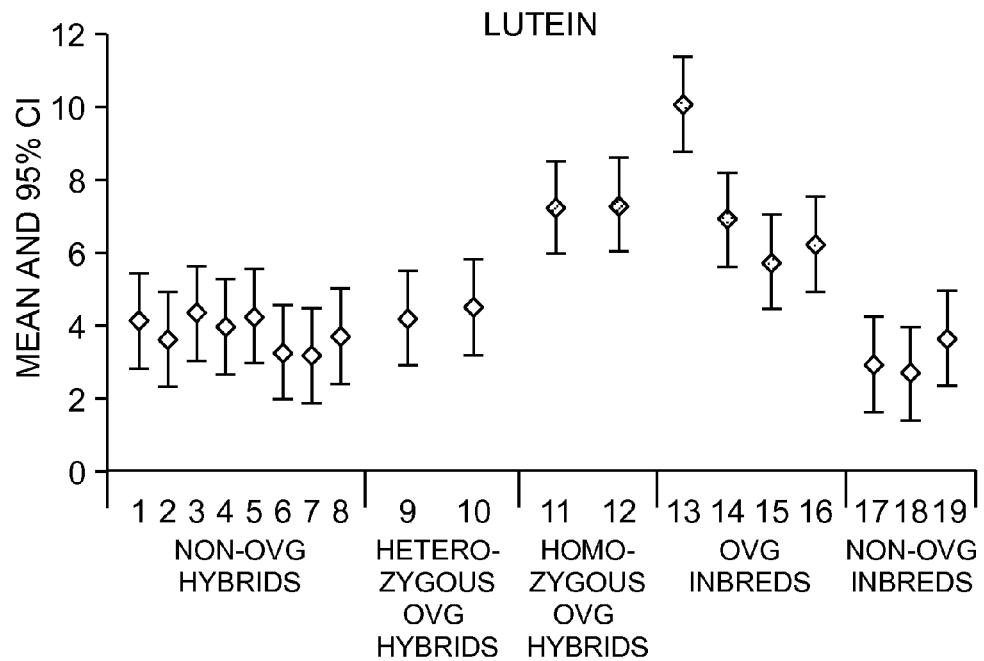

FIG. 19 shows the content in lutein in μg/g of fresh weigh (average value with 95% CI) weight for the different entries shown in FIG. 9, which were grown under standard passive greenhouse conditions in El Ejido, Spain.

Figure 20:
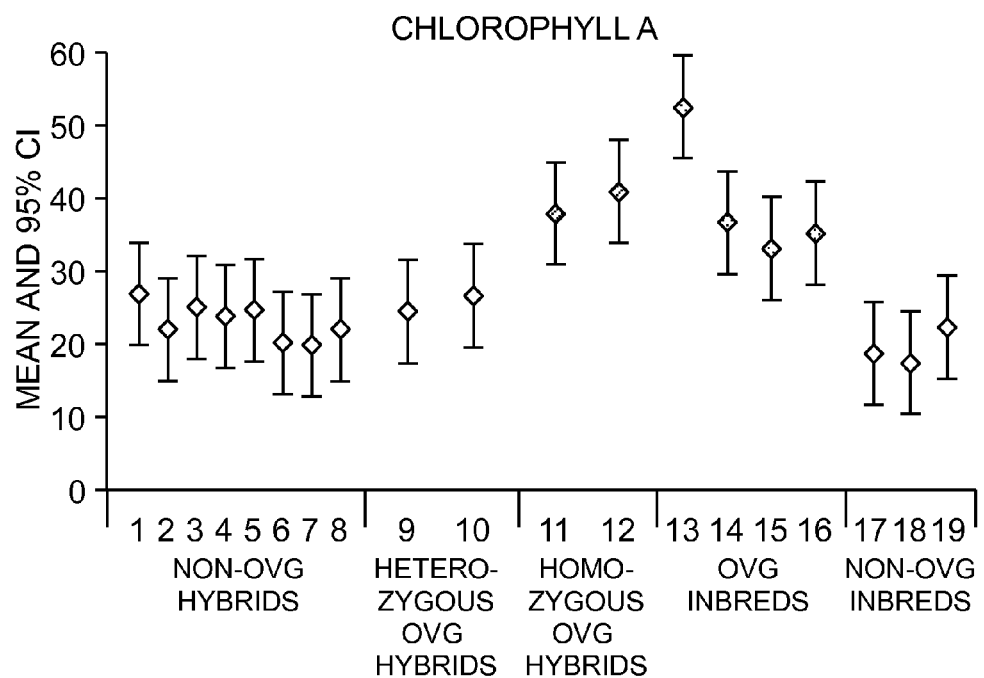

FIG. 20 shows the content in chlorophyll A in μg/g of fresh weight (average value with 95% CI) for the different entries shown in FIG. 9, which were grown under standard passive greenhouse conditions in El Ejido, Spain.

Figure 21:
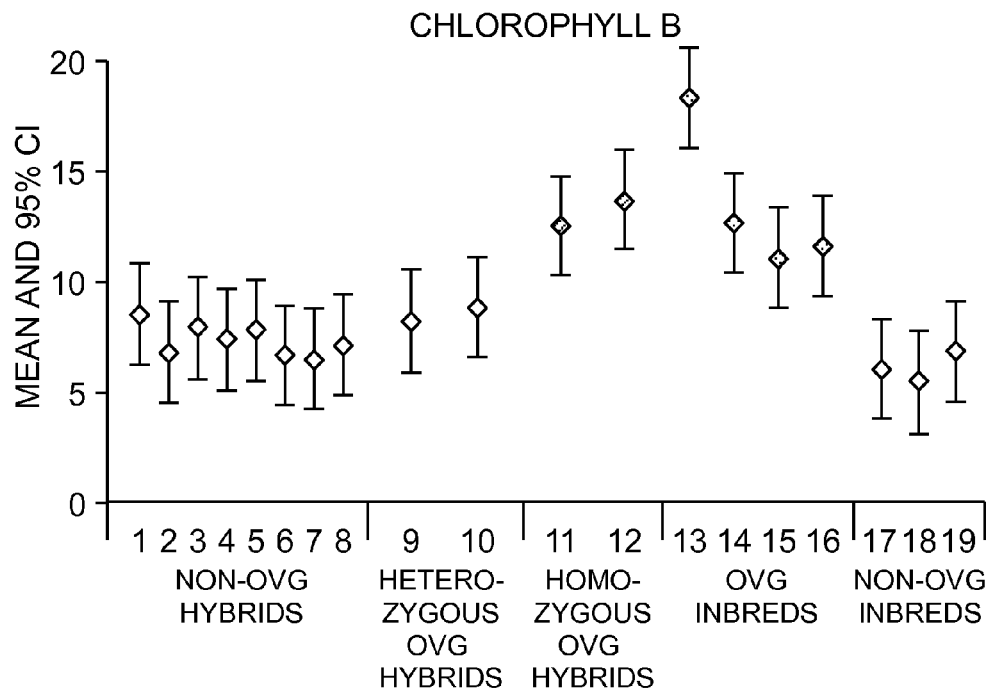

FIG. 21 shows the content in chlorophyll B in μg/g of fresh weight (average value with 95% CI) for the different entries shown in FIG. 9, which were grown under standard passive greenhouse conditions in El Ejido, Spain.

Figure 22:
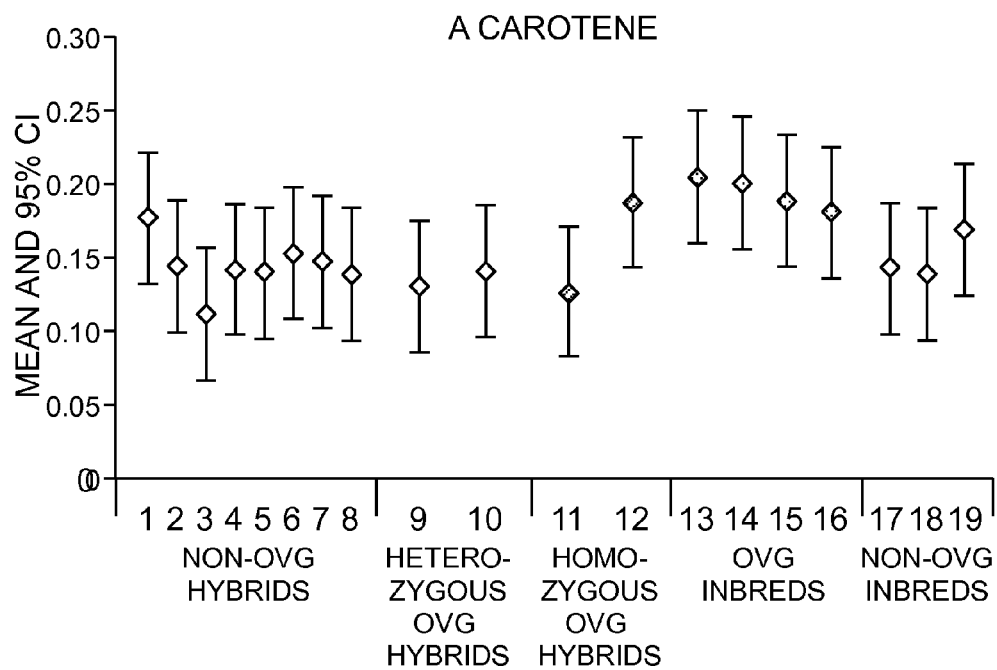

FIG. 22 shows the content in alpha-carotene in μg/g of fresh weight (average value with 95% CI) for the different entries shown in FIG. 9, which were grown under standard passive greenhouse conditions in El Ejido, Spain.

Figure 23:
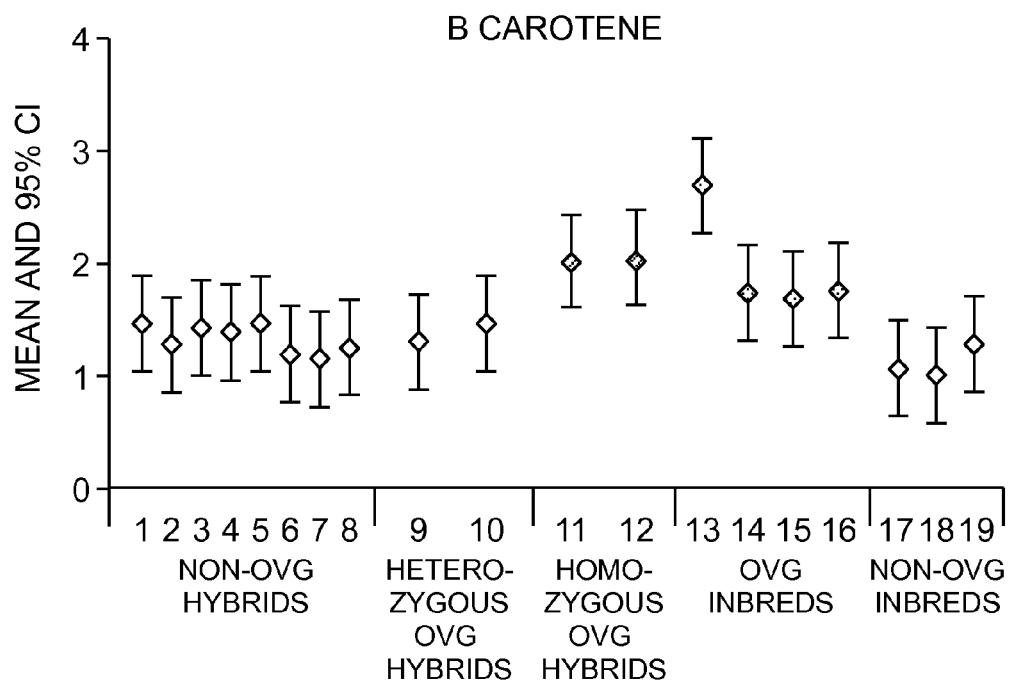

FIG. 23 shows the content in beta-carotene in μg/g of fresh (average value with 95% CI) weight for the different entries shown in FIG. 9, which were grown under standard passive greenhouse conditions in El Ejido, Spain.

Figure 24:
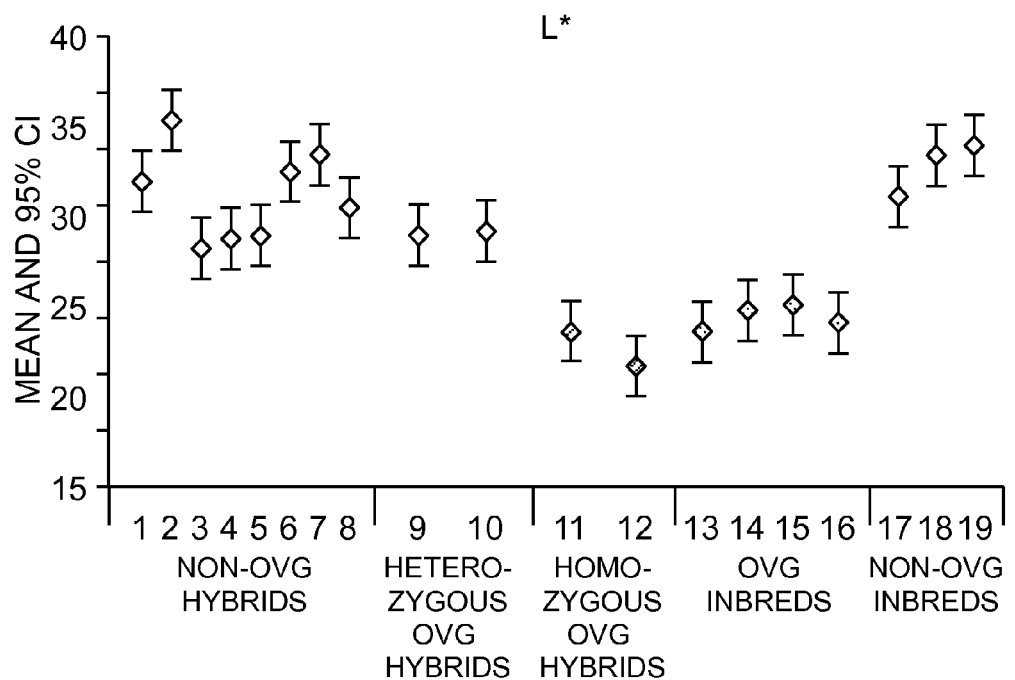

FIG. 24 shows the L* value measured by image analysis using computer vision for the different entries shown in FIG. 9, which were grown under standard passive greenhouse conditions in El Ejido, Spain.

Figure 25:
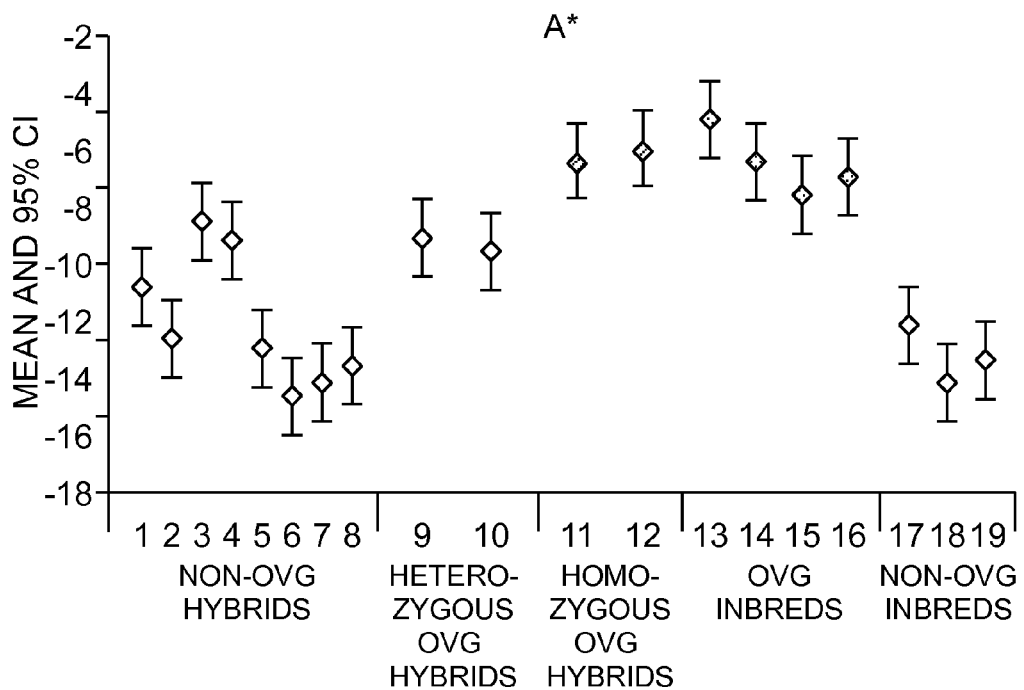

FIG. 25 shows the a* value for the different entries shown in FIG. 9, which were grown under standard passive greenhouse conditions in El Ejido, Spain.

Figure 26:
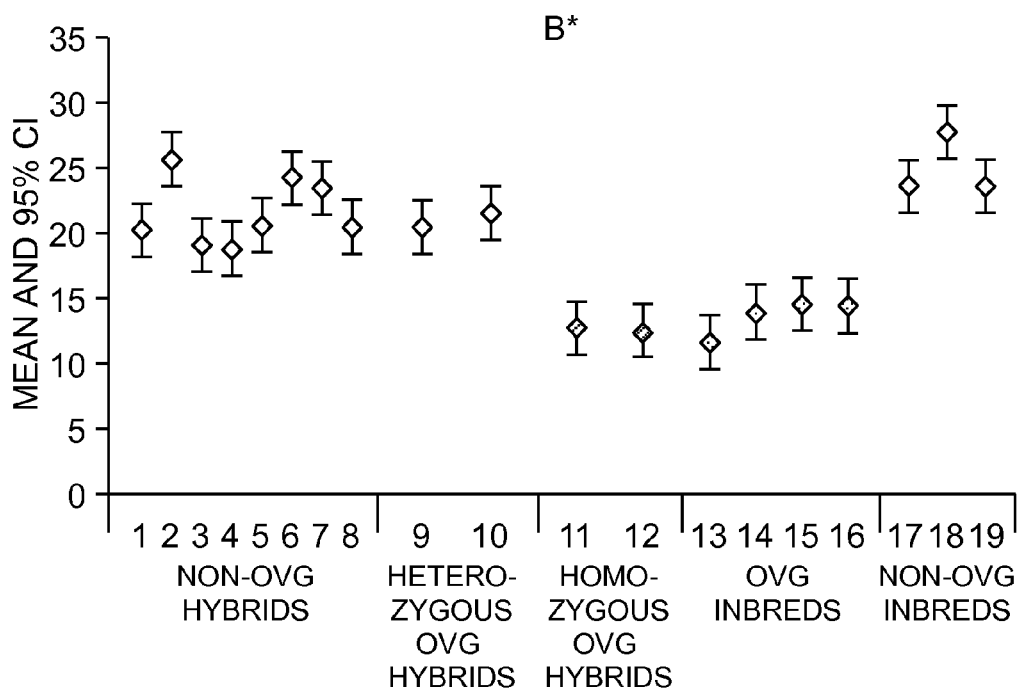

FIG. 26 shows the b* value for the different entries shown in FIG. 9, which were grown under standard passive greenhouse conditions in El Ejido, Spain.

Figure 27:
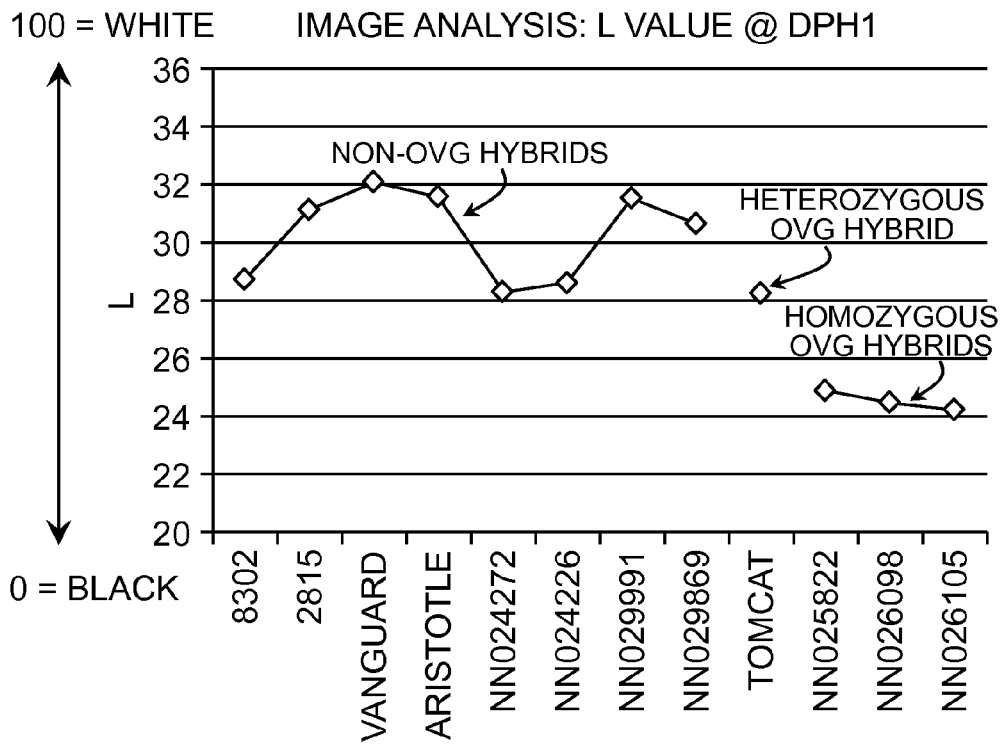

FIG. 27 shows the L* value measured by image analysis for the indicated entries at post-harvest day 1.

Figure 28:
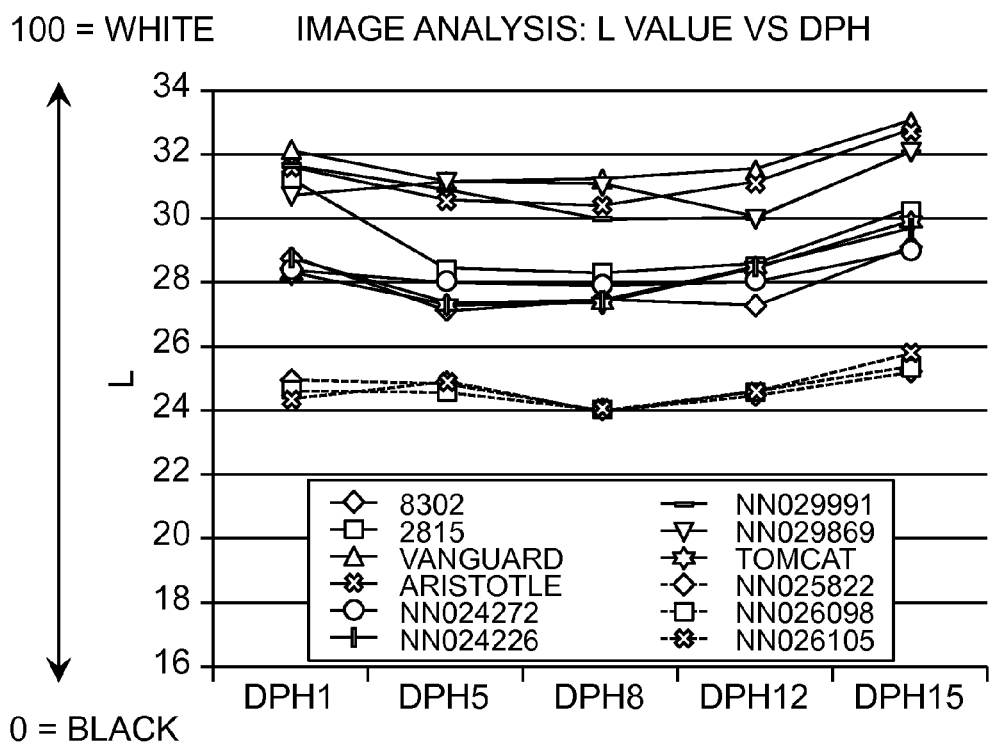

FIG. 28 shows the L* value measured by image analysis for the indicated entries at post-harvest days 1, 5, 8, 12 and 15 (DPH1, DPH5, DPH8, DPH12, and DPH15).

Figure 29:
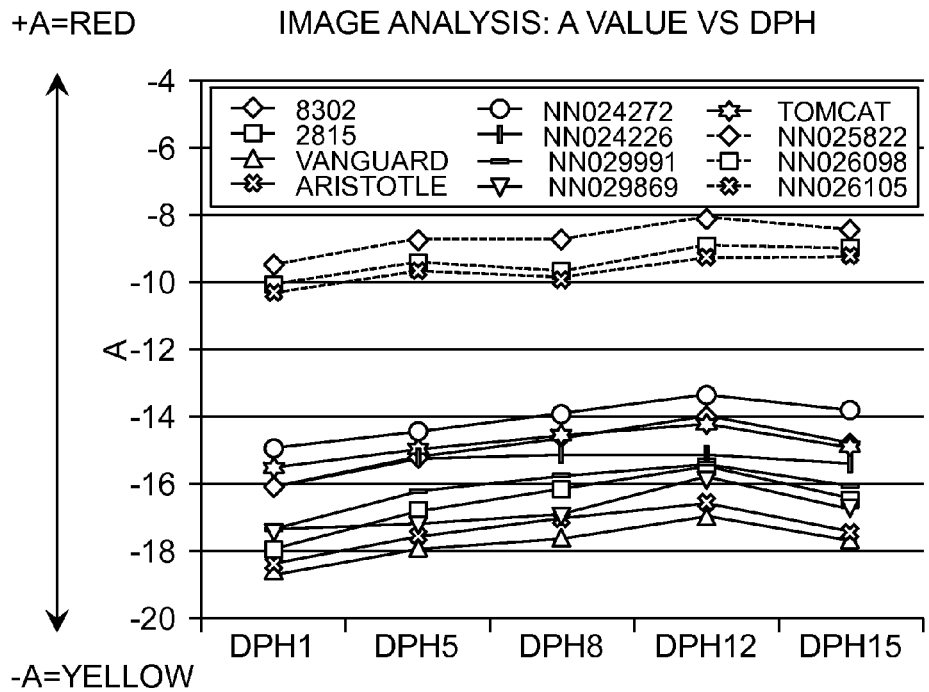

FIG. 29 shows the a* value for the indicated entries at post-harvest days 1, 5, 8, 12 and 15 (DPH1, DPH5, DPH8, DPH12, and DPH15).

Figure 30:
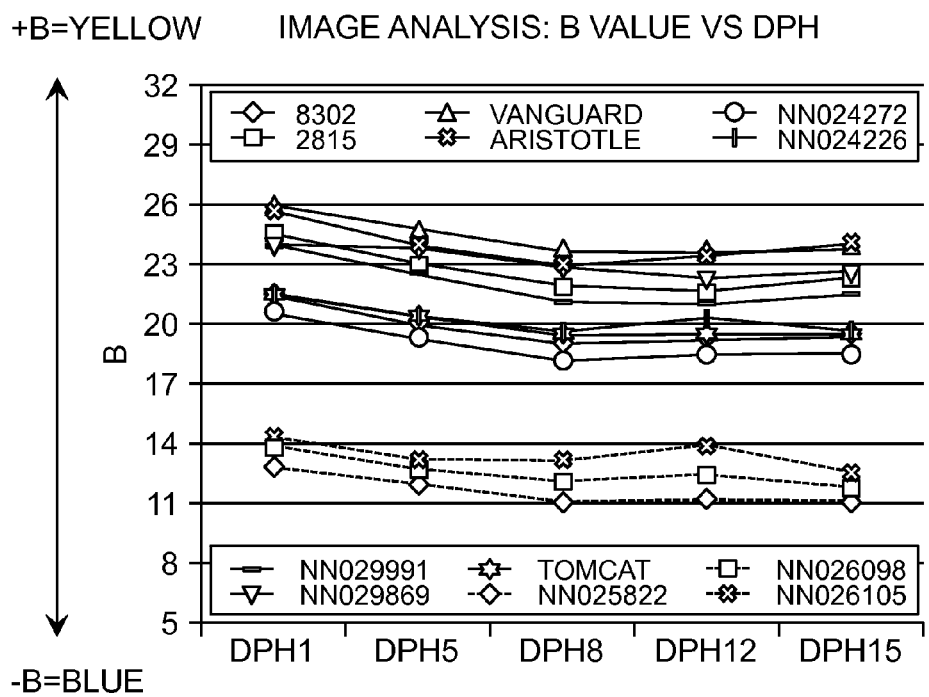

FIG. 30 shows the b* value for the indicated entries at post-harvest days 1, 5, 8, 12 and 15 (DPH1, DPH5, DPH8, DPH12, and DPH15).

DETAILED DESCRIPTION OF THE INVENTION

The present invention is based, in part, on the development of novel pepper varieties producing fruit having an extreme dark green color. The present invention also provides novel pepper cultivars designated RPP 25822, RPP 26098, RPP 26105, 8728C, 16452A, 16452B and 16452C.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

All publications, patent applications, patents, and other references mentioned herein are incorporated by reference in their entirety.

DEFINITIONS

The technical terms and expressions used within the scope of this application are generally to be given the meaning commonly applied to them in the pertinent art of (molecular) plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of 20%, 10%, 5%, 1%, 0.5%, or even 0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" when used in a claim or the description of this invention is not intended to be interpreted to be equivalent to "comprising."

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

"Backcrossing". Backcrossing is a process in which a breeder repeatedly crosses hybrid progeny back to one of the parents, for example, a first generation hybrid F1 with one of the parental genotype of the F1 hybrid.

As used herein, the term "breeding", and grammatical variants thereof, refer to any process that generates a progeny individual. Breeding can be sexual or asexual, or any combination thereof. Exemplary non-limiting types of breeding processes include crossings, selfing, doubled haploid derivative generation, and combinations thereof.

In the context of the present invention, the expression "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

"Cotyledon". One of the first leaves of the embryo of a seed plant; typically one or more in monocotyledons, two in dicotyledons, and two or more in gymnosperms.

A "cultivated pepper" plant is understood within the scope of the invention to refer to a plant that is no longer in the natural state but has been developed by human care and for human use and/or (commercial) growing purposes and/or consumption. "Cultivated pepper plants" are further understood to exclude those wild-type species which comprise the trait being subject of this invention as a natural trait and/or part of their natural genetics. Cultivated pepper plants also typically display favourable agronomical and fruit quality characteristics as well as resistance(s) to *Xanthomonas campestris* pv. *Vesicatoria*, and/or potyvirus, and/or CMV, and/or TMV, and/or TSWV virus, whereas non-cultivated plants do not.

"Determinate Plant". A determinate plant will grow to a fixed number of nodes while an indeterminate plant will continue to grow during the season.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Doubled haploid line". A stable inbred line achieved by doubling the chromosomes of a haploid line, e.g., from anther culture. For example, some pollen grains (haploid) cultivated under specific conditions develop plantlets containing 1n chromosomes. The chromosomes in these plantlets are then induced to "double" (e.g., using chemical means) resulting in cells containing 2n chromosomes. The progeny of these plantlets are termed "doubled haploid" and are essentially non-segregating (e.g., are stable). The term "doubled haploid" is used interchangeably herein with "dihaploid."

"Essentially all the physiological and morphological characteristics". A plant having "essentially all the physiological and morphological characteristics" means a plant having the physiological and morphological characteristics of the recurrent parent, except for the characteristics derived from the converted or transferred gene(s).

In the context of the present invention, the expression "established breeding population" or "population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the expression "extreme dark green" or "extreme dark green color" or "extreme dark green color trait" (and similar expressions including grammatical variants) characterizing the pepper fruits produced by the pepper plant of any of the embodiments and optionally associated with any of the following terms "trait", "locus", "allele" or "QTL" and the like means that the said fruits are characterized by a dark green color and/or an enhanced nutrient content as described herein. In some instances, the extreme dark green trait/locus is referred to as the "overgreen" (OVG) trait/locus.

In representative embodiments, said fruits having an extreme dark green color are characterized by any one or more (in any combination of 2 or all 3) of the following non-limiting characteristics at immature (e.g., green) harvestable stage:

a. green outer surface having an L* value (indicating darkness) that is at least about 2, at least about 3, at least about 4, at least about 5, or more units lower than an L* value for a fruit from a suitable control variety, b. the flesh of the green pepper fruit is characterized by having an L* value (indicating darkness) that is at least about 2, at least about 3, at least about 4, at least about 5, or more units lower than an L* value of the flesh from a fruit from a suitable control variety, and/or c. the calyx of the green pepper fruit is characterized by having an L* value (indicating darkness) that is least about 2, at least about 3, at least about 4, at least about 5 or more units lower than an L* value of a calyx from a fruit from a suitable control variety.

L* values can be determined by any method known in the art (see, e.g., Examples), for (for example, as determined by colorimetry, by image analysis using computer vision, etc.).

In representative embodiments, the fruits having an extreme dark green color are characterized by any one or more (in any combination of 2 or all 3) of the following non-limiting characteristics at immature (e.g., green) harvestable stage:

a. green outer surface having an L* value that is less than about 28, less than about 27, less than about 26, less than about 25, or less than about 24, e.g., as determined by image analysis using computer vision, b. the flesh of the green pepper fruit is characterized by having an L* value (indicating darkness) that is less than about 28, less than about 27, less than about 26, less than about 25, or less than about 24, e.g., as determined by image analysis using computer vision, and/or c. the calyx of the green pepper fruit is characterized by having an L* value (indicating darkness) that is less than about 28, less than about 27, less than about 26, less than about 25, or less than about 24, e.g., as determined by image analysis using computer vision.

In embodiments, using the Munsell Color-Order system and notation, the outer surface, flesh and/or calyx of the fruits having an extreme dark green color are characterized by having a lower Munsell Value (where 0 indicates pure back and 10 indicates pure white) as compared with a fruit from a suitable control variety, e.g., the outer surface, flesh and/or calyx has a Value of about 3 or less, 2.5 or less, or 2 or less.

Furthermore, in embodiments, using the Munsell Color-Order system and notation, the outer surface, flesh and/or calyx of the fruits having an extreme dark green color are characterized by having a higher Munsell Hue as compared with a fruit from a suitable control variety, e.g., the outer surface, flesh and/or calyx of the fruits having extreme dark green color have a Hue of about 5GY (Green-Yellow) or greater, 7.5GY or greater, or about 10GY or greater.

In representative embodiments, said fruits having an extreme dark green color are characterized by any one or more (in any combination of 2, 3 or all 4) of the following non-limiting characteristics at immature (e.g., green) harvestable stage:

a. an increase in the content of violaxanthin of at least about 25%, at least about 50%, at least about 75%, at least about 100% (doubled), or more as compared with a suitable control plant,
b. an increase in the content of lutein of at least about 25%, at least about 50%, at least about 75%, at least about 100% (doubled), or more as compared with a suitable control plant,
c. an increase in the content of chlorophyll a of at least about 25%, at least about 50%, at least about 75%, or at least about 100% (doubled), or more as compared with a suitable control plant, and/or
d. an increase in the content of chlorophyll b of at least about 25%, at least about 50%, at least about 75%, at least about 100% (doubled), or more as compared with a suitable control plant.

In representative embodiments, said fruits having an extreme dark green color are characterized by any one or more (in any combination of 2, 3 or all 4) of the following non-limiting characteristics at immature (e.g., green) harvestable stage:
a. a content of chlorophyll a greater than about 24, particularly greater than about 25, more particularly greater than about 27, more particularly greater than about 30 µg/g of fresh weight,
b. a content of chlorophyll b greater than about 7, particularly greater than about 8 more particularly greater than about 9, more particularly greater than about 10 µg/g of fresh weight,
c. a content of lutein greater than about 5, particularly greater than about 6, particularly greater than about 7 µg/g of fresh weight, and/or
d. a content of violaxanthin greater than about 2.2, particularly greater than about 2.5, more particularly greater than about 3, more particularly greater than about 3.5 µg/g of fresh weight.

In embodiments of the invention, the outer surface of the pepper fruit, the flesh of the fruit and/or or the calyx of the pepper fruit has a substantially uniform extreme dark green color, e.g., at least about 25%, 35%, 50%, 60%, 70%, 75%, 80%, 85%, 90%, 95% or more of the outer surface of the fruit, the flesh of the fruit and/or or the calyx has an extreme dark green color (e.g., as indicated by $L^*$ values).

In representative embodiments, the extreme dark green pepper fruits of the invention are characterized by a slower maturing time, e.g., they retain a substantially uniform green surface and/or flesh color for a longer period of time (e.g., at least about 1, 2, 3, 4, 5, 6, 7, 8, 9, 10, 11, 12, 13, or 14 days longer or more) as compared with a fruit from a suitable control plant with the pepper fruits of the invention. For example, in embodiments, the extreme dark green pepper fruits of the invention show no or essentially no change of the immature extreme dark green color to the mature color (e.g., red), for example, no visible color change or less than about 20%, less than about a 15%, less than about a 10% or less than about a 5% loss of the extreme dark green color of the fruit surface and/or fruit flesh as a result of fruit ripening. In embodiments, the ripening of the extreme dark green pepper fruits of the invention to the mature color (e.g., red) is delayed by at least about 1, 2, 3, 4, 5, 6, 7, 8, 9, 10, 11, 12, 13, or 14 days longer or more as compared with a fruit from a suitable control plant.

Thus, in embodiments, the pepper fruits of the invention advantageously have a longer holding time as compared with a fruit from a suitable control pepper plant, e.g., in the field, for sale as fresh produce and/or for processing.

In embodiments, at least about 25%, 35%, 50%, 60%, 70%, 75%, 80%, 85%, 90% or 95% or more of the fruits produced by the pepper plant, on average, have an extreme dark green color. In embodiments, all or essentially all of the fruits produced by the pepper plant have an extreme dark green color.

The extreme dark green pepper fruits of the invention can comprise any combination of the foregoing characteristics or any other characteristics described herein.

Those skilled in the art will appreciate that the values described herein generally represent averages determined from a plurality of pepper fruits, although individual fruits may have characteristics that fall outside of these values. In embodiments, the characteristics of the pepper fruits having extremely dark green color described above are statistically significant as compared with a fruit from a suitable control pepper plant (e.g., p value<0.1, 0.05 or 0.001).

A "control" pepper plant or fruit as used herein does not have the extreme dark green color trait, e.g., does not comprise QTL1 and/or QTL2 as described herein and is generally grown/produced under substantially the same conditions as the extreme dark green pepper plants and fruits of the invention. Exemplary control pepper plants (and fruits therefrom) include without limitation Crusader, Encore, Declaration, Aristotle, Karisma, 8302, 7141 and 1819.

In representative embodiments, a pepper plant having the extreme dark green color trait comprises QTL1 and/or QTL2 or a functional part thereof.

In representative embodiments, QTL1 is genetically or physically linked to marker loci SP436 and/or SP626.

In embodiments, marker locus SP436 can be identified in an amplification reaction (e.g., PCR amplification) of a DNA fragment with the pair of oligonucleotide primers including forward primer of SEQ ID NO: 1 and/or reverse primer of SEQ ID NO: 2, optionally with the probe of SEQ ID NO 9.

In embodiments, marker locus SP626 can be identified in an amplification reaction (e.g., PCR amplification) of a DNA fragment with the pair of oligonucleotide primers including: forward primer of SEQ ID NO: 3 and/or reverse primer of SEQ ID NO: 4, optionally with the probe of SEQ ID NO 10.

In representative embodiments QTL2 is genetically or physically linked to marker loci SP693 and/or SP694.

In embodiments, marker locus SP693 can be identified in an amplification reaction (e.g., PCR amplification) of a DNA fragment with the pair of oligonucleotide primers including: forward primer of SEQ ID NO: 5 and/or reverse primer of SEQ ID NO: 6, optionally with the probe of SEQ ID NO 11.

In embodiments, marker locus SP694 can be identified in an amplification reaction (e.g., PCR amplification) of a DNA fragment with the pair of oligonucleotide primers including: forward primer of SEQ ID NO: 7 and/or reverse primer of SEQ ID NO: 8, optionally with the probe of SEQ ID NO 12.

In embodiments, the QTL1 and/or QTL2 is not in the native (e.g. natural) genetic background of the pepper plant having the extreme dark green color trait.

In representative embodiments, the extreme dark green color trait is derived from *Capsicum annuum* inbred line 8728C, inbred line 16452A, inbred line 16452B, inbred line 16452C, hybrid RPP 25822, hybrid RPP 26098 and/or hybrid RPP 26105, or in a progeny or in an ancestor thereof.

In embodiments, the pepper plants of the invention are homozygous for the extreme dark green color trait.

"F1 hybrid". A first generation progeny from the cross of two non-isogenic parent plants.

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Genetic complement". As used herein, a "genetic complement" refers to the total genetic make-up of the plant.

A "genetic determinant directing or controlling expression" is understood herein to refer to a heritable genetic element that is capable of contributing to the darkness of the fruit color of the plant by influencing expression of this color trait on the level of the DNA itself, on the level of translation, transcription and/or activation of a final polypeptide product.

"Genetic linkage" or "linkage" or "association" is understood within the scope of the invention to refer to an association of characters in inheritance due to location of genes in proximity on the same chromosome, measured by percent recombination between loci (centi-Morgan, cM).

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes. A genetic marker can be physically located in a position on a chromosome that is within or outside of to the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene).

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

"Heat unit". The amount of heat needed to mature a crop. It is used to measure maturity based on the daily accumulated heat produced during the growing season. The formula [(daily maximum F 0–daily minimum F0)–40]/2 is used to calculate heat units for peppers.

"Heterozygous" is understood within the scope of the invention to refer to unlike alleles at one or more corresponding loci on homologous chromosomes.

"Homozygous" is understood within the scope of the invention to refer to like alleles at one or more corresponding loci on homologous chromosomes.

As used herein, the terms "hybrid", "hybrid plant," and "hybrid progeny" refers to an individual produced from genetically different parents (e.g., a genetically heterozygous or mostly heterozygous individual).

The term "hybridize" as used herein with respect to nucleic acids refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardt's solution; see Green and Sambrook, Molecular Cloning: A Laboratory Manual, Cold Spring Harbor Press, 2012). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

One indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

The expression "immature harvestable stage" is understood herein to refer to a stage in the pepper fruit development where the fruit, having reached essentially full physiological development (e.g., cell division and expansion being essentially complete, fruit size and pericarp thickness having reached essentially maximum values), has not yet gone through the ripening process, e.g., are still an immature green color.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

"Internode". The stem segment between nodes.

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

"Locus" is understood within the scope of the invention to refer to a region on a chromosome, which comprises a gene or any other genetic element or factor contributing to a trait.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

"Node". A node is the thickened enlargement on a plant. It is where the stipules, leaf and peduncle arise.

"Nodes to 1st flower". The number of nodes to 1st flower is obtained by counting the number of nodes from above the point of cotyledon attachment to the node from which the first peduncle arises.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Pepper". As used herein, the term "pepper" or "pepper plant" includes any plant classified as a *Capsicum annuum*, including *C. annuum*, *C. baccatum*, *C. chinense*, *C. frutescens* and *C. pubescens*. Pepper plants include varieties, cultivars and populations *Capsicum*. In embodiments, the pepper is a *C. annuum*. Further, the pepper plants of the invention can produce pungent (hot) or sweet (mild) fruits. In embodiments, the pepper plant is a sweet pepper plant (e.g., a sweet blocky pepper plant), which typically produce immature green fruits that turn red, yellow, red, purple or brown at maturity. In embodiments, the pepper plant is not an ancho pepper plant. The fruits can have any shape including, e.g., blocky or conical. In embodiments, the fruits are blocky. Generally, plants according to the present invention are domesticated (e.g., cultivated) and produce commercially acceptable fruits (e.g., with respect to size, shape, color, yield, and the like).

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, fruits, and the like.

"Plant adaptability". A plant having a good plant adaptability means a plant that will perform well in different growing conditions and seasons.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant Height". Plant height is taken from the top of soil to top most leaf of the plant.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, or any other part or product of the plant.

A "plant organ" is a distinct and visibly structured and differentiated part of a plant such as a root, stem, leaf, flower bud, or embryo.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

"Polymorphism" is understood within the scope of the invention to refer to the presence in a population of two or more different forms of a gene, genetic marker, or inherited trait or a gene product obtainable, for example, through alternative splicing, DNA methylation, etc.

As used herein, the term "population" means a genetically heterogeneous collection of plants sharing a common genetic derivation.

"Probe" as used herein refers to a group of atoms or molecules which is capable of recognising and binding to a specific target molecule or cellular structure and thus allowing detection of the target molecule or structure. Particularly, "probe" refers to a DNA or RNA sequence which is labelled and which can be used to detect the presence of and to quantitate a complementary sequence by molecular hybridization.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, and several known disease resistances such as, for example, Bacterial spot resistance or Tomato Mosaic Virus resistance.

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (i.e., exhibits a normal distribution between two extremes).

"Quantitative Trait Loci". Quantitative Trait Loci (QTL) refers to genetic loci that control to some degree, numerically representable traits that are usually continuously distributed. As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A pepper plant may be considered "resistant" or "tolerant" if resistance/tolerance is observed over a plurality of plants (e.g., an average), even if particular individual plants may be susceptible to the biotic or abiotic factor or stressor.

The "ripening process" is associated with chloroplasts changing to chromoplasts, with chlorophyll degradation, carotenoid biosynthesis, seed maturation, and changes in the carbohydrate content of the pericarp.

"Selective breeding" is understood within the scope of the invention to refer to a program of breeding that uses plants that possess or display desirable traits as parents.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

"Single gene converted". A single gene converted or conversion plant refers to a plant that is developed by plant breeding techniques (e.g., backcrossing) or via genetic engineering wherein essentially all of the desired morphological and physiological characteristics of a line are recovered in addition to the single gene transferred into the line via the plant breeding technique or via genetic engineering.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (i.e. amplified sequence or target), one or more labeled allele-specific oligonucleotide probes and a detection system that records and interprets the hybridization signal.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences. The thermal melting point is the temperature (under defined ionic strength and pH) at which 50% of the target sequence hybridizes to a perfectly matched probe. Very stringent conditions are selected to be equal to the melting temperature (Tm) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

As used herein, the term "variety" or "cultivar" means a group of similar plants that by structural features and performance can be identified from other varieties within the same species.

EMBODIMENTS

In representative embodiments, the invention relates to a pepper plant, particularly a cultivated pepper plant, more particularly a cultivated blocky fruit type pepper plant, more particularly a cultivated sweet blocky fruit type pepper plant bearing extreme dark green color fruit at immature harvestable stage, said plant comprising one more (e.g., two) genetic determinants directing or controlling expression of said extreme dark green color in the pepper fruit of the pepper plant.

The terms "extreme dark green," "extreme dark green color" and "extreme dark green color trait" are defined and described in more detail herein.

In particular, in specific embodiments, said one or more genetic determinants are represented by one or more QTL (e.g., two QTL) or a functional part thereof capable of directing or controlling expression of said dark green immature fruit color in the pepper fruit of the pepper plant.

In representative embodiments, a pepper plant according to the invention is provided, particularly a cultivated pepper plant, wherein one or more (e.g., two) QTLs or a functional part thereof are genetically or physically linked to marker loci, which co-segregate with the extreme dark green color and comprise one or more of SP436, SP626 SP693 and/or SP694.

In representative embodiments, the one or more QTLs comprise QTL1, which is linked to marker loci SP436 and/or SP626 and/or QTL2, which is linked to marker loci SP693 and/or SP694.

In representative embodiments, a pepper plant, particularly a cultivated pepper plant, according to any of the preceding embodiments is provided, wherein said QTL1 or a functional part thereof is genetically linked to marker loci SP436 and SP626 and wherein:
i. marker locus SP436 can be identified by amplification (e.g., PCR amplification) of a DNA fragment with the pair of oligonucleotide primers: forward primer of SEQ ID NO: 1 and reverse primer of SEQ ID NO: 2, optionally using probe SEQ ID NO 9,
ii. marker locus SP626 can be identified in by amplification (e.g., PCR amplification) of a DNA fragment with the pair of oligonucleotide primers: forward primer of SEQ ID NO: 3 and reverse primer of SEQ ID NO: 4, optionally using probe SEQ ID NO 10.

In representative embodiments, a pepper plant, particularly a cultivated pepper plant, according to any of the preceding embodiments is provided, wherein said QTL2 or a functional part thereof is genetically linked to marker loci SP693 and SP694, and wherein:
i. marker locus SP693 can be identified by amplification (e.g., PCR amplification) of a DNA fragment with the pair of oligonucleotide primers: forward primer of SEQ ID NO: 5 and reverse primer of SEQ ID NO: 6, optionally with probe SEQ ID NO 11,
ii. marker locus SP694 can be identified by amplification (e.g., PCR amplification) of a DNA fragment with the pair of oligonucleotide primers: forward primer of SEQ ID NO: 7 and reverse primer of SEQ ID NO: 8, optionally using probe SEQ ID NO 12.

In representative embodiments, the extreme dark green color trait is derived from *Capsicum annuum* line 8728C, line 16452A, line 16452B, line 16452C, RPP 25822, RPP 26098 and/or RPP 26105, or from a progeny or from an ancestor thereof.

In representative embodiments, the invention relates to a pepper plant, particularly a cultivated pepper plant, according to any of the preceding embodiments, comprising alleles at the one or more QTLs in the pepper genome contributing to extreme dark green color in the pepper fruit of the pepper plant, which are complementary to the corresponding alleles present in *Capsicum annuum* line 8728C, line 16452A, line 16452B, line 16452C, RPP 25822, RPP 26098 or RPP 26105, or in a progeny or in an ancestor thereof, and genetically linked to marker loci in the genome of *Capsicum annuum* line 8728C, line 16452A, line 16452B, line 16452C, RPP 25822, RPP 26098 or RPP 26105, or in a progeny or in an ancestor thereof, which marker loci co-segregate with the Extreme dark green color and can be identified in the genome of *Capsicum annuum* line 8728C, line 16452A, line 16452B, line 16452C, RPP 25822, RPP 26098 or RPP 26105, and comprise one or more of SP436, SP626, SP693 and/or SP694.

In representative embodiments of the invention, a pepper plant, particularly a cultivated pepper plant, according to any of the embodiments herein is provided, wherein QTL1 is obtainable from a donor plant having the genetic background of *Capsicum annuum* line 8728C, line 16452A, line 16452B, line 16452C, RPP 25822, RPP 26098 or RPP 26105, or from a progeny or an ancestor thereof, comprising said QTL1 or an Extreme dark green color-conferring part thereof.

In representative embodiments of the invention, a pepper plant, particularly a cultivated pepper plant, according to any of the preceding embodiments is provided, wherein QTL2 is obtainable from a donor plant having the genetic background of *Capsicum annuum* line 8728C, line 16452A, line 16452B, line 16452C, RPP 25822, RPP 26098 or RPP 26105, or from a progeny or an ancestor thereof, comprising said QTL2 or an Extreme dark green color-conferring part thereof.

In representative embodiments, a pepper plant, particularly a cultivated pepper plant, according to any of the embodiments described herein is provided, wherein said genetic determinant(s) are obtainable from *Capsicum annuum* line 8728C, line 16452A, line 16452B, line 16452C, RPP 25822, RPP 26098 and/or RPP 26105.

In representative embodiments of the invention, the pepper plant is a plant according to any of the embodiments described herein, which plant is a pepper plant of the genus *Capsicum*, particularly a cultivated pepper plant, particularly a haploid, a doubled haploid, an inbred or a hybrid.

In one embodiment, the invention provides a pepper plant according to any of the embodiments described herein, which is a hybrid pepper plant, particularly a cultivated pepper plant, comprising QTL1 and/or QTL2 or an Extreme dark green color-conferring part thereof and producing pepper fruits having the color and/or pigment characteristics associated with the extreme dark green color trait at the immature harvestable stage as described herein, wherein QTL1 and/or QTL2 are genetically linked to marker loci co-segregating with the Extreme dark green color, wherein said QTL1 and/or QTL2 are obtainable from a donor plant having the genetic background of *Capsicum annuum* line 8728C, line 16452A, line 16452B, line 16452C, RPP 25822, RPP 26098 or RPP 26105, or in a progeny or an ancestor thereof, comprising said QTL1 and/or QTL2 or an Extreme dark green color-conferring part thereof and wherein the marker loci comprises one or more of SP436, SP626, SP693 and/or SP694.

In representative embodiments the pepper plant, particularly a cultivated pepper plant, of the invention is a plant according to any of the embodiments described herein, which grows fruits selected from the group consisting of blocky type peppers.

The present invention further relates to seed of a pepper plant, particularly a cultivated pepper plant, according to any of the embodiments herein, which is capable of growing a pepper plant bearing extreme dark green color fruit according to the invention.

In representative embodiments, a kit for the detection of the Extreme dark green color locus in a pepper plant, particularly a cultivated pepper plant, is herein provided, wherein said kit comprises at least one oligonucleotide primer pair, optionally with a probe, selected from:
a. primer pair 1 represented by a forward primer of SEQ ID NO 1 and a reverse primer of SEQ ID NO 2, and optionally the probe of SEQ ID NO 9 or;
b. primer pair 2 represented by a forward primer of SEQ ID NO 3 and a reverse primer of SEQ ID NO 4, and optionally the probe of SEQ ID NO 10, or;
c. primer pair 3 represented by a forward primer of SEQ ID NO 5 and a reverse primer of SEQ ID NO 6, and optionally the probe of SEQ ID NO 11, and/or;
d. primer pair 4 represented by a forward primer SEQ ID NO 7 and reverse primer of SEQ ID NO 8, and optionally the probe of SEQ ID NO 12, and/or another primer or primer pair representing an adjacent markers that is statistically correlated and thus co-segregates with the Extreme dark green color.

In further embodiments, the present invention relates also to the use of some or all of these DNA markers/marker sequences according to the invention for diagnostic selection and/or genotyping of a pepper plant of the Extreme dark green color locus or loci in a pepper plant, particularly a cultivated pepper plant, particularly of the Extreme dark green color locus or loci, particularly in a pepper plant according to the invention.

In other embodiments, the present invention further contemplates the use of some or all of these DNA markers for identifying in a pepper plant, particularly a cultivated pepper plant, particularly a pepper plant according to the invention, the presence of the Extreme dark green color locus or loci and/or for monitoring the introgressing of the Extreme dark green color locus or loci in a pepper plant, particularly a cultivated pepper plant, particularly a pepper plant according to the invention and as described herein.

In representative embodiments, the invention relates to the polynucleotide (amplification product) obtainable in an amplification reaction (e.g., PCR amplification) involving at least one oligonucleotide primer selected from the group consisting of SEQ ID NO 1; SEQ ID NO 2; SEQ ID NO 3; SEQ ID NO 4; SEQ ID NO 5; SEQ ID NO 6, SEQ ID NO 7; SEQ ID NO 8 or a pair of oligonucleotide primers (e.g., PCR oligonucleotide primers), and reacting with probes optionally selected from the group comprising SEQ ID NO 9, SEQ ID NO 10, SEQ ID NO 11 and SEQ ID NO 12, selected from
a. primer pair 1 represented by a forward primer of SEQ ID NO 1 and a reverse primer of SEQ ID NO 2, and optionally the probe of SEQ ID NO 9 or;
b. primer pair 2 represented by a forward primer of SEQ ID NO 3 and a reverse primer of SEQ ID NO 4, and optionally the probe of SEQ ID NO 10 or;
c. primer pair 3 represented by a forward primer of SEQ ID NO 5 and a reverse primer of SEQ ID NO 6, and optionally the probe of SEQ ID NO 11 and/or;
d. primer pair 4 represented by a forward primer of SEQ ID NO 7 and a reverse primer of SEQ ID NO 8, and optionally the probe of SEQ ID NO 12 and/or by another primer representing an adjacent marker that is statistically correlated and thus co-segregates with the Extreme dark green color or with one of the markers disclosed, which amplification product corresponds to an amplification product obtainable from *Capsicum annuum* line 8728C, line 16452A, line 16452B, line 16452C, RPP 25822, RPP 26098 or RPP 26105 in an amplification reaction (e.g., PCR amplification) with identical primers or primer pairs provided that the respective marker locus or loci is still present in said pepper plant and/or can be considered an allele thereof.

Also contemplated herein is a polynucleotide that has at least about 80%, particularly at least about 85%, particularly at least about 90%, particularly at least about 95%, particularly at least about 96%, particularly at least about 97%, particularly at least about 98%, particularly at least about 99% sequence identity with the sequence of said amplification product and/or a polynucleotide exhibiting a nucleotide sequence that hybridizes to the nucleotide sequences of said amplification product obtainable in the above amplification reaction (e.g., PCR amplification reaction).

The amplification product according to the invention and described herein above can then be used for generating or developing new primers and/or probes that can be used for identifying the Extreme dark green color locus.

The present invention therefore further relates in one embodiment to derived markers, particularly to derived primers or probes, developed from an amplification product according to the invention and as described herein above by methods known in the art, which derived markers are genetically linked to the Extreme dark green color locus, particularly the Extreme dark green color locus.

The identification of a pepper plant with extreme dark green color may be done by measuring and selecting plants bearing fruits with the color and/or pigment/nutritional characteristics associated with the extreme dark green color trait at the immature harvestable stage as described herein.

In representative embodiments, the invention relates to a method for producing a pepper plant, particularly a cultivated pepper plant, exhibiting extreme dark green color in the pepper fruit of the pepper plant, comprising the steps of:
a. selecting a pepper plant of the genus *Capsicum annuum*, which exhibits Extreme dark green color, wherein said color related trait is associated with QTL1 and/or QTL 2, or a functional part thereof capable of directing or controlling expression of said extreme dark green color in the pepper fruit of the pepper plant, wherein said QTL1 and/or QTL 2 or a functional part thereof are genetically linked to at least one marker locus, selected from marker loci SP436, SP626, SP693 and/or SP694 or any adjacent marker that is statistically correlated and thus co-segregates with the Extreme dark green color; or with any of the disclosed marker loci,
b. crossing said plant of step a), which exhibits Extreme dark green color, with a pepper plant, particularly a cultivated pepper plant, which is not extreme dark green color, and
c. selecting progeny pepper plant from said cross which exhibits extreme dark green color and demonstrates association with said marker locus or loci of step a) and bears extreme dark green color fruits at the immature harvestable stage as described herein.

In further embodiments, the invention provides a method for obtaining pepper fruits with extreme dark green color, particularly blocky pepper fruits, comprising the steps of
i. sowing a seed of a plant according to any one of the preceding embodiments or obtained in a method according to any of the preceding embodiments; and
ii. growing said plant in order to produce fruit and harvesting the fruits produced by said plant.

The present invention further includes and provides methods of identifying a pepper plant bearing extreme dark green pepper fruits comprising:
a. providing a population segregating for dark green immature fruit color,
b. screening the segregating population for a member having an extreme dark green pepper fruit trait, wherein said trait can be identified by the presence of the following molecular markers in the genome: SP436, SP626, SP693 and/or SP694
c. selecting at least one member of the segregating population, wherein said at least member is bearing an extreme dark green pepper fruit trait.

In still other embodiments, the invention relates to an Extreme dark green color-conferring QTL or an Extreme dark green color-conferring part thereof, which is associated with at least a 1st DNA marker represented by a 1st pair of oligonucleotide primers (e.g., PCR oligonucleotide primers) comprising forward primer of SEQ ID NO 1, reverse primer of SEQ ID NO 2, and optionally the probe of SEQ ID NO 9, and/or at least a 2nd DNA marker represented by a 2nd pair of oligonucleotide primers (e.g., PCR oligonucleotide primers) comprising forward primer of SEQ ID NO 3, reverse primer of SEQ ID NO 4, and optionally the probe of SEQ ID NO 10, particularly said QTL or a functional part thereof is associated with said 1st and 2nd DNA marker.

In still further embodiments, the invention relates to an Extreme dark green color-conferring QTL or an Extreme dark green color-conferring part thereof, which and is associated with at least a 1st DNA marker represented by a 1st pair of oligonucleotide primers (e.g., PCR oligonucleotide primers) comprising forward primer of SEQ ID NO 5, reverse primer of SEQ ID NO 6 and optionally the probe of SEQ ID NO 11, and a 2nd pair of oligonucleotide primers (e.g., PCR oligonucleotide primers) comprising forward primer of SEQ ID NO 7, reverse primer of SEQ ID NO 8 and optionally the probe of SEQ ID NO 12, particularly said QTL or a functional part thereof is associated with said 1st and 2nd DNA marker.

The present invention also relates to the use of extreme dark green color propagating material obtainable from a pepper plant according to any of the preceding embodiments for growing a pepper plant in order to produce extreme dark green color fruit and harvest said extreme dark green color fruits wherein the said fruits are characterized, at immature harvestable stage, by the color and/or pigment characteristics associated with the dark green color trait as described herein.

It is further contemplated by the present invention to provide a method for increasing the pigment content of pepper fruits of pepper plant selected from the group comprising chlorophyll a, chlorophyll b, lutein and/or violaxanthin, comprising the steps of:

a. selecting a plant of the genus *Capsicum*, which exhibits Extreme dark green color, wherein said color related trait is associated with one or more QTLs or a functional part thereof capable of directing or controlling expression of said extreme dark green color in the pepper fruit of the pepper plant, wherein said trait can be identified by the presence of one or more of the following molecular markers loci in the genome: SP436, SP626, SP693 and/or SP694 or by any adjacent marker that is statistically correlated and thus co-segregates with the Extreme dark green color;

b. crossing said plant of step a), which exhibits Extreme dark green color, with a pepper plant, particularly a cultivated pepper plant, which does not exhibit extreme dark green color, and c. selecting progeny from said cross which exhibit the extreme dark green color trait and demonstrates association of the extreme dark green color with said marker loci of step a).

Further embodiments of the present invention provide a method for providing pepper plant producing pepper fruits exhibiting the extreme dark green pepper trait as described herein, comprising the steps of:

a. selecting a plant of the genus *Capsicum*, which exhibits Extreme dark green color, wherein said trait is associated with QTL1 and/or QTL2, or a functional part thereof capable of directing or controlling expression of said extreme dark green color in the pepper fruit of the pepper plant, wherein said QTL1 or a functional part thereof is genetically linked to marker loci SP436 and/or SP626 and wherein QTL2 or a functional part thereof is genetically linked to marker loci SP693 and/or SP694, which co-segregate with the Extreme dark green color and can be identified in an amplification reaction (e.g., PCR amplification reaction) by i. forward primer of SEQ ID NO 1, reverse primer of SEQ ID NO 2 and optionally the probe of SEQ ID NO 9 for marker locus SP436;

ii. forward primer of SEQ ID NO 3, reverse primer of SEQ ID NO 4 and optionally the probe of SEQ ID NO 10, for marker locus SP626;

iii. forward primer of SEQ ID NO 5, reverse primer of SEQ ID NO 6 and optionally the probe of SEQ ID NO 11 for marker locus SP693;

iv. forward primer of SEQ ID NO 7, reverse primer of SEQ ID NO 8 and optionally the probe of SEQ ID NO 12 for marker locus SP694 v. or by any adjacent marker that is statistically correlated and thus co-segregates with the Extreme dark green color.

In representative embodiments, the pepper plant according to the present invention, as described in any of the previous embodiments, is homozygous at QTL1 and/or QTL2.

Based on the description of the present invention, the skilled person who is in possession of *Capsicum annuum* line 8728C, line 16452A, line 16452B, line 16452C, RPP 25822, RPP 26098 or RPP 26105, or a progeny or ancestor thereof containing the genetic determinants capable of directing or controlling the extreme dark green color trait, as described herein, has no difficulty to transfer the said genetic determinant(s) of the present invention to other pepper plants of various types using breeding techniques well-known in the art with the support of the QTL(s) and marker loci herein disclosed.

Botanical Description of Pepper Cultivars RPP 25822, RPP 26098 and RPP 26105.

Pepper cultivars RPP 25822, RPP 26098 and RPP 26105 are suitable for the fresh and processor markets.

OVG hybrids RPP 26098, RPP 25822 and RPP 26105 produce an open, erect bush with medium vigor. The fruit is blocky, extremely dark green in color and glossy. These hybrids are particularly well-adapted to production conditions in the Southeastern United States. Yield and marketable fruit characteristics are within commercially acceptable limits for non-OVG hybrids.

Additional physiological and morphological description of OVG hybrids RPP 26098, RPP 25822 and RPP 26105 as well as male inbred parent 8728C is provided below in Table 1.

TABLE 1

| TRAIT NAME | VALUE |
|---|---|
| Hybrid RPP 26098 | |
| Seedling: anthocyanin coloration of hypocotyl | Present |
| Plant: shortened internodes (in upper part) | Absent (indeterminant) |
| Plant: vigor | Medium |
| Plant: height | Medium |
| Flower: anthocyanin coloration in anther | Present |
| Fruit: color (before maturity) | Green |
| Fruit: intensity of color (before maturity) | Very dark |
| Fruit: length | Medium |
| Fruit: diameter | Medium |
| Fruit: shape in longitudinal section | Square |
| Fruit: color (at maturity) | Red |
| Fruit: intensity of color (at maturity) | Very dark |
| Fruit: number of locules | Equally three and four |
| Fruit: length (cm) | 8 |
| Fruit: diameter (cm) | 8 |
| Fruit: capsaicin in placenta | Absent |
| Time of maturity | Medium |
| Ripening can be compared with variety . . . | Crusader |
| Plant setting ability cold | Normal |
| Plant setting ability hot | Normal |
| Resistances: | |
| Pepper Mottle Virus | Highly resistant |
| *Xanthomonas campestris* pv. *vesicatoria*, race 1 | Highly resistant |
| *Xanthomonas campestris* pv. *vesicatoria*, race 2 | Highly resistant |
| *Xanthomonas campestris* pv. *vesicatoria*, race 3 | Highly resistant |
| *Xanthomonas campestris* pv. *vesicatoria*, race 4 | Highly resistant |
| *Xanthomonas campestris* pv. *vesicatoria*, race 5 | Highly resistant |
| *Xanthomonas campestris* pv. *vesicatoria*, race 6 | Susceptible |
| *Xanthomonas campestris* pv. *vesicatoria*, race 7 | Highly resistant |
| *Xanthomonas campestris* pv. *vesicatoria*, race 8 | Highly resistant |
| *Xanthomonas campestris* pv. *vesicatoria*, race 9 | Highly resistant |

TABLE 1-continued

| TRAIT NAME | VALUE |
|---|---|
| Hybrid RPP 25822 | |
| Seedling: anthocyanin coloration of hypocotyl | Present |
| Plant: shortened internodes (in upper part) | Absent (indeterminant) |
| Plant: vigor | Medium |
| Plant: height | Medium |
| Flower: anthocyanin coloration in anther | Present |
| Fruit: color (before maturity) | Green |
| Fruit: intensity of color (before maturity) | Very dark |
| Fruit: length | Medium |
| Fruit: diameter | Medium |
| Fruit: shape in longitudinal section | Square |
| Fruit: color (at maturity) | Red |
| Fruit: intensity of color (at maturity) | Very dark |
| Fruit: number of locules | Equally three and four |
| Fruit: length (cm) | 8 |
| Fruit: diameter (cm) | 8 |
| Fruit: capsaicin in placenta | Absent |
| Time of maturity | Medium |
| Ripening can be compared with variety . . . | Crusader |
| Plant setting ability cold | Normal |
| Plant setting ability hot | Normal |
| Resistances: | |
| Pepper Mottle Virus | Highly resistant |
| Xanthomonas campestris pv. vesicatoria, race 1 | Highly resistant |
| Xanthomonas campestris pv. vesicatoria, race 2 | Highly resistant |
| Xanthomonas campestris pv. vesicatoria, race 3 | Highly resistant |
| Xanthomonas campestris pv. vesicatoria, race 4 | Highly resistant |
| Xanthomonas campestris pv. vesicatoria, race 5 | Highly resistant |
| Xanthomonas campestris pv. vesicatoria, race 6 | Susceptible |
| Xanthomonas campestris pv. vesicatoria, race 7 | Highly resistant |
| Xanthomonas campestris pv. vesicatoria, race 8 | Highly resistant |
| Xanthomonas campestris pv. vesicatoria, race 9 | Highly resistant |
| Hybrid RPP 26105 | |
| Seedling: anthocyanin coloration of hypocotyl | Present |
| Plant: shortened internodes (in upper part) | Absent (indeterminant) |
| Plant: vigor | Medium |
| Plant: height | Medium |
| Flower: anthocyanin coloration in anther | Present |
| Fruit: color (before maturity) | Green |
| Fruit: intensity of color (before maturity) | Very dark |
| Fruit: length | Medium |
| Fruit: diameter | Medium |
| Fruit: shape in longitudinal section | Square |
| Fruit: color (at maturity) | Red |
| Fruit: intensity of color (at maturity) | Very dark |
| Fruit: number of locules | Equally three and four |
| Fruit: length (cm) | 8 |
| Fruit: diameter (cm) | 8 |
| Fruit: capsaicin in placenta | Absent |
| Time of maturity | Medium |
| Ripening can be compared with variety . . . | Crusader |
| Plant setting ability cold | Normal |
| Plant setting ability hot | Normal |
| Resistances: | |
| Pepper Mottle Virus | Highly resistant |
| Xanthomonas campestris pv. vesicatoria, race 1 | Highly resistant |
| Xanthomonas campestris pv. vesicatoria, race 2 | Highly resistant |
| Xanthomonas campestris pv. vesicatoria, race 3 | Highly resistant |
| Xanthomonas campestris pv. vesicatoria, race 4 | Highly resistant |
| Xanthomonas campestris pv. vesicatoria, race 5 | Highly resistant |
| Xanthomonas campestris pv. vesicatoria, race 6 | Susceptible |
| Xanthomonas campestris pv. vesicatoria, race 7 | Highly resistant |
| Xanthomonas campestris pv. vesicatoria, race 8 | Highly resistant |
| Xanthomonas campestris pv. vesicatoria, race 9 | Highly resistant |
| Inbred line 8728C | |
| Seedling: anthocyanin coloration of hypocotyl | Present |
| Plant: length of internodes | Medium-Long |
| Plant: intensity of anthocyanin | Medium |
| Plant: vigor | Strong |
| Plant: hairiness of the plant | Very weak |
| Plant: height | Medium-high |
| Fruit: color before maturity | Green |
| Fruit: attitude of the fruits | Drooping |
| Fruit: shape in longitudinal section | Square |
| Fruit: color at maturity | Red |
| Fruit: speed of fruit color change to mature | Slow |
| Fruit: type | Sweet-blocky |
| Predominant number of locules | Three and four |
| Thickness of pericarp of the fruit | Medium-thick |
| Capsaicin in placenta | Absent |
| Fruit: pungency level | No pungency |
| Fruit: sensitivity for cracking | Medium |
| Fruit: Size at harvest | Medium |
| Sensitivity for BER | Isolated BER |
| Sensitivity for blind and fork | Not sensitive |
| Tendency for parthenocarpy | Yes |
| Flower expression of male sterility | No |
| Balance of the plant | Vegetative |
| Seeds pre-germinate in fruits | No |
| Resistances: | |
| Pepper Mottle Virus | Susceptible |
| Phytophthora capsici | Susceptible |
| Tobacco Etch Virus | Highly resistant |
| Tobacco Mosaic Virus | Susceptible |
| Xanthomonas campestris pv. vesicatoria, race 1 | Susceptible |
| Xanthomonas campestris pv. vesicatoria, race 2 | Susceptible |
| Xanthomonas campestris pv. vesicatoria, race 3 | Susceptible |
| Xanthomonas campestris pv. vesicatoria, race 4 | Highly resistant |
| Xanthomonas campestris pv. vesicatoria, race 5 | Highly resistant |
| Xanthomonas campestris pv. vesicatoria, race 6 | Susceptible |
| Inbred Line 16452A | |
| Seedling: anthocyanin coloration of hypocotyl | Present |
| Plant: shortened internodes (in upper part) | Absent (indeterminant) |
| Plant: vigor | Medium |
| Plant: height | Medium |
| Flower: anthocyanin coloration in anther | Present |
| Fruit: color (before maturity) | Green |
| Fruit: intensity of color (before maturity) | Very dark |
| Fruit: length | Medium |
| Fruit: diameter | Medium |
| Fruit: shape in longitudinal section | Square |
| Fruit: color (at maturity) | Red |
| Fruit: intensity of color (at maturity) | Very dark |
| Fruit: number of locules | Equally three and four |
| Fruit: length (cm) | 3.5" |
| Fruit: diameter (cm) | 3.5" |
| Fruit: capsaicin in placenta | Absent |
| Time of maturity | Medium |
| Ripening can be compared with variety . . . | Crusader |
| Plant setting ability cold | Normal |
| Plant setting ability hot | Normal |
| Resistances: | |
| Pepper Mottle Virus | Highly resistant |
| Xanthomonas campestris pv. vesicatoria, race 1 | Highly resistant |
| Xanthomonas campestris pv. vesicatoria, race 2 | Highly resistant |
| Xanthomonas campestris pv. vesicatoria, race 3 | Highly resistant |
| Xanthomonas campestris pv. vesicatoria, race 4 | Highly resistant |
| Xanthomonas campestris pv. vesicatoria, race 5 | Highly resistant |
| Xanthomonas campestris pv. vesicatoria, race 6 | Susceptible |
| Xanthomonas campestris pv. vesicatoria, race 7 | Highly resistant |
| Xanthomonas campestris pv. vesicatoria, race 8 | Highly resistant |
| Xanthomonas campestris pv. vesicatoria, race 9 | Highly resistant |
| Inbred Line 16452B | |
| Seedling: anthocyanin coloration of hypocotyl | Present |
| Plant: shortened internodes (in upper part) | Absent (indeterminant) |
| Plant: vigor | Medium |
| Plant: height | Medium |
| Flower: anthocyanin coloration in anther | Present |
| Fruit: color (before maturity) | Green |
| Fruit: intensity of color (before maturity) | Very dark |
| Fruit: length | Medium |
| Fruit: diameter | Medium |
| Fruit: shape in longitudinal section | Square |
| Fruit: color (at maturity) | Red |
| Fruit: intensity of color (at maturity) | Very dark |

TABLE 1-continued

| TRAIT NAME | VALUE |
|---|---|
| Fruit: number of locules | Equally three and four |
| Fruit: length (cm) | 3.5" |
| Fruit: diameter (cm) | 3.5" |
| Fruit: capsaicin in placenta | Absent |
| Time of maturity | Medium |
| Ripening can be compared with variety . . . | Crusader |
| Plant setting ability cold | Normal |
| Plant setting ability hot | Normal |
| Resistances: | |
| Pepper Mottle Virus | Highly resistant |
| Xanthomonas campestris pv. vesicatoria, race 1 | Highly resistant |
| Xanthomonas campestris pv. vesicatoria, race 2 | Highly resistant |
| Xanthomonas campestris pv. vesicatoria, race 3 | Highly resistant |
| Xanthomonas campestris pv. vesicatoria, race 4 | Highly resistant |
| Xanthomonas campestris pv. vesicatoria, race 5 | Highly resistant |
| Xanthomonas campestris pv. vesicatoria, race 6 | Susceptible |
| Xanthomonas campestris pv. vesicatoria, race 7 | Highly resistant |
| Xanthomonas campestris pv. vesicatoria, race 8 | Highly resistant |
| Xanthomonas campestris pv. vesicatoria, race 9 | Highly resistant |
| Inbred Line 16452C | |
| Seedling: anthocyanin coloration of hypocotyl | Present |
| Plant: shortened internodes (in upper part) | Absent (indeterminant) |
| Plant: vigor | Medium |
| Plant: height | Medium |
| Flower: anthocyanin coloration in anther | Present |
| Fruit: color (before maturity) | Green |
| Fruit: intensity of color (before maturity) | Very dark |
| Fruit: length | Medium |
| Fruit: diameter | Medium |
| Fruit: shape in longitudinal section | Square |
| Fruit: color (at maturity) | Red |
| Fruit: intensity of color (at maturity) | Very dark |
| Fruit: number of locules | Equally three and four |
| Fruit: length (cm) | 3.5" |
| Fruit: diameter (cm) | 3.5" |
| Fruit: capsaicin in placenta | Absent |
| Time of maturity | Medium |
| Ripening can be compared with variety . . . | Crusader |
| Plant setting ability cold | Normal |
| Plant setting ability hot | Normal |
| Resistances: | |
| Pepper Mottle Virus | Highly resistant |
| Xanthomonas campestris pv. vesicatoria, race 1 | Highly resistant |
| Xanthomonas campestris pv. vesicatoria, race 2 | Highly resistant |
| Xanthomonas campestris pv. vesicatoria, race 3 | Highly resistant |
| Xanthomonas campestris pv. vesicatoria, race 4 | Highly resistant |
| Xanthomonas campestris pv. vesicatoria, race 5 | Highly resistant |
| Xanthomonas campestris pv. vesicatoria, race 6 | Susceptible |
| Xanthomonas campestris pv. vesicatoria, race 7 | Highly resistant |
| Xanthomonas campestris pv. vesicatoria, race 8 | Highly resistant |
| Xanthomonas campestris pv. vesicatoria, race 9 | Highly resistant |

Breeding Methods.

This invention is also directed to methods for producing a pepper plant by crossing a first parent pepper plant with a second parent pepper plant wherein the first or second parent pepper plant is a plant of pepper cultivar 8728C, 16452A, 16452B, 16452C, RPP 25822, RPP 26098 or RPP 26105. Further, both first and second parent pepper plant can be selected from pepper cultivar 8728C, 16452A, 16452B, 16452C, RPP 25822, RPP 26098 or RPP 26105. Thus, any of the following exemplary methods using pepper cultivar 8728C, 16452A, 16452B, 16452C, RPP 25822, RPP 26098 or RPP 26105 are part of this invention: selfing, backcrosses, hybrid production, crosses to populations, doubled haploid production, and the like. All plants produced using pepper cultivar 8728C, 16452A, 16452B, 16452C, RPP 25822, RPP 26098 or RPP 26105 as at least one parent are within the scope of this invention, including those developed from pepper plants derived from pepper cultivar 8728C, 16452A, 16452B, 16452C, RPP 25822, RPP 26098 or RPP 26105. Advantageously, pepper cultivar 8728C, 16452A, 16452B, 16452C, RPP 25822, RPP 26098 or RPP 26105 can be used in crosses with other, different, pepper plants to produce the first generation (F1) pepper hybrid seeds and plants with desirable characteristics. The pepper plants of the invention can also be used for transformation where exogenous transgenes are introduced and expressed by the plants of the invention. Genetic variants created either through traditional breeding methods or through transformation of the cultivars of the invention by any of a number of protocols known to those of skill in the art are intended to be within the scope of this invention.

The following describes exemplary breeding methods that may be used with pepper cultivar 8728C, 16452A, 16452B, 16452C, RPP 25822, RPP 26098 or RPP 26105 in the development of further pepper plants. One such embodiment is a method for developing pepper cultivar 8728C, 16452A, 16452B, 16452C, RPP 25822, RPP 26098 or RPP 26105 progeny pepper plants in a pepper plant breeding program comprising: obtaining a plant, or a part thereof, of pepper cultivar 8728C, 16452A, 16452B, 16452C, RPP 25822, RPP 26098 or RPP 26105, utilizing said plant or plant part as a source of breeding material, and selecting a pepper cultivar 8728C, 16452A, 16452B, 16452C, RPP 25822, RPP 26098 or RPP 26105 progeny plant with molecular markers in common with pepper cultivar 8728C, 16452A, 16452B, 16452C, RPP 25822, RPP 26098 or RPP 26105 and/or with some, all or essentially all morphological and/or physiological characteristics of pepper cultivar 8728C, 16452A, 16452B, 16452C, RPP 25822, RPP 26098 or RPP 26105 (e.g., as described herein, in particular, in any one or more of Tables 1-9 or FIGS. 1-30). In representative embodiments, the progeny plant has at least 1, 2, 3, 4, 5, 6, 7, 8, 9, 10 or more of the morphological and physiological characteristics of pepper cultivar 8728C, 16452A, 16452B, 16452C, RPP 25822, RPP 26098 or RPP 26105 (e.g., as described herein, in particular, in any one or more of Tables 1-9 or FIGS. 1-30), or even all of the morphological and physiological characteristics of pepper cultivar 8728C, 16452A, 16452B, 16452C, RPP 25822, RPP 26098 or RPP 26105 so that said progeny pepper plant is not significantly different for said traits than pepper cultivar 8728C, 16452A, 16452B, 16452C, RPP 25822, RPP 26098 or RPP 26105, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of doubled haploids may be utilized.

Another representative method involves producing a population of pepper cultivar 8728C, 16452A, 16452B, 16452C, RPP 25822, RPP 26098 or RPP 26105 progeny plants, comprising crossing pepper cultivar 8728C, 16452A, 16452B, 16452C, RPP 25822, RPP 26098 or RPP 26105 with another pepper plant, thereby producing a population of pepper plants that, on average, derives at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from pepper cultivar 8728C, 16452A, 16452B, 16452C, RPP 25822, RPP 26098 or RPP 26105, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar 8728C, 16452A, 16452B, 16452C, RPP 25822, RPP 26098 or RPP 26105. One embodiment of this invention is the pepper plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles from pepper cultivar 8728C, 16452A, 16452B, 16452C, RPP 25822, RPP 26098 or RPP 26105. A plant of this population may be selected and repeatedly selfed or sibbed with a pepper plant resulting from these successive filial generations. Another approach is to make doubled haploid plants to achieve homozygosity.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). In embodiments, the invention encompasses progeny plants having a combination of at least 2, 3, 4, 5, 6, 7, 8, 9, 10 or more of the characteristics as described herein (e.g., in any one or more of Tables 1-9 or FIGS. 1-30) for pepper cultivar 8728C, 16452A, 16452B, 16452C, RPP 25822, RPP 26098 or RPP 26105, so that said progeny pepper plant is not significantly different for said traits than pepper cultivar 8728C, 16452A, 16452B, 16452C, RPP 25822, RPP 26098 or RPP 26105, as determined at the 5% significance level when grown in the same environmental conditions. Using techniques described herein and those known in the art, molecular markers may be used to identify said progeny plant as progeny of pepper cultivar 8728C, 16452A, 16452B, 16452C, RPP 25822, RPP 26098 or RPP 26105. Mean trait values may be used to determine whether trait differences are significant, and optionally the traits are measured on plants grown under the same environmental conditions.

Progeny of pepper cultivar 8728C, 16452A, 16452B, 16452C, RPP 25822, RPP 26098 or RPP 26105 may also be characterized through their filial relationship with pepper cultivar 8728C, 16452A, 16452B, 16452C, RPP 25822, RPP 26098 or RPP 26105, as for example, being within a certain number of breeding crosses of pepper cultivar 8728C, 16452A, 16452B, 16452C, RPP 25822, RPP 26098 or RPP 26105. A breeding cross is a cross made to introduce new genetics into the progeny, and is distinguished from a cross, such as a self or a sib cross or a backcross to 8728C, 16452A, 16452B, 16452C, RPP 25822, RPP 26098 or RPP 26105 as a recurrent parent, made to select among existing genetic alleles. The lower the number of breeding crosses in the pedigree, the closer the relationship between pepper cultivar 8728C, 16452A, 16452B, 16452C, RPP 25822, RPP 26098 or RPP 26105 and its progeny. For example, progeny produced by the methods described herein may be within 1, 2, 3, 4, 5 or more breeding crosses of pepper cultivar 8728C, 16452A, 16452B, 16452C, RPP 25822, RPP 26098 or RPP 26105.

In representative embodiments, a pepper plant derived from pepper cultivar 8728C, 16452A, 16452B, 16452C, RPP 25822, RPP 26098 or RPP 26105 comprises at least one set of chromosomes derived from pepper cultivar 8728C, 16452A, 16452B, 16452C, RPP 25822, RPP 26098 or RPP 26105.

In embodiments, the pepper plant or population of pepper plants derived from pepper cultivar 8728C, 16452A, 16452B, 16452C, RPP 25822, RPP 26098 or RPP 26105 comprises, on average, at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from pepper cultivar 8728C, 16452A, 16452B, 16452C, RPP 25822, RPP 26098 or RPP 26105, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar 8728C, 16452A, 16452B, 16452C, RPP 25822, RPP 26098 or RPP 26105.

In embodiments, the pepper plant derived from pepper cultivar 8728C, 16452A, 16452B, 16452C, RPP 25822, RPP 26098 or RPP 26105 is one, two, three, four, five or more breeding crosses removed from pepper cultivar 8728C, 16452A, 16452B, 16452C, RPP 25822, RPP 26098 or RPP 26105.

In representative embodiments, a plant derived from pepper cultivar 8728C, 16452A, 16452B, 16452C, RPP 25822, RPP 26098 or RPP 26105 is a doubled haploid plant, a hybrid plant or an inbred plant.

In embodiments, a hybrid or derived plant from pepper cultivar 8728C, 16452A, 16452B, 16452C, RPP 25822, RPP 26098 or RPP 26105 comprises a desired added trait. In representative embodiments, a pepper plant derived from pepper cultivar 8728C, 16452A, 16452B, 16452C, RPP 25822, RPP 26098 or RPP 26105 comprises all of the morphological and physiological characteristics of pepper cultivar 8728C, 16452A, 16452B, 16452C, RPP 25822, RPP 26098 or RPP 26105 (e.g., as described herein, in particular, in any one or more of Tables 1-9 or FIGS. 1-30). In embodiments, the pepper plant derived from pepper cultivar 8728C, 16452A, 16452B, 16452C, RPP 25822, RPP 26098 or RPP 26105 comprises all or essentially all of the morphological and physiological characteristics of pepper cultivar 8728C, 16452A, 16452B, 16452C, RPP 25822, RPP 26098 or RPP 26105 (e.g., as described herein, in particular, in any one or more of Tables 1-9 or FIGS. 1-30), with the addition of a desired added trait.

In embodiments, a hybrid or derived plant from pepper cultivar 8728C, 16452A, 16452B, 16452C, RPP 25822, RPP 26098 or RPP 26105 comprises QTL1 and/or QTL2 as described herein. In embodiments, the QTL1 and/or QTL2 is not in the native (e.g. natural) genetic background of the pepper plant having the extreme dark green color trait. In embodiments, the hybrid or derived plant comprises one or more of marker loci: SP436, SP626, SP693 and/or SP694. In embodiments, the hybrid or derived plant is homozygous for QTL1 and/or QTL2.

Further Embodiments of the Invention

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species or from the same species, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of pepper plants disclosed herein.

Genetic engineering techniques can be used (alone or in combination with breeding methods) to introduce one or more desired added traits into plant, for example, pepper cultivar 8728C, 16452A, 16452B, 16452C, RPP 25822, RPP 26098 or RPP 26105 or progeny or pepper plants derived thereof.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed pepper plants using transformation methods as described herein to incorporate transgenes into the genetic material of the pepper plant.

Additional methods include, but are not limited to, expression vectors introduced into plant tissues using a direct nucleic acid transfer method, such as microprojectile-mediated delivery (e.g., with a biolistic device), DNA injection, Agrobacterium-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

One commonly used selectable marker for plant transformation is a neomycin phosphotransferase II (nptII) coding sequence, for example, isolated from transposon Tn5, which when placed under the control of plant regulatory signals confers resistance to kanamycin. Fraley, et al., PNAS, 80:4803 (1983). Another commonly used selectable marker is hygromycin phosphotransferase, which confers resistance to the antibiotic hygromycin. Vanden Elzen, et al., Plant Mol. Biol., 5:299 (1985).

Additional selectable markers of bacterial origin that confer resistance to antibiotics include gentamycin acetyl transferase, streptomycin phosphotransferase, aminoglycoside-3'-adenyl transferase, the bleomycin resistance determinant. Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986). Other selectable markers confer resistance to herbicides such as glyphosate, glufosinate, or bromoxynil. Comai, et al., Nature, 317:741-744 (1985); Gordon-Kamm, et al., Plant Cell, 2:603-618 (1990); and Stalker, et al., Science, 242:419-423 (1988).

Selectable markers for plant transformation that are not of bacterial origin include, for example, mouse dihydrofolate reductase, plant 5-enolpyruvylshikimate-3-phosphate synthase, and plant acetolactate synthase. Eichholtz, et al., Somatic Cell Mol. Genet., 13:67 (1987); Shah, et al., Science, 233:478 (1986); and Charest, et al., Plant Cell Rep., 8:643 (1990).

Another class of selectable marker for plant transformation involves screening of presumptively transformed plant cells rather than direct genetic selection of transformed cells for resistance to a toxic substance such as an antibiotic. These selectable markers are particularly useful to quantify or visualize the spatial pattern of expression of a transgene in specific tissues and are frequently referred to as a reporter gene because they can be fused to transgene or regulatory sequence for the investigation of nucleic acid expression. Commonly used reporters for screening presumptively transformed cells include alpha-glucuronidase (GUS), alpha-galactosidase, luciferase and chloramphenicol, acetyltransferase. Jefferson, R. A., Plant Mol. Biol., 5:387 (1987); Teeri, et al., EMBO J., 8:343 (1989); Koncz, et al., PNAS, 84:131 (1987); and DeBlock, et al., EMBO J., 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., J. Cell Biol., 115:151a (1991).

Green Fluorescent Protein (GFP) is also utilized as a marker for nucleic acid expression in prokaryotic and eukaryotic cells. Chalfie, et al., Science, 263:802 (1994). GFP and mutants of GFP may be used as screenable markers.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters:

An inducible promoter is operably linked to a nucleic acid for expression in a plant. Optionally, the inducible promoter is operably linked to a nucleotide sequence encoding a signal sequence which is operably linked to a nucleic acid for expression in the plant. With an inducible promoter, the rate of transcription increases in response to an inducing agent.

Any inducible promoter can be used in the instant invention. See Ward, et al., Plant Mol. Biol., 22:361-366 (1993). Exemplary inducible promoters include, but are not limited to, that from the ACEI system which responds to copper (Melt, et al., PNAS, 90:4567-4571 (1993)); promoter from the In2 gene from maize which responds to benzenesulfonamide herbicide safeners (Hershey, et al., Mol. Gen. Genet., 227:229-237 (1991) and Gatz, et al., Mol. Gen. Genet., 243:

32-38 (1994)) or Tet repressor from Tn10 (Gatz, et al., Mol. Gen. Genet., 227:229-237 (1991)). A representative inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., PNAS, 88:0421 (1991).

B. Constitutive Promoters:

A constitutive promoter is operably linked to a nucleic acid for expression in a plant or the constitutive promoter is operably linked to a nucleotide sequence encoding a signal sequence which is operably linked to a nucleic acid for expression in a plant.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a nucleic acid for expression in a plant. Optionally, the tissue-specific promoter is operably linked to a nucleotide sequence encoding a signal sequence which is operably linked to a nucleic acid for expression in a plant. Plants transformed with a nucleic acid of interest operably linked to a tissue-specific promoter transcribe the nucleic acid of interest exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981).

According to a representative embodiment, the transgenic plant provided for commercial production of foreign protein is a pepper plant of the invention. In another embodiment, the biomass of interest is seed. For the relatively small number of transgenic plants that show higher levels of expression, a genetic map can be generated, for example via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons can involve hybridizations, RFLP, PCR, SSR, and sequencing, all of which are conventional techniques.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those categorized below:

A. Transgenes that Confer Resistance to Pests or Disease:

1. Plant disease resistance transgenes. Plant defenses are often activated by specific interaction between the product of a disease resistance gene (R) in the plant and the product of a corresponding avirulence (Avr) gene in the pathogen. A plant line can be transformed with a cloned resistance transgene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt delta-endotoxin gene. Moreover, DNA molecules encoding delta-endotoxin transgenes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several *Clivia miniata* mannose-binding lectin transgenes.

4. A vitamin-binding protein such as avidin. See, e.g., PCT Application No. US 93/06487. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57:1243 (1993) (nucleotide sequence of *Streptomyces nitrosporeus* alpha-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266,317 to Tomalski, et al., who disclose transgenes encoding insect-specific, paralytic neurotoxins.

8. An insect-specific venom produced in nature, by a snake, a wasp, etc. For example, see Pang, et al, Gene, 116:165 (1992), for disclosure of heterologous expression in plants of a transgene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase transgene. DNA molecules which contain chitinase-encoding sequences can be obtained, for example, from the ATCC under Accession Nos. 39637 and 67152. See also, Kramer, et al., Insect Biochem. Mol. Biol., 23:691 (1993), who teach the nucleotide sequence of a cDNA encoding tobacco hornworm chitinase, and Kawalleck, et al., Plant Mol. Biol., 21:673 (1993), who provide the nucleotide sequence of the parsley ubi4-2 polyubiquitin transgene.

11. A molecule that stimulates signal transduction. For example, see the disclosure by Botella, et al., Plant Mol. Biol., 24:757 (1994), of nucleotide sequences for mung bean calmodulin cDNA clones, and Griess, et al., Plant Physiol., 104: 1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance).

13. A membrane permease, a channel former, or a channel blocker. For example, see the disclosure of Jaynes, et al., Plant Sci., 89:43 (1993), of heterologous expression of a cecropin-beta, lytic peptide analog to render transgenic tobacco plants resistant to *Pseudomonas solanacearum.*

14. A viral-invasive protein or a complex toxin derived therefrom. For example, the accumulation of viral coat proteins in transformed plant cells imparts resistance to viral infection and/or disease development effected by the virus from which the coat protein transgene is derived, as well as by related viruses. See Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Intl Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., Nature, 366:469 (1993), who show that transgenic plants expressing recombinant antibody transgenes are protected from virus attack.

17. A developmental-arrestive protein produced in nature by a pathogen or a parasite. Thus, fungal endo-alpha-1,4-D-polygalacturonases facilitate fungal colonization and plant nutrient released by solubilizing plant cell wall homo-alpha-1,4-D-galacturonase. See Lamb, et al., Bio/technology, 10:1436 (1992). The cloning and characterization of a transgene which encodes a bean endopolygalacturonase-inhibiting protein is described by Toubart, et al., Plant J., 2:367 (1992).

18. A developmental-arrestive protein produced in nature by a plant. For example, Logemann, et al., Bio/technology, 10:305 (1992), have shown that transgenic plants expressing the barley ribosome-inactivating transgene have an increased resistance to fungal disease.

19. A lettuce mosaic potyvirus (LMV) coat protein transgene introduced into *Lactuca sativa* in order to increase its resistance to LMV infection. See Dinant, et al., Mol. Breeding, 3:1, 75-86 (1997).

Any disease or present resistance transgenes, including those exemplified above, can be introduced into a pepper plant of the invention through a variety of means including but not limited to transformation and breeding.

B. Transgenes that Confer Resistance to an Herbicide:

Exemplary polynucleotides encoding polypeptides that confer traits desirable for herbicide resistance include acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) transgene, including but not limited to those described in U.S. Pat. Nos. 4,940,935, 5,188,642, 5,633,435, 6,566,587, 7,674,598 as well as all related application; or the glyphosate N-acetyltransferase (GAT) transgene, described in Castle et al., Science, 2004, 304:1151-1154; and in U.S. Patent Application Publication Nos. 20070004912, 20050246798, and 20050060767)); glufosinate resistance (e.g., BAR; see e.g., U.S. Pat. No. 5,561,236); 2,4-D resistance (e.g., aryloxy alkanoate dioxygenase or AAD-1, AAD-12, or AAD-13), HPPD resistance (e.g., *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone); a cytochrome P450 or variant thereof that confers herbicide resistance or tolerance to, inter alia, HPPD-inhibiting herbicides, PPO-inhibiting herbicides and ALS-inhibiting herbicides (U.S. Patent Application Publication No. 20090011936; U.S. Pat. Nos. 6,380,465; 6,121,512; 5,349, 127; 6,649,814; and 6,300,544; and PCT International Publication No. WO 2007/000077); dicamba resistance (e.g., dicamba monoxygenase), and traits desirable for processing or process products such as high oil (e.g., U.S. Pat. No. 6,232,529); modified oils (e.g., fatty acid desaturase transgenes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., J. Bacteriol., 1988, 170:5837-5847) facilitate expression of polyhydroxyalkanoates (PHAs)).

In embodiments, the polynucleotide encodes a polypeptide conferring resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

Any transgene conferring herbicide resistance, including those exemplified above, can be introduced into the pepper plants of the invention through a variety of means including, but not limited to, transformation (e.g., genetic engineering techniques) and crossing.

C. Transgenes that Confer or Contribute to a Value-Added Trait:

1. Increased iron content of the pepper, for example, by introducing into a plant a soybean ferritin transgene as described in Goto, et al., Acta Horticulturae., 521, 101-109 (2000).

2. Decreased nitrate content of leaves, for example, by introducing into a pepper a transgene coding for a nitrate reductase. See, for example, Curtis, et al., Plant Cell Rep., 18:11, 889 896 (1999).

3. Increased sweetness of the pepper by introducing a transgene coding for monellin that elicits a flavor 100,000 times sweeter than sugar on a molar basis. See Penarrubia, et al., Bio/technology, 10:561-564 (1992).

4. Modified fatty acid metabolism, for example, by introducing into a plant an antisense sequence directed against stearyl-ACP desaturase to increase stearic acid content of the plant. See Knultzon, et al., PNAS, 89:2625 (1992).

5. Modified carbohydrate composition effected, for example, by introducing into plants a transgene coding for an enzyme that alters the branching pattern of starch. See Shiroza, et al., J. Bacteria, 170:810 (1988) (nucleotide sequence of *Streptococcus* mutants fructosyltransferase transgene); Steinmetz, et al., Mol. Gen. Genet., 20:220 (1985) (nucleotide sequence of *Bacillus subtilis* levansucrase transgene); Pen, et al., Bio/technology, 10:292 (1992) (production of transgenic plants that express *Bacillus licheniformis* alpha-amylase); Elliot, et al., Plant Mol. Biol., 21:515 (1993) (nucleotide sequences of tomato invertase transgenes); Sogaard, et al., J. Biol. Chem., 268:22480 (1993) (site-directed mutagenesis of barley alpha-amylase transgene); and Fisher, et al., Plant Physiol., 102:1045 (1993) (maize endosperm starch branching enzyme II).

6. Delayed and/or attenuated symptoms to Bean Golden Mosaic Geminivirus (BGMV), for example by transforming a plant with antisense genes from the Brazilian BGMV. See Arago et al., Molecular Breeding. 1998, 4: 6, 491-499.

7. Increased methionine content by introducing a transgene coding for a methionine-rich storage albumin (2S-albumin) from the Brazil nut, e.g., as described in Arago et al., Genetics and Molecular Biology. 1999, 22: 3, 445-449.

Any transgene that confers or contributes a value-added trait, including those exemplified above, can be introduced into the pepper plants of the invention through a variety of means including, but not limited to, transformation (e.g., genetic engineering techniques) and crossing.

D. Transgenes that Control Male-Sterility:

1. Introduction of a deacetylase transgene under the control of a tapetum-specific promoter and with the application of the chemical N—Ac-PPT. See, e.g., International Publication WO 01/29237.

2. Introduction of various stamen-specific promoters. See, e.g., International Publications WO 92/13956 and WO 92/13957.

3. Introduction of the barnase and the barstar transgenes. See, e.g., Paul, et al., Plant Mol. Biol., 19:611-622 (1992).

Any transgene that controls male sterility, including those exemplified above, can be introduced into the pepper plants of the invention through a variety of means including, but not limited to, transformation (e.g., genetic engineering techniques) and crossing.

Those skilled in the art will appreciate that any of the traits described above with respect to plant transformation methods can be introduced into a plant of the invention (e.g., pepper cultivar 8728C, 16452A, 16452B, 16452C, RPP 25822, RPP 26098 or RPP 26105 and hybrid pepper plants and other pepper plants derived therefrom) using breeding techniques.

Methods for Plant Transformation.

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993).

A. *Agrobacterium*-Mediated Transformation.

One method for introducing an expression vector into plants is based on the natural transformation system of *Agrobacterium*. See, for example, Horsch, et al., Science, 227: 1229 (1985); Curtis, et al., Journal of Experimental Botany, 45:279, 1441-1449 (1994); Torres, et al., Plant Cell Tissue and Organ Culture, 34:3, 279-285 (1993); and Dinant, et al., Molecular Breeding, 3:1, 75-86 (1997). *A. tumefaciens* and *A. rhizogenes* are plant pathogenic soil bacteria which genetically transform plant cells. The Ti and Ri plasmids of *A.*

*tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated transgene transfer are provided by Gruber, et al., supra, Miki, et al., supra, and Moloney, et al., Plant Cell Rep., 8:238 (1989). See also, U.S. Pat. No. 5,591, 616 issued Jan. 7, 1997.

B. Direct Transgene Transfer.

Several methods of plant transformation collectively referred to as direct transgene transfer have been developed as an alternative to *Agrobacterium*-mediated transformation. A generally applicable method of plant transformation is microprojectile-mediated transformation wherein DNA is carried on the surface of microprojectiles measuring 1 micron to 4 micron. The expression vector is introduced into plant tissues with a biolistic device that accelerates the microprojectiles to speeds of 300 m/s to 600 m/s which is sufficient to penetrate plant cell walls and membranes. Russell, D. R., et al., Plant Cell Rep., 12 (3, January), 165-169 (1993); Aragao, F. J. L., et al., Plant Mol. Biol., 20 (2, October), 357-359 (1992); Aragao, F. J. L., et al., Plant Cell Rep., 12 (9, July), 483-490 (1993); Aragao, Theor. Appl. Genet., 93:142-150 (1996); Kim, J., Minamikawa, T., Plant Sci., 117:131-138 (1996); Sanford, et al., Part. Sci. Technol., 5:27 (1987); Sanford, J. C., Trends Biotech., 6:299 (1988); Klein, et al., Bio/technology, 6:559-563 (1988); Sanford, J. C., Physiol. Plant, 7:206 (1990); Klein, et al., Bio/technology, 10:268 (1992).

Another method for physical delivery of DNA to plants is sonication of target cells. Zhang, et al., Bio/technology, 9:996 (1991). Alternatively, liposome and spheroplast fusion have been used to introduce expression vectors into plants. Deshayes, et al., EMBO J., 4:2731 (1985) and Christou, et al., PNAS, 84:3962 (1987). Direct uptake of DNA into protoplasts using $CaCl_2$ precipitation, polyvinyl alcohol, or poly-L-ornithine has also been reported. Hain, et al., Mol. Gen. Genet., 199:161 (1985) and Draper, et al., Plant Cell Physiol., 23:451 (1982). Electroporation of protoplasts and whole cells and tissues have also been described. Saker, M., Kuhne, T., Biologia *Plantarum*, 40(4):507-514 (1997/98); Donn, et al., In Abstracts of VIIth International Congress on Plant Cell and Tissue Culture IAPTC, A2-38, p. 53 (1990); D'Halluin, et al., Plant Cell, 4:1495-1505 (1992); and Spencer, et al., Plant Mol. Biol., 24:51-61 (1994). See also Chupean, et al., Bio/technology, 7:5, 503-508 (1989).

Following transformation of plant target tissues, expression of the above-described selectable marker transgenes allows for preferential selection of transformed cells, tissues and/or plants, using regeneration and selection methods now well known in the art.

The foregoing methods for transformation would typically be used for producing a transgenic pepper line. The transgenic pepper line could then be crossed with another (non-transformed or transformed) line in order to produce a new transgenic pepper line. Alternatively, a genetic trait that has been engineered into a particular plant cultivar using the foregoing transformation techniques could be introduced into another line using traditional breeding (e.g., backcrossing) techniques that are well known in the plant breeding arts. For example, a backcrossing approach could be used to move an engineered trait from a public, non-elite inbred line into an elite inbred line, or from an inbred line containing a foreign transgene in its genome into an inbred line or lines which do not contain that transgene.

Gene Conversions.

When the term "pepper plant" is used in the context of the present invention, this term also includes any gene conversions of that plant or variety. The term "gene converted plant" as used herein refers to those pepper plants that are developed, for example, by backcrossing, genetic engineering and/or mutation, wherein essentially all of the desired morphological and physiological characteristics of a variety (e.g., as described herein, in particular, in any one or more of Tables 1-9 or FIGS. 1-30) are recovered in addition to the one or more genes transferred into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene for the desired characteristic is termed the "nonrecurrent" or "donor parent." This terminology refers to the fact that the nonrecurrent parent is generally used one time in the breeding e.g., backcross) protocol and therefore does not recur. The gene that is transferred can be a native gene, a mutated native gene or a transgene introduced by genetic engineering techniques into the plant (or ancestor thereof). The parental plant into which the gene(s) from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred gene(s) and associated trait(s) from the nonrecurrent parent.

Many gene traits have been identified that can be improved by backcrossing techniques. Gene traits may or may not be transgenic. Examples of these traits include, but are not limited to, male sterility, modified fatty acid metabolism, modified carbohydrate metabolism, herbicide resistance, pest or disease resistance (e.g., resistance to bacterial, fungal, or viral disease such as resistance to *Xanthomonas campestris* pv. *Vesicatoria* [e.g., race 6]), insect resistance, enhanced nutritional quality, increased sweetness, increased flavor, improved ripening control, improved salt tolerance, industrial usage, yield stability, and yield enhancement. These genes are generally inherited through the nucleus.

Tissue Culture.

Further reproduction of pepper plants variety can occur by tissue culture and regeneration. Tissue culture of various tissues of pepper and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells which upon growth and differentiation produce pepper plants having desired characteristics of pepper cultivar 8728C, 16452A, 16452B, 16452C, RPP 25822, RPP 26098 or RPP 26105 (e.g., as described herein, in particular, in any one or more of Tables 1-9 or FIGS. 1-30). Optionally, pepper plants can be regenerated from the tissue culture of the invention comprising all or essentially all of the physiological and morphological characteristics of pepper cultivar 8728C, 16452A, 16452B, 16452C, RPP 25822, RPP 26098 or RPP 26105.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, fruits and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

DEPOSIT INFORMATION

Applicants have made a deposit of at least 2500 seeds of pepper cultivars RPP 25822, RPP 26098, RPP 26105, 16452A, 16452B and 16452C with the American Type Culture Collection (ATCC), 10801 University Boulevard, Manassas, Va., 20110-2209 U.S.A. on Jan. 30, 2015 under ATCC Deposit Nos. PTA-121983, PTA-121984, PTA-121982, PTA-121980, PTA-121981 and PTA-121985, respectively.

In addition, a seed deposit of *Capsicum annuum* 8728C was made with the NCIMB, Ferguson Building, Craibstone Estate, Bucksburn, Aberdeen AB21 9YA, Scotland, UK on Jul. 29, 2011 under the provisions of the Budapest Treaty.

These deposits of pepper varieties RPP 25822, RPP 26098, RPP 26105, 8728C, 16452A, 16452B and 16452C will be maintained in the ATCC or NCIMB depositories, respectively, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§1.801-1.809, including providing an indication of the viability of the samples. During the pendency of this application, access to the deposited material will be afforded to the Commissioner on request. All restrictions on the availability of the deposited material from the ATCC to the public will be irrevocably removed upon granting of the patent. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC §2321 et seq.).

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2500 seeds of the same variety with the American Type Culture Collection, 10801 University Boulevard, Manassas, Va. 20110-2209 U.S.A.

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the instant inbred and the like may be practiced within the scope of the invention.

Example 1

Identification of Extreme Dark Green Color Trait

Germplasm and Population Development

A breeding strategy was designed to identify the extreme dark green fruit color from pungent ancho chile peppers into sweet blocky peppers. An initial hybrid cross was made by crossing ancho 'San Luis' (extreme dark green source) with a blocky breeding line. The F1 from this cross was used to generate a segregating F2 population. F2 Individuals with the extreme dark green fruit color and blocky shape were selected based on visual appearance, followed by selfing and conventional pedigree selection for the extreme dark green color trait for seven generations, to create stable fixed inbred lines. Stable extreme dark green inbred lines were testcrossed to one another to develop extreme dark green hybrid varieties. Isolation of the genetic factors responsible for extreme dark green was simultaneously pursued following a quantitative trait loci discovery approach. A mapping population was generated by crossing an extreme dark green inbred with a non-extreme dark green inbred. The resulting hybrid was used to generate a dihaploid population via anther culture. The segregating dihaploid population was phenotyped for the extreme dark green color trait using a categorical scale to classify lines as extreme dark green or non-extreme dark green, and using colorimetry to obtain quantitative and objective color data for each line (see below material & methods) as well as using pigments content measurement. The categorical scale was based on visually matching fruit with color reference cards labeled from 1 (light) to 9 (dark), where 9 represented the extreme dark green phenotype.

An extreme dark green pepper plant *Capsicum annuum*, 8728C, produces fruit which at immature harvestable stage exhibit the extreme dark green color trait.

Plant 8728C was crossed with inbred line 16452, which also produces extreme dark green fruits, to produce hybrid RPP 25965. Hybrid RPP 25964 also produces extreme dark green pepper fruits.

Further characterization and definition of the trait was accomplished by screening a panel of germplasm ranging in phenotype from regular green to extreme dark green.

To this end, several green pepper varieties available on the market were used and evaluated by visual ranking with color reference, but also by colorimetry measurement and by measuring the content of select pigments.

The pepper varieties available on the market that were tested were: Crusader (Rogers), Encore (Rogers), Declaration (Harris Moran), Aristotle (Harris Seeds), Karisma (Harris Moran), Hunter (Rogers), Tomcat (Rogers), 8302 (Seminis), 7141 (Seminis) and 1819 (Seminis).

It has been determined that the color measurement by objective means with a colorimeter correlates with chlorophyll A&B, lutein and violaxanthin content. That is to say that the deeper the color is, the higher the content of the pepper fruits in those pigments.

Table 2 shows the correlation between colorimetry values and pigment content of the pepper fruits analyzed according to the present invention.

This clearly shows that the pigment content of the pepper fruits according to the present invention bearing the extreme dark green color trait relates to dark green color as evaluated by either subjective eye-visual perception or objective colorimetry.

Table 2 also shows the correlation between pigment contents and colorimeter values measured for pepper fruits of pepper plants according to the present invention grown in different areas, i.e. Gilroy (California, USA), Naples (Florida, USA) and El Ejido (Spain).

From Table 2 it appears that the values of the different measured parameters are not affected by environmental conditions and thus shows that the phenotype of extreme dark green color, either evaluated by colorimeter measurement or by pigments contents is controlled by genetic determinants contained in the genome of the said plants.

Phenotyping

Fruit color and metabolite (pigment) measurements of a germplasm panel representing pepper varieties with and without the extreme dark green color trait.

Thirty six *C. annuum* varieties comprised of inbred lines and F1 hybrids were grown in summer 2010 in Gilroy, Calif. under standard field conditions, in autumn 2010/winter 2011 in El Ejido, Spain under standard passive greenhouse conditions, and in spring 2011 in Naples, Fla. under standard field conditions. This germplasm panel was assembled to allow direct comparisons of pepper germplasm with and without the extreme dark green color trait and demonstrate that pepper plants with the extreme dark green color trait are darker/more intense in green color with higher fruit pigment levels. Multiple trial locations were used to demonstrate the behavior of the trait across environments and growing conditions.

A randomized and replicated block design was used for laying out experimental plots, and a plot was treated as the experimental unit, with 5 random fruit selected to represent the plot.

Samples from the 5 fruit were pooled for pigment measurements, and color data for the 5 fruit were summarized to provide a representative data set for the variety and replicate.

Materials and Methods

Environmental conditions, including light source, object size, color background, and angle of vision or illumination can affect how a colored object appears to a human observer. In order to overcome this subjectivity, color measurement systems and instruments have been developed for quantifying colors and expressing colors in terms of three variables which completely and uniquely describe the color. A complete discussion of color measurement theory can be found in: Berns, R. 2000. Billmeyer and Saltzman's principles of color technology. Wiley. Malacara, D. 2002. Color vision and colorimetry theory and applications. SPIE Press.

To measure fruit color, two experimental methodologies were used, colorimetry/spectrophotometry, and image analysis via a computer vision system. To measure fruit pigment contents, reversed phase liquid chromatography and UV DAD detection were used.

Colorimetry/spectrophotometry

A Konica Minolta colorimeter model CR-400 was used in California and Florida to generate color data on pepper fruits, using the CIELAB L*a*b* color space, C illuminant, and 2 degree angle of observer. The colorimeter was operated using the 8 mm aperture measuring head and Spectramagic NX software version 1.9. A Konica Minolta hand-held spectrophotometer model CM-2500d with 8 mm measurement aperture was used in Spain to generate color data on pepper fruits, using the CIELAB L*a*b* color space, C and D65 illuminant, and 10 degree angle of observer. The spectrophotometer was operated using Spectramagic NX software version 3.6. In all three locations, the instrument was calibrated prior to and during use according to the manufacturer's instructions. Fruit samples were harvested from each plot at immature (e.g. unripe, fully physiologically developed) stage and brought to the lab for further processing. The surface of each fruit was cleaned by gently wiping with a damp paper towel to remove any dirt or debris. The measurement aperture was then held in tight connection against the surface of the fruit, to ensure no infiltration of external sources of light, and three measurements were taken, moving the aperture to three random representative spots on the fruit surface between measurements.

The CIELAB color scale is used widely by the food industry to measure color and demonstrate differences in color. The scale includes 3 data variables, L*, a*, and b*. L* indicates darkness/lightness on a 0 to 100 scale, where 0 is black and 100 is white. The variables a* and b* indicate the amount of red, green, blue, and yellow color: +a* is the red direction, −a* is the green direction, +b* is the yellow direction, and −b* is the blue direction. Differences in color between two samples can be expressed in terms of the change in L*, a*, and/or b*.

Image Analysis

Computer vision systems (CVS) can be used to measure the whole distribution of color on a fruit surface, by translating the RGB pixel colors of a digital sample image into CIELAB L*a*b* values. Algorithms used by the image analysis software correct for the cameras' own color characteristics, fruit glossiness and fruit curvature, and calibrate the system.

CVS systems were used in California, Florida, and Spain to generate color data on pepper fruits. The systems consisted of the following hardware and software components:

Camera, Canon EOS Digital Rebel XT (Florida and California); EOS 450D (Spain)

Standardized lighting system, Westcott SpiderliteTD5 Location Kit with Westcott 27W/110V Daylt FLOU lamps X-Rite Digital Color Checker SG card for color calibration Lastolite EZY grey balance card, for white balance calibration Photoflex medium LiteRoom table top shooting white tent Flocked paper (Savage) and velvet fabric photographic background Image version (1.45)

Color transformer plug-in for ImageJ; Macro programs to automate image processing Photography was conducted in a room with no windows to ensure that the lighting system was the only source of illumination. Lamps were placed at equal distances from the sample platform and equal heights from the floor to center of the back of the light head. Lamp heads were angled at 45 degrees to the sample platform. Prior to taking photographs, lamps were turned on and allowed to warm up for at least 10 minutes. The background material was placed on the sample platform and the white tent placed on top of the background, with zipper opening facing out. The camera was mounted on a stand with the lens pointing down and positioned over the tent, at a fixed distance from the top of the table.

The camera was manually calibrated for white balance (uniformity of illumination within the photo field) and color at the beginning of each sample evaluation day. The same fruit samples used for collection of color data via colorimeter/spectrophotometer were used for the CVS and were placed inside the tent on the background. Fruits were spaced evenly in the photo field, not touching each other and not in the shadows of one another, and the tent was closed. The photographs were taken through an opening in the top of the tent.

Photographs were processed using the ImageJ software program, version 1.95, and a proprietary macro developed for automation of the processing. Pixels in the digital photographs were identified by the software as either background or sample, and the RGB color values of each sample pixel were translated by the software into CIELAB L*a*b* color values using a color calibration algorithm. The macro then calculated summary statistics for all the color values of the sample pixels in each photograph of fruit samples.

Reversed Phase Liquid Chromatography and UV DAD Detection

The same fruit sample used for color analysis via colorimetry/spectrophotometry and image analysis was further analyzed for pigment content. Each of the five fruits comprising a sample was cut into pieces, removing and discarding the peduncle, seeds, and placental tissue, leaving only the pericarp. Pericarp pieces were combined in a blender (Waring model 61BL30) and processed to form a homogenous puree. An antifoaming agent (Silicone Anti-foam SAG 1572), 10 µL to 100 g pepper, was added to the blended puree to prevent splitting into aqueous and foam layers and to keep the pepper puree homogeneous during subsampling. 1.5 mL aliquots of the homogenized pepper pericarp were sub-sampled into 3.5 mL cryo vials, which were flash-frozen in liquid nitrogen and stored at −80° C. until analysis. Frozen puree samples were freeze dried and milled, then extracted twice with tert-butyl-methyl-ether (TBME) and twice with methanol. Extracts were analyzed and separated into pigment components using an Agilent 1100 HPLC with binary pump and YMC C30 column. The injection volume was 10 µL (standard injection) and eluent flow was 0.5 mL/minute. Detection was via UV DAD.

Data Processing

Chromatograms were processed using Agilent Chemstation® software, to integrate and identify peaks. UV spectra were checked for each peak against that of library spectra before the identification was accepted. For quantitation the response factor of the calibrated reference compounds was calculated and used for the non-calibrated peaks.

```
SEQUENCES
                                              SEQ ID NO: 1
5'AGATATTCCCTCCCTCTTCATTATTCCT 3'

SEQ ID NO: 2
5'GAGGCTGCACGAACAGATCA 3'

SEQ ID NO: 3
5'GTGAAGGAAGCGTGATGAATGG 3'

SEQ ID NO: 4
5'CCTAACAGCACTTCAGGTGCAA 3'

SEQ ID NO: 5
5'ACGAGGATGCAACTGACTCAAAA 3'

SEQ ID NO: 6
5'CCCAAGTCACTAGGTTGTTGATTCT 3'

SEQ ID NO: 7
5'TCTTATTGGAGCAAAGAATAACTGGGTTAT 3'

SEQ ID NO: 8
5'TGCACTCTATGTGTTTGATATTTTGTCTCA 3'

SEQ ID NO: 9
5'CTGGAGTTACCAGTTTATA 3'
```

-continued
```
                                              SEQ ID NO: 10
5'TAGTACGGTGTGCCAACAA 3'

SEQ ID NO: 11
5'ATGATGCGAATGGTCA 3'

SEQ ID NO: 12
5'TGTAGCTTCAATCTATTTGTTC 3'
```

Example 2

Genotyping and QTL Discovery

A bi-parental population of 188 fixed lines was developed for the purpose of QTL mapping. The population was genotyped with a set of genome wide markers. The QTL analysis following standard practice was done with QTL Cartographer software. Raw phenotypic data was used in the analysis.

Two QTL (QTL1 and QTL2) were identified at <0.01% significance with markers, SP436 & SP626 on the one hand and SP693 & SP694 on the other hand, showing the highest association (linkage) with QTL1 and QTL2 respectively.

```
QTL 1
Marker locus SP 436
                                              (SEQ ID NO: 1)
Forward primer: 5' AGATATTCCCTCCCTCTTCATTATTCCT 3'

(SEQ ID NO: 2)
Reverse primer: 5' GAGGCTGCACGAACAGATCA 3'

Extreme dark green allele specific probe:
                                              (SEQ ID NO 9)
5' CTGGAGTTACCAGTTTATA 3'

Probe sequence was labelled with FM at the 5' end
and with MGB-NFQ at the 3' end Marker locus SP626
                                              (SEQ ID NO: 3)
Forward primer: 5' GTGAAGGAAGCGTGATGAATGG 3'

(SEQ ID NO: 4)
Reverse primer: 5' CCTAACAGCACTTCAGGTGCAA 3'

Extreme dark green allele specific probe:
                                              (SEQ ID NO 10)
5' TAGTACGGTGTGCCAACAA 3'.

Probe sequence was labelled with VC at the 5' end
and with MGB-NFQ at the 3' end.

QTL2
Marker locus SP693
                                              (SEQ ID NO: 5)
Forward primer: 5' ACGAGGATGCAACTGACTCAAAA 3'

(SEQ ID NO: 6)
Reverse primer: 5' CCCAAGTCACTAGGTTGTTGATTCT 3'

Extreme dark green allele specific probe:
                                              (SEQ ID NO 11)
5' ATGATGCGAATGGTCA 3'

Probe sequence was labelled with VC at the 5'end
Marker locus SP694and with MGB-NFQ at the 3'end.
```

-continued

Forward primer: 5' TCTTATTGGAGCAAAGAATAACTGGGTTA T 3' (SEQ ID NO: 7)

Reverse primer: 5' TGCACTCTATGTGTTTGATATTTTGTCTC A 3' (SEQ ID NO: 8)

Extreme dark green allele specific probe:
(SEQ ID NO 12)
5' TGTAGCTTCAATCTATTTGTTC 3'

Probe sequence was labelled with VC at the 5' end and with MGB-NFQ at the 3' end.

Table 3 shows the content in violaxanthin, Chlorophyll A and Chlorophyll B, lutein and beta-carotene for the various pepper plants chosen for the trials as well as plant 8728C and hybrid RPP25965. This table also shows the different colorimeter values of those plants. It clearly shows that the plant according to the inventions are different from existing blocky pepper varieties available on the market and do clearly differentiate from those.

Table 4 also shows a QTL validation of the extreme dark green color trait according to the present invention. Various individuals, including doubled haploid plant derived from the population generated for QTL discovery, with different genetic profiles, either none of the QTL according to the present invention, only one, or both of QTL1 and QTL2 of the present invention.

Results of Table 4 clearly show the contribution of both QTL1 and QTL2 to the pigment content. It appears that both QTL lead to the increased content of violaxanthin, lutein, chlorophyll A and Chlorophyll B.

TABLE 2

| | Viola xanthin-Gilroy | Lutein-Gilroy | Chloro-phyll A-Gilroy | Chloro-phyll B-Gilroy | b-caro-tene-Gilroy | L*(C)-Gilroy | a*(C)-Gilroy | b*(C)-Gilroy |
|---|---|---|---|---|---|---|---|---|
| Violaxanthin-Gilroy | 1 | | | | | | | |
| Lutein-Gilroy | 0.95 | 1 | | | | | | |
| Chlorophyll A-Gilroy | 0.96 | 0.99 | 1 | | | | | |
| Chlorophyll B-Gilroy | 0.96 | 1.00 | 1.00 | 1 | | | | |
| b-carotene - Gilroy | 0.97 | 0.97 | 0.99 | 0.98 | 1 | | | |
| L*(C)-Gilroy | −0.79 | −0.80 | −0.76 | −0.79 | −0.73 | 1 | | |
| a*(C)-Gilroy | 0.75 | 0.87 | 0.82 | 0.85 | 0.77 | −0.76 | 1 | |
| b*(C)-Gilroy | −0.74 | −0.86 | −0.80 | −0.83 | −0.76 | 0.77 | −0.99 | 1 |
| Violaxanthin-El Ejido | 0.93 | 0.93 | 0.94 | 0.94 | 0.93 | −0.76 | 0.75 | −0.72 |
| Lutein-El Ejido | 0.90 | 0.95 | 0.93 | 0.94 | 0.90 | −0.84 | 0.85 | −0.84 |
| Chlorophyll A-El Ejido | 0.92 | 0.96 | 0.95 | 0.96 | 0.93 | −0.82 | 0.84 | −0.82 |
| Chlorophyll B-El Ejido | 0.91 | 0.95 | 0.94 | 0.95 | 0.91 | −0.84 | 0.84 | −0.83 |
| b-carotene-El Ejido | 0.93 | 0.95 | 0.96 | 0.96 | 0.95 | −0.77 | 0.79 | −0.77 |
| L*(C)-El Ejido | −0.66 | −0.77 | −0.72 | −0.75 | −0.67 | 0.82 | −0.87 | 0.88 |
| a*(C)-El Ejido | 0.70 | 0.79 | 0.73 | 0.77 | 0.68 | −0.81 | 0.92 | −0.92 |
| b*(C)-El Ejido | −0.69 | −0.78 | −0.72 | −0.75 | −0.67 | 0.80 | −0.92 | 0.92 |
| Violaxanthin-Naples | 0.97 | 0.94 | 0.95 | 0.95 | 0.96 | −0.76 | 0.75 | −0.73 |
| Lutein-Naples | 0.96 | 0.98 | 0.98 | 0.99 | 0.97 | −0.81 | 0.85 | −0.84 |
| Chlorophyll A-Naples | 0.97 | 0.98 | 0.99 | 0.98 | 0.98 | −0.78 | 0.80 | −0.78 |
| Chlorophyll B-Naples | 0.97 | 0.98 | 0.99 | 0.99 | 0.98 | −0.80 | 0.81 | −0.80 |
| b-carotene-Naples | 0.97 | 0.95 | 0.97 | 0.96 | 0.98 | −0.75 | 0.76 | −0.74 |
| L*(C)-Naples | −0.69 | −0.80 | −0.75 | −0.78 | −0.69 | 0.84 | −0.82 | 0.82 |
| a*(C)-Naples | 0.80 | 0.81 | 0.78 | 0.81 | 0.74 | −0.87 | 0.87 | −0.86 |
| b*(C)-Naples | −0.79 | −0.81 | −0.77 | −0.80 | −0.74 | 0.88 | −0.88 | 0.88 |

| | Viola xanthin-El Ejido | Lutein-El Ejido | Chloro-phyll A-El Ejido | Chloro-phyll B-El Ejido | b-caro-tene-El Ejido | L*(C)-El Ejido | a*(C)-El Ejido | b*(C)-El Ejido |
|---|---|---|---|---|---|---|---|---|
| Violaxanthin-El Ejido | 1 | | | | | | | |
| Lutein-El Ejido | 0.96 | 1 | | | | | | |
| Chlorophyll A-El Ejido | 0.98 | 0.99 | 1 | | | | | |
| Chlorophyll B-El Ejido | 0.97 | 1.00 | 1.00 | 1 | | | | |
| b-carotene-El Ejido | 0.99 | 0.97 | 0.99 | 0.97 | 1 | | | |
| L*(C)-El Ejido | −0.70 | −0.81 | −0.78 | −0.79 | −0.73 | 1 | | |
| a*(C)-El Ejido | 0.73 | 0.84 | 0.82 | 0.84 | 0.75 | −0.89 | 1 | |
| b*(C)-El Ejido | −0.71 | −0.82 | −0.80 | −0.82 | −0.74 | 0.88 | −0.99 | 1 |
| Violaxanthin-Naples | 0.91 | 0.88 | 0.91 | 0.90 | 0.92 | −0.65 | 0.69 | −0.68 |
| Lutein-Naples | 0.92 | 0.93 | 0.96 | 0.95 | 0.94 | −0.74 | 0.78 | −0.77 |
| Chlorophyll A-Naples | 0.94 | 0.92 | 0.95 | 0.94 | 0.95 | −0.70 | 0.73 | −0.72 |
| Chlorophyll B-Naples | 0.95 | 0.94 | 0.96 | 0.95 | 0.96 | −0.72 | 0.75 | −0.74 |
| b-carotene - Naples | 0.91 | 0.88 | 0.92 | 0.90 | 0.93 | −0.65 | 0.68 | −0.68 |
| L*(C)-Naples | −0.73 | −0.83 | −0.79 | −0.81 | −0.74 | 0.77 | −0.77 | 0.76 |
| a*(C)-Naples | 0.77 | 0.84 | 0.83 | 0.85 | 0.77 | −0.82 | 0.90 | −0.89 |
| b*(C)-Naples | −0.76 | −0.84 | −0.82 | −0.84 | −0.76 | 0.83 | −0.91 | 0.91 |

| | Viola xanthin-Naples | Lutein-Naples | Chloro-phyll A-Naples | Chloro-phyll B-Naples | b-caro-tene-Naples | L*(C)-Naples | a*(C)-Naples | b*(C)-Naples |
|---|---|---|---|---|---|---|---|---|
| Violaxanthin-Naples | 1 | | | | | | | |
| Lutein-Naples | 0.97 | 1 | | | | | | |
| Chlorophyll A-Naples | 0.97 | 0.99 | 1 | | | | | |

TABLE 2-continued

| | | | | | | | | |
|---|---|---|---|---|---|---|---|---|
| Chlorophyll B-Naples | 0.97 | 0.99 | 1.00 | 1 | | | | |
| b-carotene-Naples | 0.98 | 0.98 | 0.99 | 0.98 | 1 | | | |
| L*(C)-Naples | −0.70 | −0.79 | −0.73 | −0.76 | −0.69 | 1 | | |
| a*(C)-Naples | 0.79 | 0.84 | 0.80 | 0.82 | 0.77 | −0.76 | 1 | |
| b*(C)-Naples | −0.78 | −0.84 | −0.79 | −0.81 | −0.76 | 0.78 | −0.99 | 1 |

TABLE 3

| Entry | Viola-xanthin | Lutein | Chlorophyll A | Chlorophyll B | b-carotene |
|---|---|---|---|---|---|
| Crusader | 1.87 | 4.08 | 20.6 | 5.54 | 1.20 |
| Encore | 1.42 | 3.51 | 17.6 | 4.67 | 1.07 |
| 8302 | 1.80 | 4.74 | 21.7 | 6.09 | 1.25 |
| 7141 | 1.77 | 5.20 | 24.6 | 6.83 | 1.44 |
| 1819 | 1.57 | 4.30 | 20.5 | 5.69 | 1.23 |
| Declaration | 1.65 | 3.60 | 17.9 | 4.85 | 1.11 |
| Aristotle | 1.61 | 3.45 | 17.5 | 4.70 | 1.12 |
| Karisma | 1.92 | 4.28 | 19.5 | 5.43 | 1.18 |
| Hunter | 1.98 | 4.24 | 21.0 | 5.89 | 1.17 |
| Tomcat | 2.04 | 4.27 | 21.1 | 5.89 | 1.23 |
| RPP 25965 | 4.37 | 8.04 | 33.8 | 10.50 | 1.76 |
| 8728C | 4.53 | 9.81 | 42.8 | 13.34 | 2.19 |
| Standard Deviation | 0.41 | 0.63 | 3.0 | 0.82 | 0.17 |
| F-test Probability | 0.0% | 0.0% | 0.0% | 0.0% | 0.0% |
| 5% LSD | 0.67 | 1.03 | 4.8 | 1.34 | 0.28 |

| Entry | L*(C) | a*(C) | b*(C) |
|---|---|---|---|
| Crusader | 38.3 | −10.6 | 13.5 |
| Encore | 40.7 | −11.7 | 16.2 |
| 8302 | 37.6 | −7.6 | 8.2 |
| 7141 | 38.2 | −8.2 | 8.6 |
| 1819 | 40.7 | −9.5 | 11.3 |
| Declaration | 40.7 | −9.7 | 11.7 |
| Aristotle | 40.9 | −10.1 | 12.4 |
| Karisma | 40.4 | −9.8 | 12.0 |
| Hunter | 36.5 | −8.9 | 10.3 |
| Tomcat | 37.8 | −9.9 | 12.3 |
| RPP 25965 | 34.4 | −5.1 | 4.3 |
| 8728C | 33.7 | −4.4 | 3.3 |
| Standard Deviation | 0.8 | 0.6 | 1.1 |
| F-test Probability | 0.0% | 0.0% | 0.0% |
| 5% LSD | 1.4 | 1.0 | 1.7 |

TABLE 4

| Entry | Violaxanthin | Lutein | Chlorophyll A | Chlorophyll B | b-carotene |
|---|---|---|---|---|---|
| 8728C, (QTL1 + QTL2) | 3.01 | 7.03 | 40.97 | 12.80 | 2.09 |
| 11498, (no QTL) | 1.09 | 1.97 | 14.23 | 3.92 | 0.92 |
| DH 16, (QTL1 + QTL2) | 2.40 | 6.53 | 37.38 | 11.70 | 1.88 |
| DH54, (QTL1) | 2.20 | 4.91 | 30.43 | 8.71 | 1.74 |
| DH69, (QTL2) | 1.91 | 4.59 | 27.88 | 7.98 | 1.64 |
| DH 11, (no QTL) | 1.16 | 3.12 | 20.48 | 5.66 | 1.24 |
| Standard Deviation | 0.37 | 0.72 | 3.98 | 1.15 | 0.25 |
| F-test Probability | 0.0% | 0.0% | 0.0% | 0.0% | 0.0% |
| 5% LSD | 0.59 | 1.17 | 6.47 | 1.88 | 0.40 |

| Entry | L*(C) | a*(C) | b*(C) |
|---|---|---|---|
| 8728C, (QTL1 + QTL2) | 36.99 | −4.74 | 3.84 |
| 11498, (no QTL) | 43.33 | −9.76 | 13.13 |
| DH 16, (QTL1 + QTL2) | 37.45 | −4.34 | 3.51 |
| DH54, (QTL1) | 38.26 | −6.83 | 6.54 |
| DH69, (QTL2) | 40.45 | −8.39 | 9.93 |
| DH 11, (no QTL) | 42.35 | −9.64 | 12.18 |
| Standard Deviation | 1.28 | 0.88 | 1.68 |
| F-test Probability | 0.0% | 0.0% | 0.0% |
| 5% LSD | 2.09 | 1.44 | 2.73 |

Example 3

Pigment Content of OVG Hybrids

Immature green fruits from a panel of OVG and non-OVG inbred and hybrid peppers were grown under standard field conditions in Gilroy Calif. in Summer 2010 and harvested in late summer for measurement of pigment content essentially as described above in Example 1. Levels of violaxanthin (FIG. 9), lutein (FIG. 10), chlorophyll A (FIG. 11), chlorophyll B (FIG. 12), alpha-carotene (FIG. 13), and beta-carotene (FIG. 14) were determined.

The different entries shown in the figures are indicated in Table 5 below.

TABLE 5

| Genotype | Pepper Entry | Variety |
|---|---|---|
| Non-OVG Hybrids | 1 | Crusader |
| | 2 | Encore |
| | 3 | 8302 |
| | 4 | 7141 |
| | 5 | 1819 |
| | 6 | Declaration |
| | 7 | Aristotle |
| | 8 | Karisma |
| Heterozygous OVG Hybrids | 9 | Hunter |
| | 10 | Tomcat |
| Homozygous OVG Hybrids | 11 | RPP 26098 |
| | 12 | RPP 26105 |
| OVG Inbreds | 13 | 8728C, OVG male inbred parent |
| | 14 | 16452A, OVG female inbred parent of RPP 25822 |
| | 15 | 16452B, OVG female inbred parent of RPP 26098 |
| | 16 | 16452C, OVG female inbred parent of RPP 26105 |
| Non-OVG Inbreds | 17 | Non-OVG inbred, female parent of Hunter |
| | 18 | Non-OVG inbred, female parent of Tomcat |
| | 19 | Non-OVG inbred, male parent of Encore |

The results demonstrate that fruits from homozygous OVG hybrids and OVG inbred lines have higher levels of pigments (violaxanthin, lutein, chlorophyll a, chlorophyll b, alpha-carotene, and beta-carotene) as compared with non-OVG fruit.

Similar results were also observed in a field trial conducted in Spring 2010 in Naples, Fla. under standard field conditions.

Example 4

Pigment Content of OVG Hybrids RPP 26105, RPP 26098, RPP 25822

In a further study, pigment content was assessed in immature green fruits from homozygous OVG Hybrids RPP 26105, RPP 26098, RPP 25822 in comparison with control varieties and varieties heterozygous for the extreme dark green trait.

Fruits were collected from a field trial conducted in Gilroy, Calif. in Summer 2013. sample of ten fruits of each variety were collected and evaluated. Briefly, fruits were harvested from a field trial consisting of three replication of 20 plants per replication. For each harvest, the fruits from each of the field replications per variety were pooled, and then the fruit samples were taken.

TABLE 6

| Value | RPP 26105 | RPP 26098 | RPP 25822 | Non-OVG Hybrid | Non-OVG Hybrid | Non-OVG Hybrid | OVG Heterozygote |
|---|---|---|---|---|---|---|---|
| β-carotene (IU/100 g) | 345 | 394 | 364 | 240 | 262 | 220 | 278 |
| Lutein (μg/g) | 62.7 | 41.0 | 49.3 | 19.3 | 23.8 | 19.2 | 24.1 |

These data confirm the results observed in Example 3 above that immature green fruit from homozygous OVG hybrids have an increased content of beta-carotene and lutein as compared with immature fruit from non-OVG hybrids or OVG heterozygotes.

Example 5

Analysis of Surface Color of OVG Hybrids

The pepper fruits collected in Example 3 were also evaluated for surface color. Colors were assessed by image analysis using the CIELAB scale (L, a*, b*) as described above in Example 1. Results are shown in FIG. 15 (L*), FIG. 16 (a*) and FIG. 17 (b*).

In general, the homozygous OVG hybrids and inbreds had a lower L* value (darker), a higher a* value (greener), and lower b* (bluer) value as compared with the other fruits evaluated.

Similar results were observed in a separate field trial conducted in Spring 2010 in Naples, Fla. under standard field conditions.

Example 6

Greenhouse Trial Conducted in El Ejido, Spain

A third trial was conducted under standard passive greenhouse conditions in El Ejido, Spain in Winter 2010-2011 (fruit measurements were done in January-February of 2011), using the same varieties and measurements described in Example 3 for the Gilroy open field trial.

Violaxanthin (FIG. 18), lutein (FIG. 19), chlorophyll A (FIG. 20), chlorophyll B (FIG. 21), alpha-carotene (FIG. 22), and beta-carotene (FIG. 23) content were determined.

In addition, the pepper fruits were evaluated for surface color. Colors were assessed by image analysis using the CIELAB scale (L, a*, b*) essentially as described above in Example 1. Results are shown in FIG. 24 (L*), FIG. 25 (a*), and FIG. 26 (b*).

These results were consistent with those observed in the field trials described in Examples 3 to 5 above.

Example 7

Color Analysis of Peduncle, Interior Flesh, and Calyx of OVG Hybrid Fruits

Immature green pepper fruits were harvested from two trials in Naples, Fla. (winter 2013) for color analysis of the peduncle, interior flesh and calyx. The first trial included 3 field replications (20 plants of each variety) and was harvested at 3 different times. The second trial included 2 replications (10 plants of each variety), also harvested at 3 different times. Fruits were selected in good condition from each harvest and replication for the color analysis (10 fruits for peduncle, 5 for calyx, and 10 for flesh for each variety). For each harvest, the fruits from each of the field replications per variety were pooled, and then the samples were taken.

Peduncle, interior flesh and calyx color were evaluated by colorimeter as described in Example 1, with the additional determination of the corresponding Munsell Color chip based on the L*, a* and b* values. Results of the colorimeter analysis are shown in Table 7 below.

TABLE 7

| Variety | L*(C) | a*(C) | b*(C) | Munsell Color Chip |
|---|---|---|---|---|
| Peduncle | | | | |
| Non-OVG hybrid | 46.514 | −15.182 | 25.618 | 5GY4/6 |
| Non-OVG hybrid | 50.136 | −15.706 | 26.952 | 5GY4/8 |
| Heterozygous OVG hybrid | 47.388 | −15.008 | 24.976 | 5GY4/6 |
| RPP 25822 | 46.1 | −14.368 | 23.372 | 5GY4/6 |
| RPP 26098 | 46.212 | −14.202 | 22.212 | 5GY4/6 |
| RPP 26105 | 44.75 | −13.826 | 21.992 | 5GY3/6 |
| Interior Flesh | | | | |
| Non-OVG hybrid | 39.866 | −13.164 | 23.788 | 5GY3/4 |
| Non-OVG hybrid | 41.398 | −15.328 | 30.454 | 5GY3/6 |
| Heterozygous OVG | 38.802 | −13.36 | 24.192 | 2.5G3/6 |
| RPP 25822 | 37.246 | −12.638 | 21.36 | 10GY2/4 |
| RPP 26098 | 33.984 | −13.186 | 21.924 | 2.5G2/4 |
| RPP 26105 | 35.952 | −12.17 | 19.892 | 10GY2/4 |
| Calyx | | | | |
| Non-OVG hybrid | 40.502 | −17.18 | 29.948 | 7.5GY3/4 |
| Non-OVG hybrid | 45.556 | −17.528 | 29.956 | 2.5GY4/4 |
| Heterozygous OVG hybrid | 39.792 | −16.382 | 27.582 | 5GY3/4 |
| RPP 25822 | 31.462 | −13.748 | 19.516 | 2.5G2/4 |
| RPP 26098 | 32.384 | −15.992 | 24.404 | 2.5G2/4 |
| RPP 26105 | 32.61 | −14.282 | 20.21 | 2.5G2/4 |

Based on these data, the three homozygous OVG hybrids RPP 25822, RPP 26098 and RPP 26105 have darker interior flesh color (lower L* values) than the other hybrids evaluated. In addition, based on a* and b* chroma values, the interior flesh of the homozygous OVG hybrids have more of a bluish hue (lower b* values). With respect to the calyx color, the homozygous OVG hybrids are darker (L*) as well as greener (a*) and bluer (b*) in hue than the other hybrids. In this study, no distinctive differences were noted with respect to peduncle color.

Example 8

Post-Harvest Study

A post-harvest study was conducted in Fall 2011 in Naples, Fla. to evaluate post-harvest color retention, handling and quality performance of immature green OVG pepper fruits, e.g., how fruits perform when subjected to standard commercial harvest, handling and storage practices.

A panel of 15 pepper varieties/lines was assessed in a study with 2 replicates of 20 plants for each variety/line. Yield data were collected. From each variety/line, 50 pepper fruits of good quality, uniform size and free of scratching or damage were selected. Fruits were washed by dipping in 70° F. water bath, rinsed with tap water and wiped dry with a paper towel. Fruits were labeled with a marker, and fruits from each plot carefully packed into black plastic crates. The crated fruits were then stored at 50±5° F. to replicate commercial handling conditions.

On each of post-harvest days 1, 5, 8, 12 and 15 (DPH1, DPH5, DPH8, DPH12 and DPH15), 10 fruits per variety/line were evaluated for the following parameters:

Digital images were captured for Image Analysis as described above in Example 1.
Weight (g) of fruit
Marketability (acceptable appearance; yes/no)
Hand firmness rating on 1-3 scale (1/soft; 2/average; 3/firm)
Visual Observations: bruising, silvering, micro-cracking, discoloration, etc.

A summary of the results of image analysis of surface fruit color (L* values) at post-harvest day 1 (DPH1) is shown in FIG. 27. The values for L* (FIG. 28), a* (FIG. 29) and b* (FIG. 30) at post-harvest days 1, 5, 8, 12 and 15 (DPH1, DPH5, DPH8, DPH12, and DPH15) are also shown. A summary of the day 1 post-harvest results are shown below in Table 8.

TABLE 8

Day 1 Post Harvest

| Genotype | Variety | L value | a value | b value |
|---|---|---|---|---|
| Non-OVG Hybrid | 8302 | 28.78 | −16.03 | 21.53 |
| | 2815 | 31.22 | −17.93 | 24.55 |
| | Vanguard | 32.14 | −18.61 | 26.09 |
| | Aristotle | 31.65 | −18.36 | 25.74 |
| | nn024272 | 28.40 | −14.91 | 20.61 |
| | nn024226 | 28.69 | −16.00 | 21.55 |
| | nn029991 | 31.61 | −17.30 | 24.06 |
| | nn029869 | 30.69 | −17.38 | 23.92 |
| Heterozygous OVG Hybrid | Tomcat | 28.35 | −15.50 | 21.44 |
| Homozygous OVG Hybrid | nn025822 | 24.97 | −9.41 | 12.89 |
| | nn026098 | 24.57 | −10.03 | 13.89 |
| | nn026105 | 24.25 | −10.34 | 14.36 |

The fruits from the three homozygous OVG hybrids retained their darker color over the course of 15 days post-harvest. In addition, no discoloration was observed (e.g., no darkening of the color, the integrity of the color was maintained in storage, and the like), and no susceptibility to post-harvest disorders was observed.

With respect to the other parameters that were assessed in this study, it was determined that during storage: (1) all varieties lost moisture and freshness, (2) all varieties/lines decreased fruit weight at a linear rate, (3) post-harvest quality of fruits from homozygous OVG hybrids RPP 26098, RPP 25822 and RPP 26105 was similar to commercial checks. In addition, yield was within normal commercial limits for total yield and size distribution of fruits for the three OVG hybrids.

No significant differences were observed between the two replicates of this study.

Example 9

Sensory Evaluation of OVG Hybrids

Trained panelists performed a sensory evaluation in which 4 varieties of immature green pepper fruits were rated for various attributes and quality factors (see Table 9). Homozygous OVG hybrids RPP 25822, RPP 26098 and RPP 26105 and one non-OVG hybrids were included in the panel.

TABLE 9

Sensory Evaluation

| LABEL | RPP 25822 | RPP 26098 | RPP 26105 | Non-OVG Hybrid |
|---|---|---|---|---|
| Temperature Avg. (° F.) | 63.8 | 67.1 | 65.6 | 66.1 |
| Total Soluble Solids Avg (%) | 4.2 | 4.0 | 4.5 | 4.2 |
| ATTRIBUTES** | | | | |
| Bell Pepper Intensity | 7.8 | 5.1 | 6.8 | 6.2 |
| Green/Grassy | 4.6 | 2.2 | 2.8 | 2.8 |
| Musty/Fermented | 0.0 | 0.0 | 0.0 | 0.0 |
| Chemical | 0.0 | 0.0 | 0.0 | 0.0 |
| Capsicum-Chile Odor | 1.1 | 0.4 | 0.5 | 0.6 |
| Sweetness | 3.0 | 3.2 | 3.9 | 2.7 |
| Sourness | 0.2 | 0.1 | 0.1 | 0.8 |
| Bitterness | 1.3 | 0.8 | 0.8 | 0.8 |
| Heat | 0.4 | 0.1 | 0.1 | 0.3 |
| Juiciness | 7.6 | 7.6 | 7.8 | 7.7 |
| Pulp Firmness/Crunchiness | 9.8 | 9.4 | 9.4 | 9.1 |
| Graininess/Mealyness | 0.0 | 0.0 | 0.0 | 0.0 |
| Sliminess | 0.0 | 0.0 | 0.0 | 0.0 |
| External Qualities | 13.0 | 14.0 | 14.0 | 12.0 |
| External Appearance Defects | 0.0 | 0.0 | 0.0 | 0.0 |
| Skin Color | 14.0 | 14.0 | 14.0 | 12.1 |
| Flesh Color | 13.0 | 12.9 | 12.9 | 11.5 |
| Internal Qualities | 13.3 | 13.1 | 13.3 | 11.9 |
| QUALITY FACTOR** | | | | |
| Appearance | 13.2 | 13.4 | 13.0 | 12.0 |
| Sweet/Taste Balance | 12.3 | 12.4 | 12.4 | 10.9 |
| Texture | 12.8 | 12.6 | 12.1 | 11.9 |
| Aroma | 12.4 | 11.7 | 11.5 | 11.4 |
| OVERALL QUALITY** | 12.5 | 12.5 | 12.8 | 11.4 |

**All ratings on a scale of 0 to 15

The OVG hybrids have higher Overall Quality ratings than the non-OVG hybrid primarily due to higher Appearance scores, increased Sweetness and lower scores for Sourness, resulting in higher Sweet/Taste Balance scores. In general, the sweetness scores were ranked on the low side of the scale for all varieties due to strong bell pepper aroma/flavor intensity in the samples, which masked the sweetness.

The Appearance scores for all varieties were rated in the excellent range. The Aroma scores for all varieties were rated in the good to excellent range.

This sensory evaluation was repeated on materials harvested during a different growing season and similar results were observed.

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the invention and the like may be practiced within the scope of the invention.

We claim:

1. A seed of pepper cultivar RPP 25822, RPP 26098, RPP 26105, 16452A, 16452B or 16452C, a representative sample of seed having been deposited under ATCC Accession Nos. PTA-121983, PTA-121984, PTA-121982, PTA-121980, PTA-121981 and PTA-121985, respectively, or pepper cultivar 8728C, a representative sample of seed having been deposited under NCIMB Accession Number 41858.

2. A plant of pepper cultivar RPP 25822, RPP 26098, RPP 26105, 16452A, 16452B or 16452C, a representative sample of seed having been deposited under ATCC Accession Nos. PTA-121983, PTA-121984, PTA-121982, PTA-121980, PTA-121981 and PTA-121985, respectively, or pepper cultivar 8728C, a representative sample of seed having been deposited under NCIMB Accession Number 41858.

3. A pepper plant, or a part thereof, having all the physiological and morphological characteristics of the pepper plant of claim 2.

4. A plant comprising at least one set of chromosomes of the plant of claim 2, wherein the plant produces sweet pepper fruits, and wherein the plant of claim 2 is pepper cultivar 16452A, 16452B or 16452C.

5. A plant part of the pepper plant of claim 2.

6. The plant part of claim 5, wherein the plant part is a fruit, pollen, an ovule, an anther, a root, a leaf, or a cell.

7. A tissue culture of regenerable cells of the plant of claim 2.

8. A pepper plant regenerated from a tissue culture of regenerable cells of the plant of claim 2, wherein said regenerated pepper plant comprises all of the physiological and morphological characteristics of the plant of claim 2.

9. A processed product from the plant of claim 2, wherein the processed product comprises dehydrated, cut, sliced, chopped, diced, ground, pureed, dried, canned, jarred, washed, packaged, refrigerated, frozen, blanched and/or heated pepper fruits.

10. A method of producing a pepper seed, the method comprising crossing the plant of claim 2 with itself or a second pepper plant, and harvesting the resulting seed, wherein the plant of claim 2 is pepper cultivar RPP 25822, RPP 26098, RPP 26105, 16452A, 16452B or 16452C.

11. An F1 pepper seed produced by the method of claim 10, wherein the plant to be crossed is pepper cultivar 16452A, 16452B or 16452C, and wherein the pepper seed produces a pepper plant that produces sweet pepper fruits.

12. An F1 pepper plant, or part thereof, produced by growing the seed of claim 11.

13. A method for producing a seed of a pepper plant derived from the plant of claim 2, the method comprising:
(a) crossing a plant of pepper cultivar RPP 25822, RPP 26098, RPP 26105, 16452A, 16452B or 16452C, a representative sample of seed having been deposited under ATCC Accession Nos. PTA-121983, PTA-121984, PTA-121982, PTA-121980, PTA-121981 and PTA-121985, respectively, or pepper cultivar 8728C, a representative sample of seed having been deposited under NCIMB Accession Number 41858, with a second pepper plant;
(b) allowing seed to form;
(c) growing a plant from the seed of step (b) to produce a plant derived from pepper cultivar RPP 25822, RPP 26098, RPP 26105, 8728C, 16452A, 16452B or 16452C;
(d) selfing the plant of step (c) or crossing it to a second pepper plant to form additional pepper seed derived from pepper cultivar RPP 25822, RPP 26098, RPP 26105, 8728C, 16452A, 16452B or 16452C; and
(e) optionally repeating steps (c) and (d) one or more times to generate further derived pepper seed from pepper cultivar RPP 25822, RPP 26098, RPP 26105, 8728C, 16452A, 16452B or 16452C, wherein in step (c) a plant is grown from the additional pepper seed of step (d) in place of growing a plant from the seed of step (b).

14. A method of vegetatively propagating the plant of claim 2, the method comprising:
(a) collecting tissue capable of being propagated from a plant of pepper cultivar RPP 25822, RPP 26098, RPP 26105, 16452A, 16452B or 16452C, a representative sample of seed having been deposited under ATCC Accession Nos. PTA-121983, PTA-121984, PTA-121982, PTA-121980, PTA-121981 and PTA-121985, respectively, or pepper cultivar 8728C, a representative sample of seed having been deposited under NCIMB Accession Number 41858;
(b) cultivating the tissue to obtain proliferated shoots; and
(c) rooting the proliferated shoots to obtain rooted plantlets.

15. Plants or plantlets obtained by the method of claim 14.

16. A method of introducing a desired added trait into pepper cultivar 8728C, 16452A, 16452B or 16452C, the method comprising:
(a) crossing a plant of pepper cultivar 8728C, 16452A, 16452B or 16452C with a pepper plant that comprises a desired added trait to produce F1 progeny;
(b) selecting an F1 progeny that comprises the desired added trait;
(c) backcrossing the selected F1 progeny with the same pepper cultivar as in step (a) to produce backcross progeny;
(d) selecting backcross progeny comprising the desired added trait; and
(e) repeating steps (c) and (d) one or more times to produce a plant derived from pepper cultivar 8728C, 16452A, 16452B or 16452C comprising a desired added trait and essentially all of the physiological and morphological characteristics of the pepper cultivar 8728C, 16452A, 16452B or 16452C, wherein in step (c) the selected backcross progeny produced in step (d) is used in place of the selected F1 progeny of step (b).

17. A pepper plant produced by the method of claim 16 or a selfed progeny thereof, wherein the pepper plant has the desired added trait.

18. Seed that produces the plant of claim 17.

19. A method of producing a plant of pepper cultivar 8728C, 16452A, 16452B or 16452C comprising a desired added trait, the method comprising introducing a transgene conferring the desired trait into the plant of claim 2.

20. A pepper plant produced by the method of claim 19 or a selfed progeny thereof, wherein the pepper plant has the desired added trait.

21. An F1 seed produced by a method comprising crossing the plant of claim 20 with a second pepper plant, and harvesting the resulting seed, wherein the seed produces a plant that has the desired trait.

22. Seed that produces the plant of claim 20.

23. A method of producing a pepper fruit, the method comprising:
(a) growing the pepper plant according to claim 2 to produce a pepper fruit; and
(b) harvesting the pepper fruit.

24. A method of producing a processed product, the method comprising
(a) obtaining a fruit of the plant of claim 2; and
(b) processing said fruit to produce a processed product.

* * * * *

```
                           SEQUENCE LISTING

<160> NUMBER OF SEQ ID NOS: 12

<210> SEQ ID NO 1
<211> LENGTH: 28
<212> TYPE: DNA
<213> ORGANISM: Artificial Sequence
<220> FEATURE:
<223> OTHER INFORMATION: Marker locus SP 436 forward primer

<400> SEQUENCE: 1
agatattccc tccctcttca ttattcct                                      28

<210> SEQ ID NO 2
<211> LENGTH: 20
<212> TYPE: DNA
<213> ORGANISM: Artificial Sequence
<220> FEATURE:
<223> OTHER INFORMATION: Marker locus SP 436 reverse primer

<400> SEQUENCE: 2
gaggctgcac gaacagatca                                               20

<210> SEQ ID NO 3
<211> LENGTH: 22
<212> TYPE: DNA
<213> ORGANISM: Artificial Sequence
<220> FEATURE:
<223> OTHER INFORMATION: Marker locus SP626 forward primer

<400> SEQUENCE: 3
gtgaaggaag cgtgatgaat gg                                            22

<210> SEQ ID NO 4
<211> LENGTH: 22
<212> TYPE: DNA
<213> ORGANISM: Artificial Sequence
<220> FEATURE:
<223> OTHER INFORMATION: Marker locus SP626 reverse primer

<400> SEQUENCE: 4
cctaacagca cttcaggtgc aa                                            22

<210> SEQ ID NO 5
<211> LENGTH: 23
<212> TYPE: DNA
<213> ORGANISM: Artificial Sequence
<220> FEATURE:
<223> OTHER INFORMATION: Marker locus SP693 forward primer

<400> SEQUENCE: 5
acgaggatgc aactgactca aaa                                           23

<210> SEQ ID NO 6
<211> LENGTH: 25
<212> TYPE: DNA
<213> ORGANISM: Artificial Sequence
<220> FEATURE:
<223> OTHER INFORMATION: Marker locus SP693 reverse primer

<400> SEQUENCE: 6
cccaagtcac taggttgttg attct                                         25
```

<210> SEQ ID NO 7
<211> LENGTH: 30
<212> TYPE: DNA
<213> ORGANISM: Artificial Sequence
<220> FEATURE:
<223> OTHER INFORMATION: Marker locus SP694 forward primer

<400> SEQUENCE: 7
tcttattgga gcaaagaata actgggttat                           30

<210> SEQ ID NO 8
<211> LENGTH: 30
<212> TYPE: DNA
<213> ORGANISM: Artificial Sequence
<220> FEATURE:
<223> OTHER INFORMATION: Marker locus SP694 reverse primer

<400> SEQUENCE: 8
tgcactctat gtgtttgata ttttgtctca                           30

<210> SEQ ID NO 9
<211> LENGTH: 19
<212> TYPE: DNA
<213> ORGANISM: Artificial Sequence
<220> FEATURE:
<223> OTHER INFORMATION: Extreme dark green allele specific probe
      (marker locus SP 436)

<400> SEQUENCE: 9
ctggagttac cagtttata                                       19

<210> SEQ ID NO 10
<211> LENGTH: 19
<212> TYPE: DNA
<213> ORGANISM: Artificial Sequence
<220> FEATURE:
<223> OTHER INFORMATION: Extreme dark green allele specific probe
      (marker locus SP626)

<400> SEQUENCE: 10
tagtacggtg tgccaacaa                                       19

<210> SEQ ID NO 11
<211> LENGTH: 16
<212> TYPE: DNA
<213> ORGANISM: Artificial Sequence
<220> FEATURE:
<223> OTHER INFORMATION: Extreme dark green allele specific probe
      (marker locus SP693)

<400> SEQUENCE: 11
atgatgcgaa tggtca                                          16

<210> SEQ ID NO 12
<211> LENGTH: 22
<212> TYPE: DNA
<213> ORGANISM: Artificial Sequence
<220> FEATURE:
<223> OTHER INFORMATION: Extreme dark green allele specific probe
      (marker locus SP694)

<400> SEQUENCE: 12
tgtagcttca atctatttgt tc                                   22